United States Patent
Badiavas et al.

(10) Patent No.: US 10,500,231 B2
(45) Date of Patent: Dec. 10, 2019

(54) METHOD FOR ISOLATION AND PURIFICATION OF MICROVESICLES FROM CELL CULTURE SUPERNATANTS AND BIOLOGICAL FLUIDS

(71) Applicant: University of Miami, Miami, FL (US)

(72) Inventors: Evangelos V. Badiavas, Coral Gables, FL (US); Arsalan Q. Shabbir, Miami, FL (US); Stephen C. Davis, El Portal, FL (US)

(73) Assignee: University of Miami, Miami, FL (US)

(*) Notice: Subject to any disclaimer, the term of this patent is extended or adjusted under 35 U.S.C. 154(b) by 421 days.

(21) Appl. No.: 14/775,382

(22) PCT Filed: Mar. 12, 2014

(86) PCT No.: PCT/US2014/024629
§ 371 (c)(1),
(2) Date: Sep. 11, 2015

(87) PCT Pub. No.: WO2014/159662
PCT Pub. Date: Oct. 2, 2014

(65) Prior Publication Data
US 2016/0184363 A1 Jun. 30, 2016

Related U.S. Application Data

(60) Provisional application No. 61/778,591, filed on Mar. 13, 2013.

(51) Int. Cl.
| | |
|---|---|
| A61P 17/00 | (2006.01) |
| A61K 9/127 | (2006.01) |
| A61K 35/28 | (2015.01) |
| A61K 35/12 | (2015.01) |
| A61K 35/16 | (2015.01) |
| A61K 8/98 | (2006.01) |
| A61K 35/22 | (2015.01) |
| A61Q 19/00 | (2006.01) |
| A61Q 19/08 | (2006.01) |

(52) U.S. Cl.
CPC .............. *A61K 35/28* (2013.01); *A61K 8/981* (2013.01); *A61K 8/983* (2013.01); *A61K 35/12* (2013.01); *A61K 35/16* (2013.01); *A61K 35/22* (2013.01); *A61Q 19/00* (2013.01); *A61Q 19/08* (2013.01); *A61K 2800/74* (2013.01); *A61K 2800/86* (2013.01)

(58) Field of Classification Search
None
See application file for complete search history.

(56) References Cited

U.S. PATENT DOCUMENTS

| | | | |
|---|---|---|---|
| 6,331,298 B1 | 12/2001 | Ferguson et al. | |
| 6,509,369 B2 | 1/2003 | Scott et al. | |
| 6,793,945 B2 | 9/2004 | Bathurst et al. | |
| 7,807,438 B2 | 10/2010 | Abrignani et al. | |
| 7,897,356 B2 | 3/2011 | Klass et al. | |
| 8,021,847 B2 | 9/2011 | Pietrzkowski | |
| 8,211,653 B2 | 7/2012 | Klass et al. | |
| 8,216,784 B2 | 7/2012 | Taylor et al. | |
| 8,278,059 B2 | 10/2012 | Klass et al. | |
| 8,288,172 B2 | 10/2012 | Ichim et al. | |
| 8,343,485 B2 | 1/2013 | Pecora et al. | |
| 8,343,725 B2 | 1/2013 | Croce et al. | |
| 8,349,560 B2 | 1/2013 | Croce | |
| 8,349,561 B2 | 1/2013 | Croce | |
| 8,349,568 B2 | 1/2013 | Croce et al. | |
| 8,349,574 B2 | 1/2013 | Bates et al. | |
| 8,901,284 B2 | 12/2014 | Vlassov et al. | |
| 9,005,888 B2 | 4/2015 | Antes et al. | |
| 9,066,971 B2 | 6/2015 | Gho et al. | |
| 9,828,603 B2 | 11/2017 | Marban | |
| 9,856,477 B2 | 1/2018 | Lötvall | |
| 2003/0198642 A1 | 10/2003 | Geuze et al. | |
| 2004/0132729 A1 | 7/2004 | Salituro et al. | |
| 2004/0171623 A1 | 9/2004 | Reynolds et al. | |

(Continued)

FOREIGN PATENT DOCUMENTS

| | | |
|---|---|---|
| EP | 1 780 267 A2 | 5/2007 |
| EP | 2604288 A1 | 6/2013 |

(Continued)

OTHER PUBLICATIONS

SystemBiosciences Exoquick-TC Exosome Precipitation Solution Aug. 5, 2011.*
Lasser et al. Journal of Visualized Experiments, Jan. 2012, pp. 1-6.*
Albarran Y Carvajal et al. (2007) "MVA E2 recombinant vaccine in the treatment of human papillomavirus infection in men presenting intraurethral flat condyloma: a phase I/II study," Biodrugs. 21(1):47-59.
Andreu et al. (Jun. 20, 2016) "Comparative Analysis of EV Isolation Procedures for miRNAs Detection in Serum Samples," J. Extracell. Vesicles. 5:31655.

(Continued)

*Primary Examiner* — Julie Wu
*Assistant Examiner* — Douglas F White
(74) *Attorney, Agent, or Firm* — Lathrop Gage LLP; Judith Stone-Hulslander

(57) ABSTRACT

The present invention relates to the fields of medicine, cell biology, molecular biology and genetics. In particular, the present invention provides methods to isolate and purify microvesicles from cell culture supernatants and biological fluids. The present invention also provides pharmaceutical compositions of microvesicles to promote or enhance wound healing, stimulate tissue regeneration, remodel scarred tissue, modulate immune reactions, alter neoplastic cell growth and/or mobility, or alter normal cell growth and/or mobility. The present invention also provides compositions of microvesicles to be used as diagnostic reagents, and methods to prepare the compositions of microvesicles.

36 Claims, 32 Drawing Sheets

Specification includes a Sequence Listing.

(56) References Cited

U.S. PATENT DOCUMENTS

| | | |
|---|---|---|
| 2004/0209901 A1 | 10/2004 | Adams et al. |
| 2004/0220393 A1 | 11/2004 | Ward et al. |
| 2006/0116321 A1 | 6/2006 | Robbins et al. |
| 2008/0268429 A1* | 10/2008 | Pietrzkowski ..... A61K 47/6901 435/6.18 |
| 2009/0292109 A1* | 11/2009 | Gronke ................ C07K 1/30 530/344 |
| 2010/0047335 A1 | 2/2010 | Egea et al. |
| 2010/0104542 A1 | 4/2010 | Austen, Jr. |
| 2010/0184046 A1* | 7/2010 | Klass ................ C12Q 1/6886 435/7.1 |
| 2010/0189744 A1 | 7/2010 | Bryan et al. |
| 2010/0196426 A1* | 8/2010 | Skog .................. C12Q 1/6806 424/400 |
| 2010/0255514 A1* | 10/2010 | Rak .................... A61K 45/06 435/7.92 |
| 2011/0003008 A1 | 1/2011 | Lim |
| 2011/0195426 A1* | 8/2011 | Russo ............... C12N 15/1017 435/6.17 |
| 2012/0058492 A1 | 3/2012 | Lozupone et al. |
| 2012/0070858 A1 | 3/2012 | Contreras et al. |
| 2012/0093885 A1* | 4/2012 | Sahoo ................ A61K 35/51 424/400 |
| 2012/0171290 A1 | 7/2012 | Coursaget et al. |
| 2012/0214151 A1 | 8/2012 | Newman et al. |
| 2012/0238467 A1 | 9/2012 | Taylor et al. |
| 2012/0309041 A1 | 12/2012 | Timmers et al. |
| 2012/0315324 A1 | 12/2012 | Zhang |

FOREIGN PATENT DOCUMENTS

| | | |
|---|---|---|
| WO | 2004/014954 A1 | 2/2004 |
| WO | 2006/007529 A2 | 1/2006 |
| WO | 2007/103572 A2 | 9/2007 |
| WO | 2007/126386 A1 | 11/2007 |
| WO | 2009/092386 A2 | 7/2009 |
| WO | 2009/115561 A1 | 9/2009 |
| WO | 2010/119256 A1 | 10/2010 |
| WO | 2011/000551 A1 | 1/2011 |
| WO | 2012/002760 A2 | 1/2012 |
| WO | 2012/020307 A2 | 2/2012 |
| WO | 2012053976 A1 | 4/2012 |
| WO | 2012/108842 A1 | 8/2012 |
| WO | 2012/110099 A1 | 8/2012 |
| WO | 2012/110253 A2 | 8/2012 |
| WO | 2012/126531 A1 | 9/2012 |
| WO | 2012/135844 A2 | 10/2012 |
| WO | 2012/169970 A1 | 12/2012 |
| WO | 2013014691 A1 | 1/2013 |
| WO | 2013/022786 A2 | 2/2013 |
| WO | 2013/188832 A1 | 12/2013 |

OTHER PUBLICATIONS

Grenier et al. (1987) "Functional characterization of extracellular vesicles produced by Bacteroides gingivalis," Infection and Immunity. 55(1):111-117.

Merz et al. (2010) "Biochemical and Morphological Properties of Hepatitis C Virus Particles and Determination of Their Lipidome," J. Bol. Chem. 286(4):3018-3032.

Mori et al. (2008) "Human herpesvirus-6 induces MVB formation, and virus egress occurs by an exosomal release pathway," Traffic. 9:1728-1742.

Radhakrishnan et al. (2010) "Protein Analysis of Purified Respiratory Syncytial Virus Particles Reveals an Important Role for Heat Shock Protein 90 in Virus Particle Assembly," Mol. Cell. Proteomics. 9(9):1829-1848.

Raposo et al. (Feb. 18, 2013) "Extracellular vesicles: Exosomes, microvesicles, and friends," J. Cell. Biology. 4:373-383.

System Biosciences (2013) "User Manual: ExoQuick-TC(TM) Exosome Precipitation Solution," Catalog No. EXOTCxxA-1. System Biosciences (SBI). Accessible on the Internet at URL: https://www.systembio.com/downloads/Manual_ExoTC_WEB.pdf. [Last Accessed Jan. 19, 2017].

Venugopal et al. (2010) "Recalcitrant cutaneous warts treated with recombinant quadrivalent human papillomavirus vaccine (types 6, 11, 16, and 18) in a developmentally delayed, 31-year-old white man," Arch. Dermatol. 146(5):475-477.

Villa et al. (2006) "High sustained efficacy of a prophylactic quadrivalent human papillomavirus types 6/11/16/18 L1 virus-like particle vaccine through 5 years of follow-up," Br. J. Cancer. 95:1459-1466.

Zoller (2009) "Tetraspanins: push and pull in suppressing and promoting metastasis," Nat. Rev. Cancer. 9(1):40-55.

International Search Report with Written Opinion corresponding to International Patent Application No. PCT/US2014/024629, dated Jul. 3, 2014.

Chen et al. (2013) "Cardiac progenitor-derived Exosomes protect ischemic myocardium from acute ischemia/reperfusion injury," Biochem. Biophys. Res. Commun., 431:14 pages.

Ludwig et al. (2018) "Precipitation with polyethylene glycol followed by washing and pelleting by ultracentrifugation enriches extracellular vesicles from tissue culture supernatans in small and large scales," Journal of Extracellular Vesicles, 7:1-20.

Taylor et al. (2011) "Exosome Isolation for Proteomic Analyses and RNA Profiling," Methods in Molecular Biology, Chapter 15, 13 pages.

\* cited by examiner

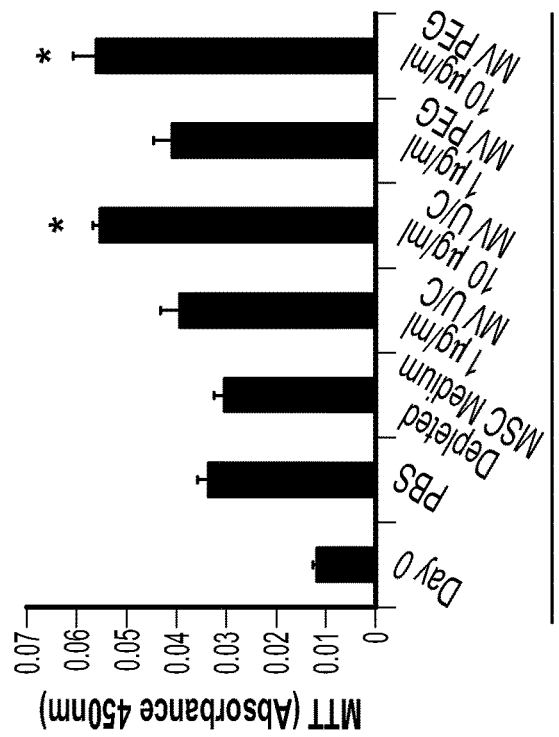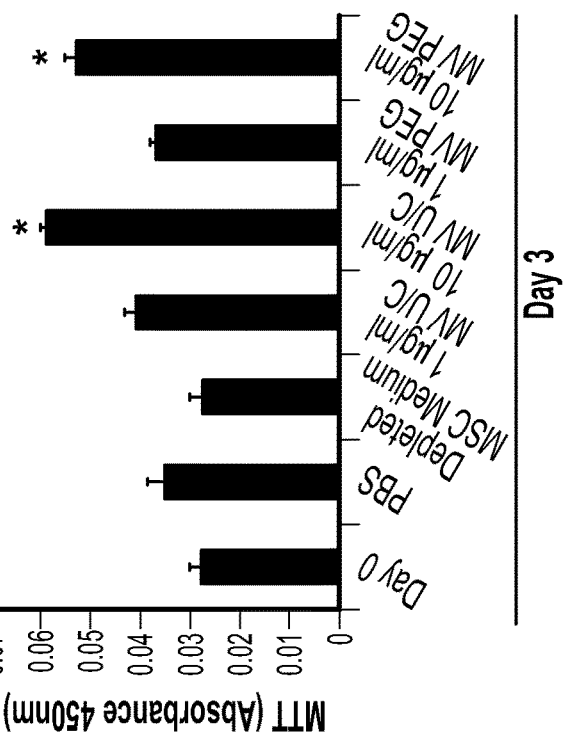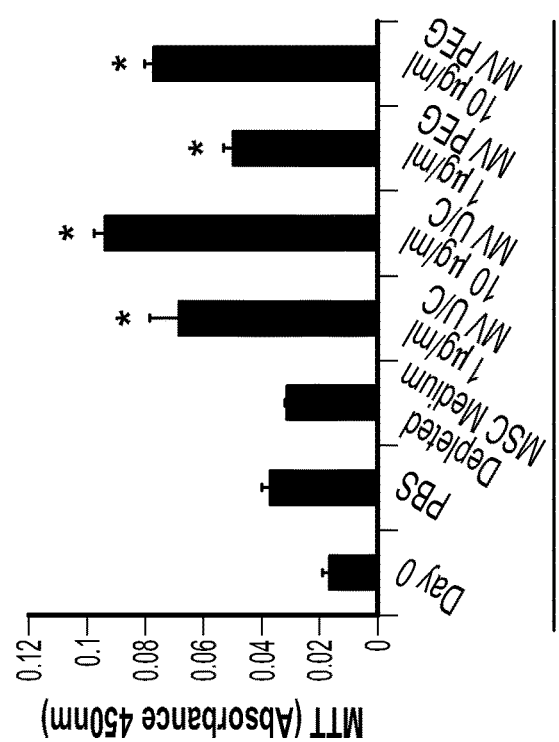
FIG. 12A
FIG. 12B
FIG. 12C

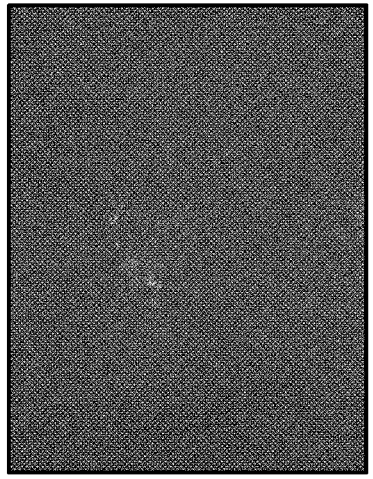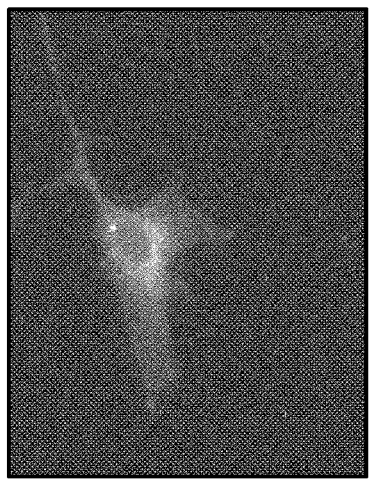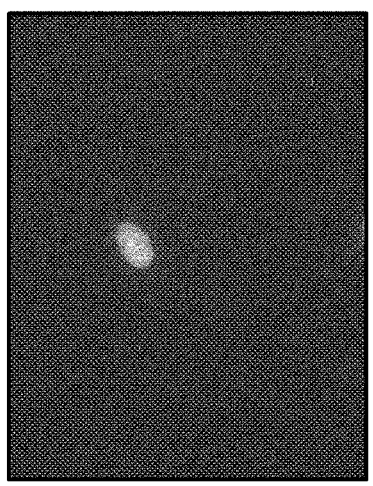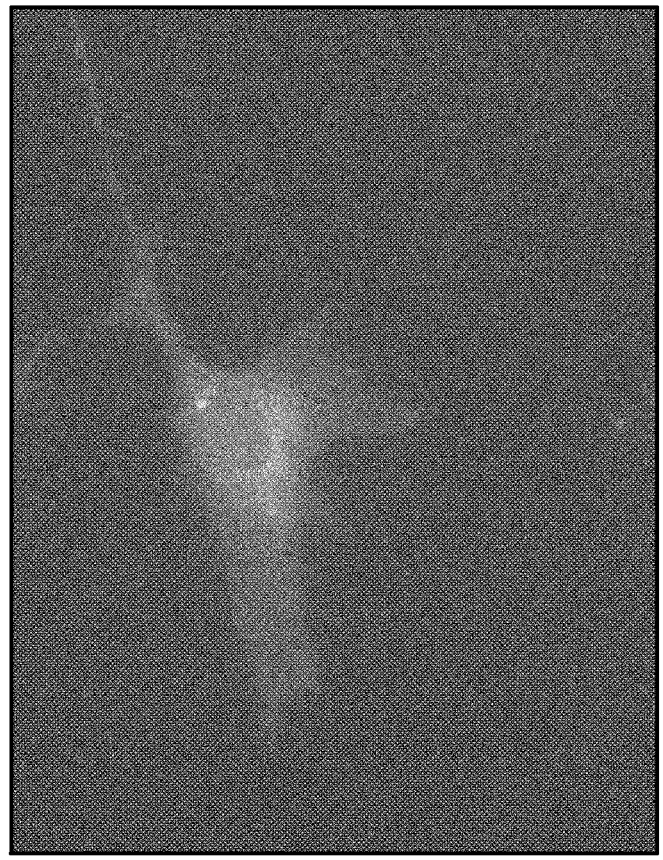
FIG. 15

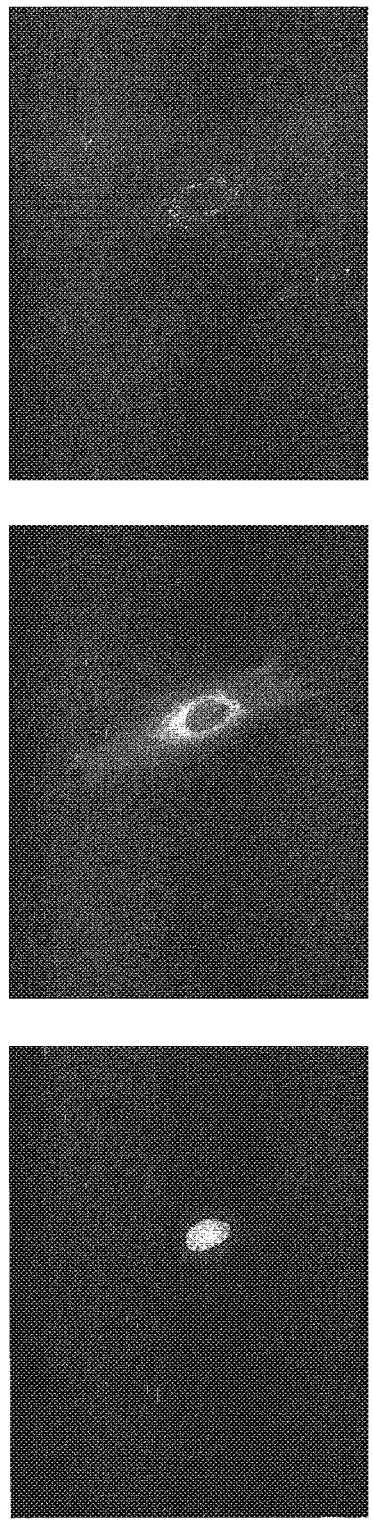
FIG. 16

PBS hMSC Conditioned medium depleted of MV hMSC MV ultracentrifugation hMSC MV PEG precipitation Human Plasma MV PEG Precipitation Phospho-STAT3 Tyr705

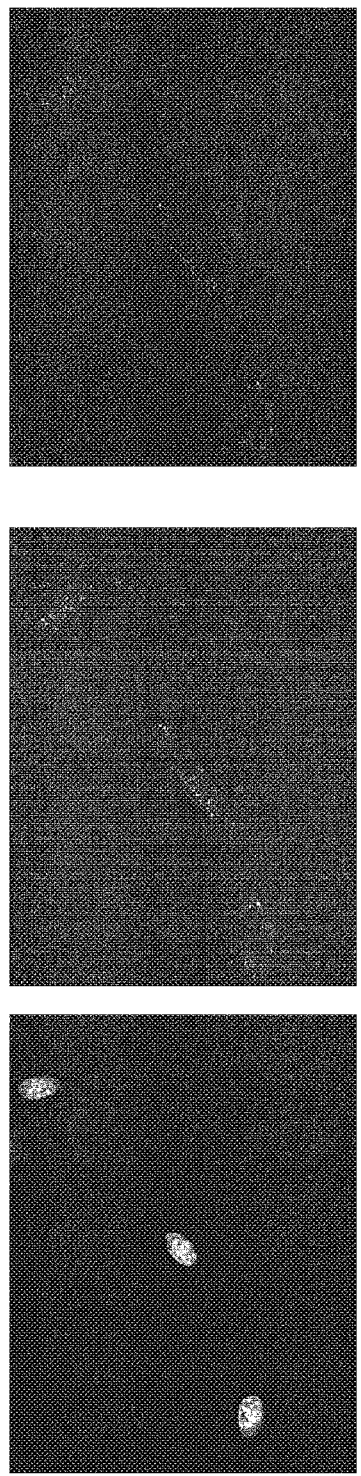
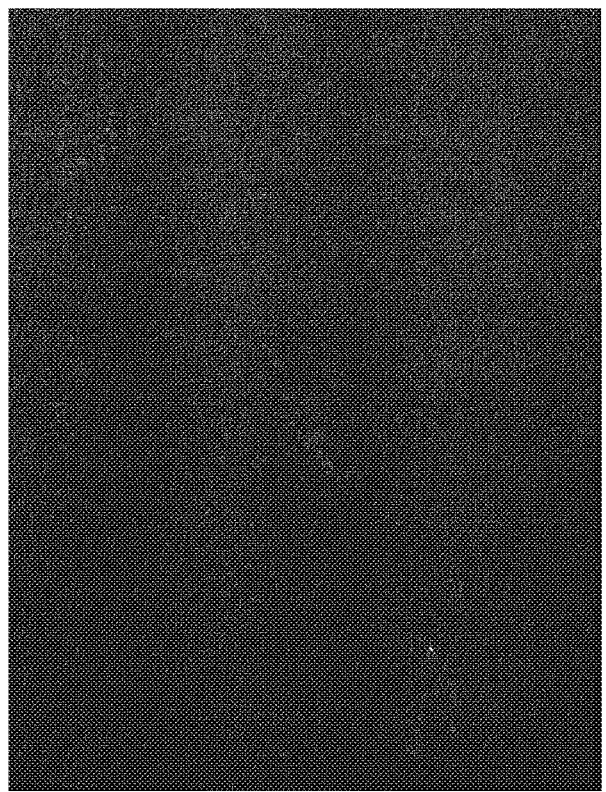
FIG. 21

Figure 5: Full Thickness Wound Treated with MV's Prepared by Our Methods at Day 28 (12.5X)
Arrows Illustrate New Nerve Growth into a Remodeling Wound.
Nerve Growth is Associated with Angiogenesis - Highlighted in the Circled Areas
These Findings are Highly Indicative of Tissue Regeneration
This has Never been Observed
Not Observed in Controls or Ultracentrifuged MV Treated Wounds

FIG. 26

METHOD FOR ISOLATION AND PURIFICATION OF MICROVESICLES FROM CELL CULTURE SUPERNATANTS AND BIOLOGICAL FLUIDS

FIELD OF THE INVENTION

The present invention relates to the fields of medicine, cell biology, molecular biology and genetics. In particular, the present invention provides methods to isolate and purify microvesicles from cell culture supernatants and biological fluids. The present invention also provides pharmaceutical compositions of microvesicles to promote or enhance wound healing, stimulate tissue regeneration, remodel scarred tissue, modulate immune reactions, alter neoplastic cell growth and/or mobility, or alter normal cell growth and/or mobility. The present invention also provides compositions of microvesicles to be used as diagnostic reagents, and methods to prepare the compositions of microvesicles.

BACKGROUND

Microvesicles are secreted by many, if not all, cell types in vitro and in vivo, and are present in biological fluids, such as, for example, blood, interstitial fluid, urine, saliva, and tears. Microvesicles are vesicles comprising lipid bilayers, formed from the plasma membrane of cells, and are heterogeneous in size, ranging from about 2 nm to about 5000 nm. The cell from which a microvesicle is formed is herein referred to as "the host cell". Microvesicles are a heterogeneous population of vesicles and include, for example, ectosomes, microparticles, microvesicles, nanovesicles, shedding vesicles and membrane particles.

Microvesicles exhibit membrane proteins from their host cell on their membrane surface, and may also contain molecules within the microvesicle from the host cell, such as, for example, mRNA, miRNA, tRNA, RNA, DNA, lipids, proteins or infectious particles. These molecules may result from, or be, recombinant molecules introduced into the host cell. Microvesicles play a critical role in intercellular communication, and can act locally and distally within the body, inducing changes in cells by fusing with a target cell, introducing the molecules transported on and/or in the microvesicle to the target cell. For example, microvesicles have been implicated in anti-tumor reversal, cancer, tumor immune suppression, metastasis, tumor-stroma interactions, angiogenesis and tissue regeneration. Microvesicles may also be used to diagnose disease, as they have been shown to carry bio-markers of several diseases, including, for example, cardiac disease, HIV and leukemia.

Despite the importance of microvesicles, isolating microvesicles in useful quantities, while preserving their structural and functional integrity, remains problematic. The traditional procedure utilizes ultracentrifugation to isolate microvesicles from samples.

For example, U.S. Pat. No. 7,807,438 discloses a method for isolation of hepatitis C virus. The method comprises the separation of particles termed exosomes from the blood plasma of an individual infected with hepatitis C virus (HCV) and the extraction of RNA from these exosome particles.

In another example, U.S. Patent Application US20030198642A1 discloses [e]xosomes . . . derived from MHC class II enriched compartments in antigen presenting cells . . . [for] a . . . vaccination vehicle.

In another example, U.S. Patent Application US20060116321A1 discloses methods and compositions for use in mediating an immunosuppressive reaction. The compositions . . . comprise exosomes having immunosuppressive activity. Such exosomes may be derived from a variety of different cell types, including antigen-presenting cells such as dendritic cells and macrophages. Prior to isolation of exosomes, the cells may be genetically engineered to express molecules capable of enhancing the immunosuppressive activity of said exosomes and/or may be exposed to one or more agents, such as cytokines or cytokine inhibitors, which are also capable of enhancing the immunosuppressive activity of exosomes. The present invention also relates to the use of such exosomes for the treatment of diseases and disorders associated with undesirable activation of the immune system. The present invention also includes exosomes isolated directly from serum that have been shown to be immunosuppressive.

Ultracentrifugation may damage the microvesicles, resulting in the lysis or rupture of the vesicles. Damage to microvesicles may cause an adverse reaction in the body, if such damaged microvesicles were to be introduced.

Others have attempted alternate methods to isolate microvesicles. However, the alternate methods employed frequently isolate a sub-fraction of microvesicles, or are inefficient. For example, U.S. Patent Application US2011003008A1 discloses a particle secreted by a mesenchymal stem cell and comprising at least one biological property of a mesenchymal stem cell. The biological property may comprise a biological activity of a mesenchymal stem cell conditioned medium (MSC-CM) such as cardioprotection or reduction of infarct size. The particle may comprise a vesicle or an exosome.

In another example, U.S. Patent Application US20120070858A1 discloses a method for isolating exosomes from blood platelets using superparamagnetic nanoparticles of iron oxide ($Fe_3O_4$), by means of a charge attraction mechanism based on the predetermined Zeta potential of the exosomes. The method involves the use of iron oxide nanoparticles that are previously synthesised [sic] with a predetermined positive charge, and that bond to the negatively charged exosomes contained in the biological sample. During incubation, the cationic magnetic nanoparticles are absorbed by the surface of the membrane of the exosomes owing to electrostatic interaction. Exposure of the material to a magnetic field makes it possible to separate the exosomes bonded to the nanoparticles. The success of this technique has been confirmed by characterisation [sic] of the exosomes by flow citometry [sic]. The method has been shown to be suitable for this purpose, since it allows exosomes to be isolated and purified, without undergoing alterations of their original morphological and structural characteristics.

In another example, PCT Patent Application WO2012169970A1 discloses materials and methods for use of constrained cohydration agents in the purification of biological materials such as antibodies, viruses, cells, and cellular organelles in connection with convective chromatography, fluidized bed or co-precipitation applications.

There remains, therefore, a need to provide method to isolate and purify microvesicles without damage, and in sufficient quantities that the isolated microvesicles may subsequently be used for diagnosing disease, therapies, or research.

The present invention provides methods to isolate microvesicles from biological fluids without damaging the structural and/or functional integrity of the microvesicles. The present invention also provides methods to isolate ectosomes, microparticles, microvesicles, nanovesicles, shedding vesicles, apoptotic bodies, or membrane particles from biological fluids without damaging their structural and/or functional integrity.

SUMMARY

In one embodiment, the present invention provides a method for isolating and/or purifying microvesicles from cell culture supernatants or biological fluids utilizing precipitation agent that precipitates the microvesicle from the cell culture supernatant or biological fluid by displacing the water of solvation.

In one embodiment, the present invention provides an isolated preparation of microvesicles. In one embodiment, the isolated preparation of microvesicles is subsequently purified. In one embodiment, the isolated preparation of microvesicles is subsequently purified to yield a preparation of ectosomes. In one embodiment, the isolated preparation of microvesicles is subsequently purified to yield a preparation of microparticles. In one embodiment, the isolated preparation of microvesicles is subsequently purified to yield a preparation of nanovesicles. In one embodiment, the isolated preparation of microvesicles is subsequently purified to yield a preparation of shedding vesicles. In one embodiment, the isolated preparation of microvesicles is subsequently purified to yield a preparation of membrane particles. In one embodiment, the isolated preparation of microvesicles is subsequently purified to yield a preparation of apoptotic bodies.

In one embodiment, the present invention provides an isolated preparation of microvesicles that promotes or enhances angiogenesis. In one embodiment, the isolated preparation of microvesicles promotes or enhances angiogenesis in a patient.

In one embodiment, the present invention provides an isolated preparation of microvesicles that promotes or enhances neuronal regeneration. In one embodiment, the isolated preparation of microvesicles promotes or enhances neuronal regeneration in a patient.

In one embodiment, the present invention provides an isolated preparation of microvesicles that promotes or enhances cellular proliferation. In one embodiment, the isolated preparation of microvesicles promotes or enhances cellular proliferation in a patient.

In one embodiment, the present invention provides an isolated preparation of microvesicles that promotes or enhances cellular migration. In one embodiment, the isolated preparation of microvesicles promotes or enhances cellular migration in a patient.

In one embodiment, the present invention provides an isolated preparation of microvesicles that promotes or enhances wound healing. In one embodiment, the wound is a full-thickness burn. In one embodiment, the wound is a second-degree burn.

In one embodiment, the present invention provides an isolated preparation of microvesicles that reduces scar formation in a patient.

In one embodiment, the present invention provides an isolated preparation of microvesicles that reduces wrinkle formation in the skin of a patient.

In one embodiment, the present invention provides an isolated preparation of microvesicles that is used to diagnose the presence and/or progression of a disease in a patient. In one embodiment, the disease is metastatic melanoma. In an alternative embodiment the disease in an inflammatory/autoimmune disorder such as rheumatoid arthritis. In one embodiment, the disease is graft versus host disease.

In one embodiment, the present invention provides an isolated preparation of microvesicles that can promote functional regeneration and organization of complex tissue structures. In one embodiment the present invention provides an isolated preparation of microvesicles that can regenerate hematopoietic tissue in a patient with aplastic anemia. In one embodiment the present invention provides an isolated preparation of microvesicles that can regenerate at least one tissue in a patient with diseased, damaged or missing skin selected from the group consisting of: epithelial tissue, stromal tissue, nerve tissue, vascular tissue and adnexal structures. In one embodiment, the present invention provides an isolated preparation of microvesicles that can regenerate tissue and/or cells from all three germ layers.

In one embodiment, the present invention provides an isolated preparation of microvesicles that is used to modulate the immune system of a patient.

In one embodiment, the present invention provides an isolated preparation of microvesicles that enhances the survival of tissue or cells that is transplanted into a patient. In one embodiment, the patient is treated with the isolated preparation of microvesicles prior to receiving the transplanted tissue or cells. In an alternate embodiment, the patient is treated with the isolated preparation of microvesicles after receiving the transplanted tissue or cells. In an alternate embodiment, the tissue or cells is treated with the isolated preparation of microvesicles. In one embodiment, the tissue or cells is treated with the isolated preparation of microvesicles prior to transplantation.

In one embodiment, the present invention provides an isolated preparation of microvesicles containing at least one molecule selected from the group consisting of RNA, DNA, and protein from a host cell. In one embodiment, the host cell is engineered to express at least one molecule selected from the group consisting of RNA, DNA, and protein. In one embodiment, the isolated preparation of microvesicles containing at least one molecule selected from the group consisting of RNA, DNA, and protein from a host cell is used as a therapeutic agent.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person of ordinary skill in the art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein:

FIG. 12 shows the effect of microvesicles isolated from medium conditioned using human bone marrow-derived mesenchymal stem cells on the proliferation of normal human dermal fibroblasts (A), dermal fibroblasts obtained from a diabetic foot ulcer (B), and dermal fibroblasts obtained from a pressure foot ulcer (C). The effect of microvesicles isolated by ultracentrifugation (MV U/C) and microvesicles isolated by the methods of the present invention (MV PEG) were compared. Fibroblasts treated with PBS or microvesicle depleted culture medium were included as a control. Proliferation was determined using an MTT assay.

FIG. 15 shows the uptake of the microvesicles of the present invention into human dermal fibroblasts. Cell nuclei, resolved using Hoechst 33342 dye are shown in the panels labeled "Hoechst33342". Cells, resolved using vybrant dye are shown in the panel labeled "Vybrant-Dio". Microvesicles, resolved using PKH dye are shown in the panel labeled "PKH labeled MV". A panel where images obtained from all three dyes are overlaid is seen in the panel labeled "Composite".

FIG. 16 shows the uptake of the microvesicles of the present invention into human dermal fibroblasts. Cell nuclei, resolved using Hoechst 33342 dye are shown in the panels labeled "Hoechst33342". Cells, resolved using vybrant dye are shown in the panel labeled "Vybrant-Dio". Microvesicles, resolved using PKH dye are shown in the panel labeled "PKH labeled MV". A panel where images obtained from all three dyes are overlaid is seen in the panel labeled "Composite".

FIG. 21 shows the uptake of the microvesicles isolated according to the methods of the present invention from culture medium conditioned using bone marrow-derived stem cells obtained from a GFP expressing mouse into human dermal fibroblasts. Cell nuclei, resolved using Hoechst 33342 dye are shown in the panels labeled "Hoechst33342". Cells, resolved using vybrant dye are shown in the panel labeled "Vybrant-Dio". GFP-labeled microvesicles are shown in the panel labeled "GFP". A panel where images obtained from all three dyes are overlaid is seen in the panel labeled "Composite".

FIG. 26 shows a histological slide of a full-thickness wound, 28 days post wound, from an animal treated with microvesicles isolated from medium conditioned using autologous bone marrow-derived mesenchymal stem cells according to the methods of the present invention.

DETAILED DESCRIPTION

Figure 1:
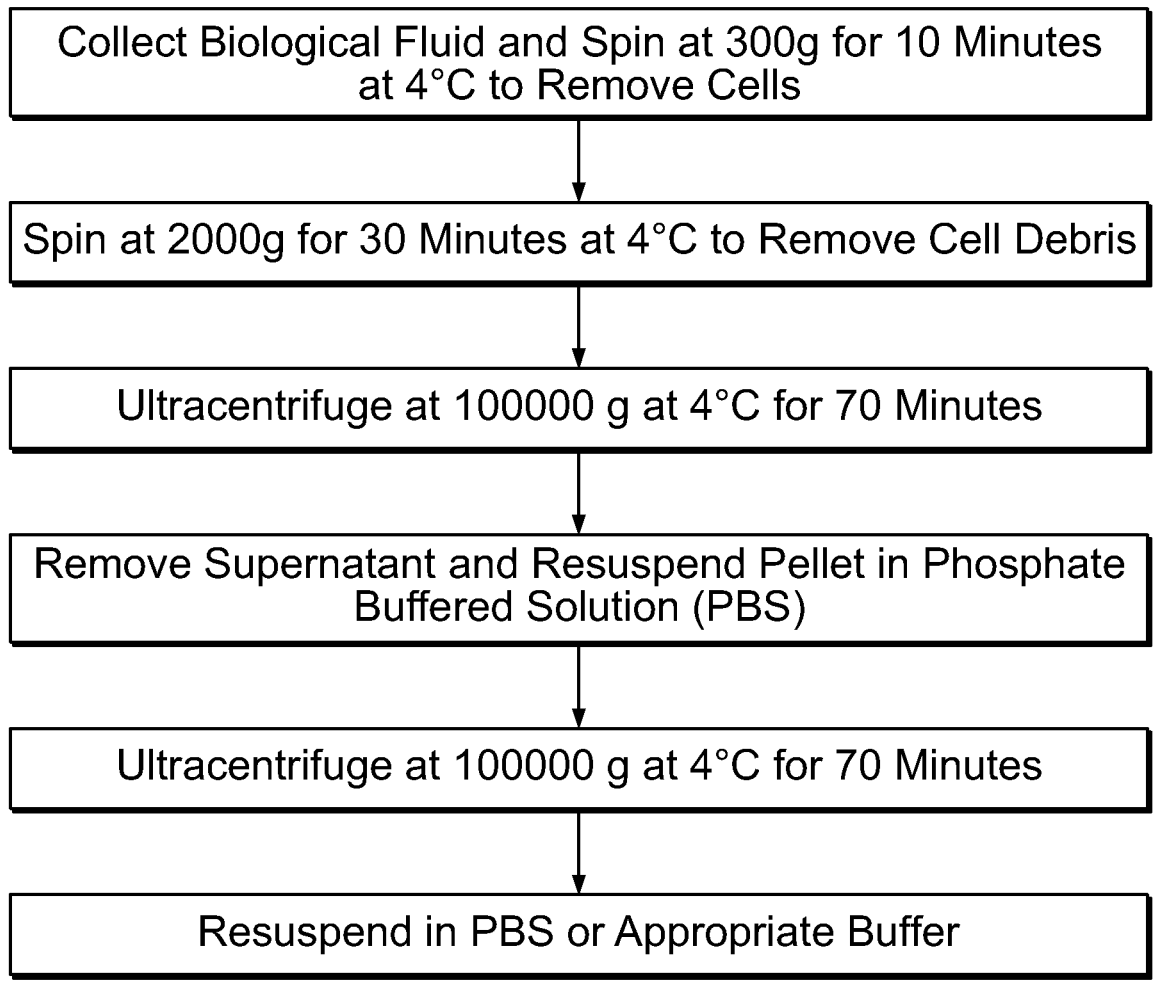
FIG. 1 shows a schematic outline of a protocol used to isolate microvesicles by ultracentrifugation.

For clarity of disclosure, and not by way of limitation, the detailed description of the invention is divided into the following subsections that describe or illustrate certain features, embodiments or applications of the present invention.

The Methods to Isolate the Microvesicles of the Present Invention

In one embodiment, microvesicles are isolated from a biological fluid containing microvesicles in a method comprising the steps of:
  a) obtaining a biological fluid containing microvesicles,
  b) clarifying the biological fluid to remove cellular debris,
  c) precipitating the microvesicles by adding a precipitating agent to the clarified biological fluid,
  d) collecting the precipitated microvesicles and washing the material to remove the precipitating agent, and
  e) suspending the washed microvesicles in a solution for storage or subsequent use.

In one embodiment, the biological fluid is clarified by centrifugation. In an alternate embodiment, the biological fluid is clarified by filtration.

In one embodiment, the precipitated microvesicles are collected by centrifugation. In an alternate embodiment, the precipitated microvesicles are collected by filtration.

In one embodiment, microvesicles are isolated from a biological fluid containing microvesicles in a method comprising the steps of:

a) obtaining a biological fluid containing microvesicles,
b) clarifying the biological fluid to remove cellular debris,
c) precipitating the microvesicles by adding a precipitating agent to the clarified biological fluid,
d) collecting the precipitated microvesicles and washing the material to remove the precipitating agent,
e) suspending the washed microvesicles in a solution, and
f) processing the microvesicles to analyze the nucleic acid, carbohydrate, lipid, small molecules and/or protein content.

In one embodiment, the biological fluid is clarified by centrifugation. In an alternate embodiment, the biological fluid is clarified by filtration.

In one embodiment, the precipitated microvesicles are collected by centrifugation. In an alternate embodiment, the precipitated microvesicles are collected by filtration.

In one embodiment, the present invention provides reagents and kits to isolate microvesicles from biological fluids according to the methods of the present invention.

The biological fluid may be peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids.

The biological fluid may also be derived from the blastocyl cavity, umbilical cord blood, or maternal circulation, which may be of fetal or maternal origin. The biological fluid may also be derived from a tissue sample or biopsy.

The biological fluid may be derived from plant cells of cultures of plant cells. The biological fluid may be derived from yeast cells or cultures of yeast cells.

In one embodiment, the biological fluid is cell culture medium. In one embodiment, the cell culture medium is conditioned using tissues and/or cells prior to the isolation of microvesicles according to the methods of the present invention.

The term "conditioned" or "conditioned medium" refers to medium, wherein a population of cells or tissue, or combination thereof is grown, and the population of cells or tissue, or combination thereof contributes factors to the medium. In one such use, the population of cells or tissue, or combination thereof is removed from the medium, while the factors the cells produce remain. In one embodiment, the factors produced are microvesicles.

Medium may be conditioned via any suitable method selected by one of ordinary skill in the art. For example, medium may be cultured according to the methods described in EP1780267A2.

In one embodiment, microvesicles are isolated from cells or tissue that have been pre-treated prior to the isolation of the microvesicles. Pretreatment may include, for example, culture in a specific medium, a medium that contains at least one additive, growth factor, medium devoid of serum, or a combination thereof. Alternatively, pretreatment may comprise contacting cells or tissues with additives (e.g. interleukin, VEGF, inducers of transcription factors, transcription factors, hormones, neurotransmitters, pharmaceutical compounds, microRNA), transforming agents (e.g. liposome, viruses, transfected agents, etc.). Alternatively, pretreatment may comprise exposing cells or tissue to altered physical conditions (e.g. hypoxia, cold shock, heat shock).

In one embodiment, microvesicles are isolated from medium conditioned using cells or tissue that have been pre-treated prior to the isolation of the microvesicles. Pretreatment may include, for example, culture in a specific medium, a medium that contains at least one additive, growth factor, medium devoid of serum, or a combination thereof. Alternatively, pretreatment may comprise contacting cells or tissues with additives (e.g. interleukin, VEGF, inducers of transcription factors, transcription factors, hormones, neurotransmitters, pharmaceutical compounds, microRNA), transforming agents (e.g. liposome, viruses, transfected agents, etc.). Alternatively, pretreatment may comprise exposing cells or tissue to altered physical conditions (e.g. hypoxia, cold shock, heat shock).

In one embodiment, the biological fluid is an extract from a plant. In an alternate embodiment, the biological fluid is a cell culture medium from a culture of plant cells. In an alternate embodiment, the biological fluid is yeast extract. In an alternate embodiment, the biological fluid is a cell culture medium from a culture of yeast cells.

While the methods of the present invention may be carried out at any temperature, one of ordinary skill in the art can readily appreciate that certain biological fluids may degrade, and such degradation is reduced if the sample is maintained at a temperature below the temperature at which the biological fluid degrades. In one embodiment, the method of the present invention is carried out at 4° C. In an alternate embodiment, at least one step of the method of the present invention is carried out at 4° C.

In certain embodiments, the biological fluid may be diluted prior to being subjected to the methods of the present invention. Dilution may be required for viscous biological fluids, to reduce the viscosity of the sample, if the viscosity of the sample is too great to obtain an acceptable yield of microvesicles. The dilution may be a 1:2 dilution. Alternatively, the dilution may be a 1:3 dilution. Alternatively, the dilution may be a 1:4 dilution. Alternatively, the dilution may be a 1:5 dilution. Alternatively, the dilution may be a 1:6 dilution. Alternatively, the dilution may be a 1:7 dilution. Alternatively, the dilution may be a 1:8 dilution. Alternatively, the dilution may be a 1:9 dilution. Alternatively, the dilution may be a 1:10 dilution. Alternatively, the dilution may be a 1:20 dilution. Alternatively, the dilution may be a 1:30 dilution. Alternatively, the dilution may be a 1:40 dilution. Alternatively, the dilution may be a 1:50 dilution. Alternatively, the dilution may be a 1:60 dilution. Alternatively, the dilution may be a 1:70 dilution. Alternatively, the dilution may be a 1:80 dilution. Alternatively, the dilution may be a 1:90 dilution. Alternatively, the dilution may be a 1:100 dilution.

The biological fluid may be diluted with any diluent, provided the diluent does not affect the functional and/or structural integrity of the microvesicles. One of ordinary skill in the art may readily select a suitable diluent. Diluents may be, for example, phosphate buffered saline, cell culture medium, and the like.

In one embodiment, the biological fluid is clarified by the application of a centrifugal force to remove cellular debris.

The centrifugal force applied to the biological fluid is sufficient to remove any cells, lysed cells, tissue debris from the biological fluid, but the centrifugal force applied is insufficient in magnitude, duration, or both, to remove the microvesicles. The biological fluid may require dilution to facilitate the clarification.

The duration and magnitude of the centrifugal force used to clarify the biological fluid may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like. In one embodiment, a centrifugal force of 2000×g is applied to the biological fluid for 30 minutes.

The clarified biological fluid is contacted with a precipitation agent to precipitate the microvesicles. In one embodiment, the precipitation agent may be any agent that surrounds the microvesicles and displaces the water of solvation. Such precipitation agents may be selected from the group consisting of polyethylene glycol, dextran, and polysaccharides.

In an alternate embodiment, the precipitation agent may cause aggregation of the microvesicles.

In an alternate embodiment, the precipitation agent is selected from the group consisting of calcium ions, magnesium ions, sodium ions, ammonium ions, iron ions, organic solvents such as ammonium sulphate, and flocculating agents, such as alginate.

The clarified biological fluid is contacted with the precipitation agent for a period of time sufficient to precipitate the microvesicles. The period of time sufficient to precipitate the microvesicles may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like. In one embodiment, the period of time sufficient to precipitate the microvesicles is 6 hours.

In one embodiment, the clarified biological fluid is contacted with the precipitation agent for a period of time sufficient to precipitate the microvesicles at 4° C.

The concentration of the precipitation agent used to precipitate the microvesicles from a biological fluid may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like.

In one embodiment, the precipitation agent is polyethylene glycol. The molecular weight of polyethylene glycol used in the methods of the present invention may be from about 200 Da to about 10,000 Da. In one embodiment, the molecular weight of polyethylene glycol used in the methods of the present invention may be greater than 10,000 Da. The choice of molecular weight may be influenced by a variety of factors including, for example, the viscosity of the biological fluid, the desired purity of the microvesicles, the desired size of the microvesicles, the biological fluid used, and the like.

In one embodiment, the molecular weight of polyethylene glycol used in the methods of the present invention may be from about 200 Da to about 8,000 Da, or is approximately any of 200, 300, 400, 600, 1000, 1500, 4000, 6000, or 8000.

In one embodiment, the molecular weight of polyethylene glycol used in the methods of the present invention is about 6000 Da.

In one embodiment, the average molecular weight of polyethylene glycol used in the methods of the present invention is about 8000 Da.

The concentration of polyethylene glycol used in the methods of the present invention may be from about 0.5% w/v to about 100% w/v. The concentration of polyethylene glycol used in the methods of the present invention may be influenced by a variety of factors including, for example, the viscosity of the biological fluid, the desired purity of the microvesicles, the desired size of the microvesicles, the biological fluid used, and the like.

In certain embodiments, the polyethylene glycol is used in the concentration of the present invention at a concentration between about 5% and 25% w/v. In certain embodiments, the concentration is about 5%, 6%, 7%, 8%, 9%, 10%, 11%, 12%, 13%, 14%, or 15%, or a range between any two of these values.

In one embodiment, the concentration of polyethylene glycol used in the methods of the present invention is about 8.5% w/v.

In one embodiment, the concentration of polyethylene glycol used in the methods of the present invention is about 6% w/v.

In one embodiment, polyethylene glycol having an average molecular weight of 6000 Da is used, at a concentration of 8.5% w/v. In one embodiment, the polyethylene glycol is diluted in 0.4M sodium chloride.

In one embodiment, the concentration of the polyethylene glycol used in the methods of the present invention is inversely proportional to the average molecular weight of the polyethylene glycol. For example, in one embodiment, polyethylene glycol having an average molecular weight of 4000 Da is used, at a concentration of 20% w/v. In an alternate embodiment, polyethylene glycol having an average molecular weight of 8000 Da is used, at a concentration of 10% w/v. In an alternate embodiment, polyethylene glycol having an average molecular weight of 20000 Da is used, at a concentration of 4% w/v.

In one embodiment, the precipitated microvesicles are collected by the application of centrifugal force. The centrifugal force is sufficient and applied for a duration sufficient to cause the microvesicles to form a pellet, but insufficient to damage the microvesicles.

The duration and magnitude of the centrifugal force used to precipitate the microvesicles from a biological fluid may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like. In one embodiment, the precipitated microvesicles are collected by the application of a centrifugal force of 10000×g for 60 minutes.

The precipitated microvesicles may be washed with any liquid, provided the liquid does not affect the functional and/or structural integrity of the microvesicles. One of ordinary skill in the art may readily select a suitable liquid. Liquids may be, for example, phosphate buffered saline, cell culture medium, and the like.

In one embodiment, the washing step removes the precipitating agent. In one embodiment, the microvesicles are washed via centrifugal filtration, using a filtration device with a 100 kDa molecular weight cut off.

The isolated microvesicles may be suspended with any liquid, provided the liquid does not affect the functional and/or structural integrity of the microvesicles. One of ordinary skill in the art may readily select a suitable liquid. Liquids may be, for example, phosphate buffered saline, cell culture medium, and the like.

In one embodiment, the isolated microvesicles may be further processed. The further processing may be the isolation of a microvesicle of a specific size. Alternatively, the further processing may be the isolation of microvesicles of a particular size range. Alternatively, the further processing may be the isolation of a microvesicle of a particular molecular weight. Alternatively, the further processing may be the isolation of microvesicles of a particular molecular weight range. Alternatively, the further processing may be the isolation of a microvesicle exhibiting or containing a specific molecule.

In one embodiment, the microvesicles of the present invention are further processed to isolate a preparation of microvesicles having a size of about 2 nm to about 1000 nm as determined by electron microscopy. In an alternate embodiment, the microvesicles of the present invention are further processed to isolate a preparation of microvesicles having a size of about 2 nm to about 500 nm as determined by electron microscopy. In an alternate embodiment, the microvesicles of the present invention are further processed to isolate a preparation of microvesicles having a size of about 2 nm to about 400 nm as determined by electron microscopy. In an alternate embodiment, the microvesicles of the present invention are further processed to isolate a preparation of microvesicles having a size of about 2 nm to about 300 nm as determined by electron microscopy. In an alternate embodiment, the microvesicles of the present invention are further processed to isolate a preparation of microvesicles having a size of about 2 nm to about 200 nm as determined by electron microscopy. In an alternate embodiment, the microvesicles of the present invention are further processed to isolate a preparation of microvesicles having a size of about 2 nm to about 100 nm as determined by electron microscopy. In an alternate embodiment, the microvesicles of the present invention are further processed to isolate a preparation of microvesicles having a size of about 2 nm to about 50 nm as determined by electron microscopy. In an alternate embodiment, the microvesicles of the present invention are further processed to isolate a preparation of microvesicles having a size of about 2 nm to about 20 nm as determined by electron microscopy. In an alternate embodiment, the microvesicles of the present invention are further processed to isolate a preparation of microvesicles having a size of about 2 nm to about 10 nm as determined by electron microscopy.

In one embodiment, the subsequent purification is performed using a method selecting from the group consisting of immunoaffinity, HPLC, tangential flow filtration, phase separation/partitioning, and microfluidics.

In one embodiment, the isolated microvesicles are further processed to analyze the molecules exhibited on, or contained within the microvesicles. The molecules analyzed are selected from the group consisting of nucleic acid, carbohydrate, lipid, small molecules, ions, metabolites, protein, and combinations thereof.

Biological Fluid Comprising Cell Culture Medium Conditioned Using Cultured Cells:

In one embodiment, microvesicles are obtained from medium conditioned using cultured cells. Any cultured cell, or population of cells may be used in the methods of the present invention. The cells may be stem cells, primary cells, cell lines, tissue or organ explants, or any combination thereof. The cells may be allogeneic, autologous, or xenogeneic in origin.

In one embodiment, the cells are cells derived from bone-marrow aspirate. In one embodiment, the cells derived from bone marrow aspirate are bone marrow-derived mesenchymal stem cells. In one embodiment, the cells derived from bone marrow aspirate are mononuclear cells. In one embodiment, the cells derived from bone marrow aspirate are a mixture of mononuclear cells and bone marrow-derived mesenchymal stem cells.

In one embodiment, bone marrow-derived mesenchymal stem cells are isolated from bone marrow aspirate by culturing bone marrow aspirate in plastic tissue culture flasks for a period of time of up to about 4 days, followed by a wash to remove the non-adherent cells.

In one embodiment, mononuclear cells are isolated from bone marrow aspirate by low-density centrifugation using a ficoll gradient, and collecting the mononuclear cells at the interface.

In one embodiment, prior to isolation of microvesicles according to the methods of the present invention, the cells are cultured, grown or maintained at an appropriate temperature and gas mixture (typically, 37° C., 5% $CO_2$ for mammalian cells) in a cell incubator. Culture conditions vary widely for each cell type, and are readily determined by one of ordinary skill in the art.

In one embodiment, one, or more than one culture condition is varied. In one embodiment, this variation results in a different phenotype.

In one embodiment, where the cells require serum in their culture medium, to begin the microvesicle isolation procedure, the cell culture medium is supplemented with microvesicle-free serum and then added to the cells to be conditioned. The microvesicles are collected from the conditioned cell culture medium. Serum may be depleted by any suitable method, such as, for example, ultracentrifugation, filtration, precipitation, and the like. The choice of medium, serum concentration, and culture conditions are influenced by a variety of factors readily appreciated by one of ordinary skill in the art, including, for example, the cell type being cultured, the desired purity of the microvesicles, the desired phenotype of the cultured cell, and the like. In one embodiment, the cell culture medium that is conditioned for the microvesicle isolation procedure is the same type of cell culture medium that the cells were grown in, prior to the microvesicle isolation procedure.

In one embodiment, to begin the microvesicle isolation procedure, the cell culture medium is removed, and serum-free medium is added to the cells to be conditioned. The microvesicles are then collected from the conditioned serum free medium. The choice of medium, and culture conditions are influenced by a variety of factors readily appreciated by one of ordinary skill in the art, including, for example, the cell type being cultured, the desired purity of the microvesicles, the desired phenotype of the cultured cell, and the like. In one embodiment, the serum-free medium is supplemented with at least one additional factor that promotes or enhances the survival of the cells in the serum free medium. Such factor may, for example, provide trophic support to the cells, inhibit, or prevent apoptosis of the cells.

The cells are cultured in the culture medium for a period of time sufficient to allow the cells to secrete microvesicles into the culture medium. The period of time sufficient to allow the cells to secrete microvesicles into the culture medium is influenced by a variety of factors readily appreciated by one of ordinary skill in the art, including, for example, the cell type being cultured, the desired purity of the microvesicles, the desired phenotype of the cultured cell, desired yield of microvesicles, and the like.

The microvesicles are then removed from the culture medium by the methods of the present invention.

In one embodiment, prior to the microvesicle isolation procedure, the cells are treated with at least one agent selected from the group consisting of an anti-inflammatory compound, an anti-apoptotic compound, an inhibitor of fibrosis, a compound that is capable of enhancing angiogenesis, an immunosuppressive compound, a compound that promotes survival of the cells, a chemotherapeutic, a compound capable of enhancing cellular migration, a neurogenic compound, and a growth factor.

In one embodiment, while the cells are being cultured in the medium from which the microvesicles are collected, the cells are treated with at least one agent selected from the group consisting of an anti-inflammatory compound, an anti-apoptotic compound, an inhibitor of fibrosis, a compound that is capable of enhancing angiogenesis, an immunosuppressive compound, a compound that promotes survival of the cells, and a growth factor.

In one embodiment, the anti-inflammatory compound may be selected from the compounds disclosed in U.S. Pat. No. 6,509,369.

In one embodiment, the anti-apoptotic compound may be selected from the compounds disclosed in U.S. Pat. No. 6,793,945.

In one embodiment, the inhibitor of fibrosis may be selected from the compounds disclosed in U.S. Pat. No. 6,331,298.

In one embodiment, the compound that is capable of enhancing angiogenesis may be selected from the compounds disclosed in U.S. Patent Application 2004/0220393 or U.S. Patent Application 2004/0209901.

In one embodiment, the immunosuppressive compound may be selected from the compounds disclosed in U.S. Patent Application 2004/0171623.

In one embodiment, the compound that promotes survival of the cells may be selected from the compounds disclosed in U.S. Patent Application 2010/0104542.

In one embodiment, the growth factor may be at least one molecule selected from the group consisting of members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, -AB, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-1 (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, and MAPK inhibitors, such as, for example, compounds disclosed in U.S. Patent Application 2004/0209901 and U.S. Patent Application 2004/0132729.

In one embodiment, microvesicles are isolated from a biological fluid comprising cell culture medium conditioned using a culture of bone marrow-derived mesenchymal stem cells comprising the steps of:

a) obtaining a population of bone marrow-derived mesenchymal stem cells and seeding flasks at a 1:4 dilution of cells,
b) culturing the cells in medium until the cells are 80 to 90% confluent,
c) removing and clarifying the medium to remove cellular debris,
d) precipitating the microvesicles by adding a precipitating agent to the clarified culture medium,
e) collecting the precipitated microvesicles and washing the material to remove the precipitating agent, and
f) suspending the washed microvesicles in a solution for storage or subsequent use.

In one embodiment, microvesicles are isolated from a biological fluid comprising cell culture medium conditioned using a culture of bone marrow-derived mononuclear cells comprising the steps of:

a) obtaining a population of bone marrow-derived mononuclear cells and seeding flasks at a 1:4 dilution of cells,
b) culturing the cells in medium until the cells are 80 to 90% confluent,
c) removing and clarifying the medium to remove cellular debris,
d) precipitating the microvesicles by adding a precipitating agent to the clarified culture medium,
e) collecting the precipitated microvesicles and washing the material to remove the precipitating agent, and
f) suspending the washed microvesicles in a solution for storage or subsequent use.

In one embodiment, the bone marrow-derived mesenchymal stem cells are cultured in medium comprising α-MEM supplemented with 20% fetal bovine serum and 1% penicillin/streptomycin/glutamine at 37° C. in 95% humidified air and 5% $CO_2$.

In one embodiment, the bone marrow-derived mononuclear cells are cultured in medium comprising α-MEM supplemented with 20% fetal bovine serum and 1% penicillin/streptomycin/glutamine at 37° C. in 95% humidified air and 5% $CO_2$.

In one embodiment, the medium is clarified by centrifugation.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

Biological Fluid Comprising Plasma:

In one embodiment, microvesicles are obtained from plasma. The plasma may be obtained from a healthy individual, or, alternatively, from an individual with a particular disease phenotype.

In one embodiment, microvesicles are isolated from a biological fluid comprising plasma comprising the steps of:

a) obtaining plasma and diluting the plasma with cell culture medium,
b) precipitating the microvesicles by adding a precipitating agent to the diluted plasma,
c) collecting the precipitated microvesicles and washing the material to remove the precipitating agent, and d) suspending the washed microvesicles in a solution for storage or subsequent use.

In one embodiment, the plasma is diluted 1:10 with culture medium.

In one embodiment, the culture medium is α-MEM.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

Biological Fluid Comprising Bone Marrow Aspirate:

In one embodiment, microvesicles are obtained from bone marrow aspirate. In one embodiment, microvesicles are obtained from the cellular fraction of the bone marrow aspirate. In one embodiment, microvesicles are obtained from the acellular fraction of the bone marrow aspirate.

In one embodiment, microvesicles are obtained from cells cultured from bone marrow aspirate. In one embodiment, the cells cultured from bone marrow aspirate are used to condition cell culture medium, from which the microvesicles are isolated.

In one embodiment, microvesicles are isolated from a biological fluid comprising bone marrow aspirate comprising the steps of:
a) obtaining bone marrow aspirate and separating the bone marrow aspirate into an acellular portion and a cellular portion,
b) diluting the acellular portion,
c) clarifying the diluted acellular portion to remove cellular debris,
d) precipitating the microvesicles in the acellular portion by adding a precipitating agent to the diluted acellular portion,
e) collecting the precipitated microvesicles and washing the material to remove the precipitating agent, and
f) suspending the washed microvesicles in a solution for storage or subsequent use.

In one embodiment, the acellular portion is diluted 1:10 with culture medium.

In one embodiment, the culture medium is α-MEM.

In one embodiment, the diluted acellular portion is clarified by centrifugation.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

In one embodiment the cellular portion is further processed to isolate and collect cells. In one embodiment, the cellular portion is further processed to isolate and collect bone marrow-derived mesenchymal stem cells. In one embodiment, the cellular portion is further processed to isolate and collect bone marrow-derived mononuclear cells. In one embodiment, the cellular portion is used to condition medium, from which microvesicles may later be derived.

In one embodiment, microvesicles are isolated from the cellular portion. The cellular portion may be incubated for a period of time prior to the isolation of the microvesicles. Alternatively, the microvesicles may be isolated from the cellular portion immediately after the cellular portion is collected.

In one embodiment, the cellular portion is also treated with at least one agent selected from the group consisting of an anti-inflammatory compound, an anti-apoptotic compound, an inhibitor of fibrosis, a compound that is capable of enhancing angiogenesis, an immunosuppressive compound, a compound that promotes survival of the cells, a chemotherapeutic, a compound capable of enhancing cellular migration, a neurogenic compound, and a growth factor.

In one embodiment, the anti-inflammatory compound may be selected from the compounds disclosed in U.S. Pat. No. 6,509,369.

In one embodiment, the anti-apoptotic compound may be selected from the compounds disclosed in U.S. Pat. No. 6,793,945.

In one embodiment, the inhibitor of fibrosis may be selected from the compounds disclosed in U.S. Pat. No. 6,331,298.

In one embodiment, the compound that is capable of enhancing angiogenesis may be selected from the compounds disclosed in U.S. Patent Application 2004/0220393 or U.S. Patent Application 2004/0209901.

In one embodiment, the immunosuppressive compound may be selected from the compounds disclosed in U.S. Patent Application 2004/0171623.

In one embodiment, the compound that promotes survival of the cells may be selected from the compounds disclosed in U.S. Patent Application 2010/0104542.

In one embodiment, the growth factor may be at least one molecule selected from the group consisting of members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, -AB, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-1 (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, and MAPK inhibitors, such as, for example, compounds disclosed in U.S. Patent Application 2004/0209901 and U.S. Patent Application 2004/0132729.

In one embodiment, the cellular portion is cultured under hypoxic conditions.

In one embodiment, the cellular portion is heat-shocked.

Biological Fluid Comprising Urine:

In one embodiment, microvesicles are obtained from urine. The urine may be obtained from a healthy individual, or, alternatively, from an individual with a particular disease phenotype.

In one embodiment, microvesicles are isolated from a biological fluid comprising urine comprising the steps of:
a) obtaining a urine sample,
b) clarifying the urine to remove cellular debris, c) precipitating the microvesicles by adding a precipitating agent to the clarified urine,
d) collecting the precipitated microvesicles and washing the material to remove the precipitating agent, and
e) suspending the washed microvesicles in a solution for storage or subsequent use.

In one embodiment, the urine is clarified by centrifugation.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

In an alternate embodiment of the present invention, the biological fluids are clarified by filtration. In an alternate embodiment, the precipitated microvesicles are collected by filtration. In an alternate embodiment, the biological fluids are clarified and the precipitated microvesicles are collected by filtration.

In certain embodiments, filtration of either the biological fluid, and/or the precipitated microvesicles required the application of an external force. The external force may be gravity, either normal gravity or centrifugal force. Alternatively, the external force may be suction.

In one embodiment, the present embodiment provides an apparatus to facilitate the clarification of the biological fluid by filtration. In one embodiment, the present invention provides an apparatus to facilitate collection of the precipitated microvesicles by filtration. In one embodiment, the present invention provides an apparatus that facilitates the clarification of the biological fluid and the collection of the precipitated microvesicles by filtration. In one embodiment, the apparatus also washes the microvesicles.

Figure 4:
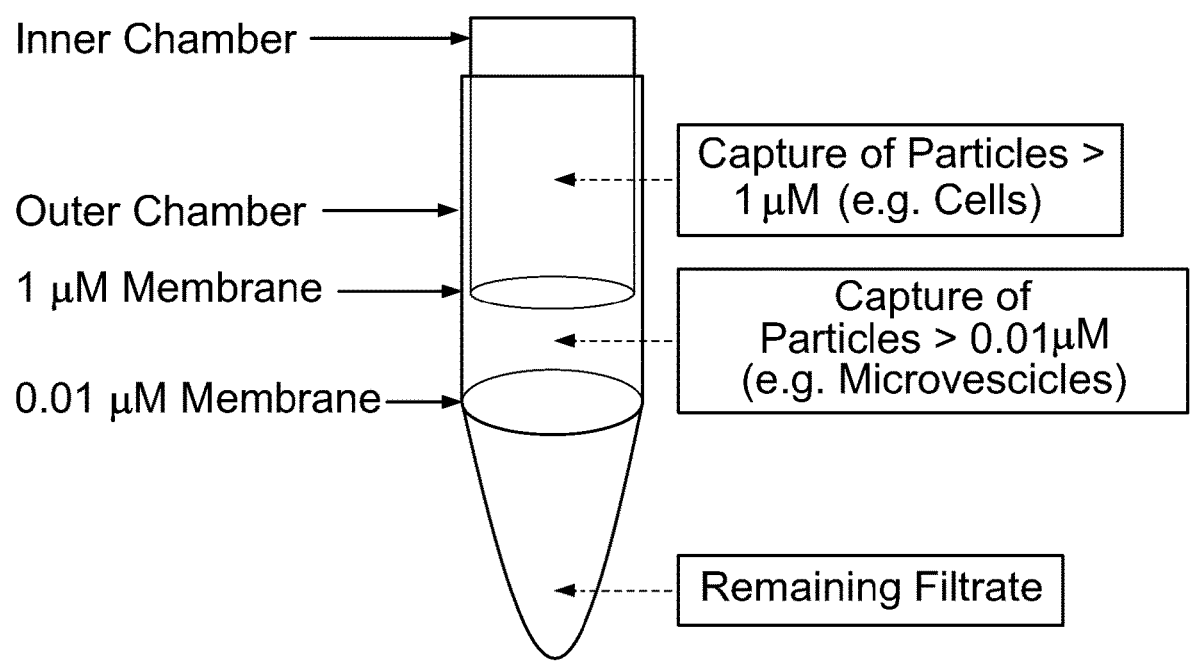
FIG. 4 shows one embodiment of an apparatus of the present invention that facilitates the clarification of the biological fluid and the collection of the precipitated microvesicles by filtration.
Figure 5B:
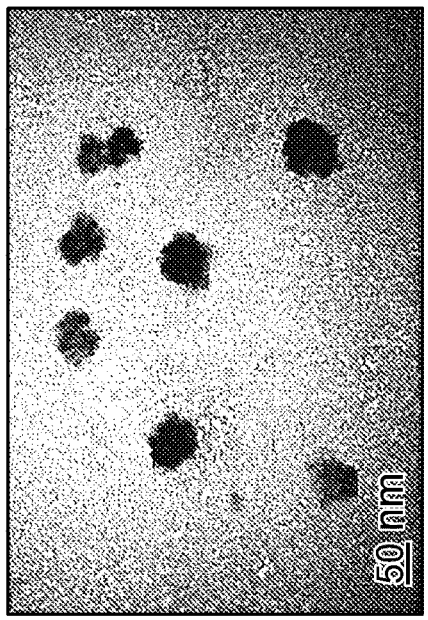
FIG. 5 shows electron micrographs of microvesicles derived from medium conditioned using human bone marrow-derived mesenchymal stem cells isolated by the ultracentrifuge method described in Example 1 (panels A & B) and isolated according to the methods of the present invention (panels C &D) at the magnifications shown in the panels.
Figure 5D:
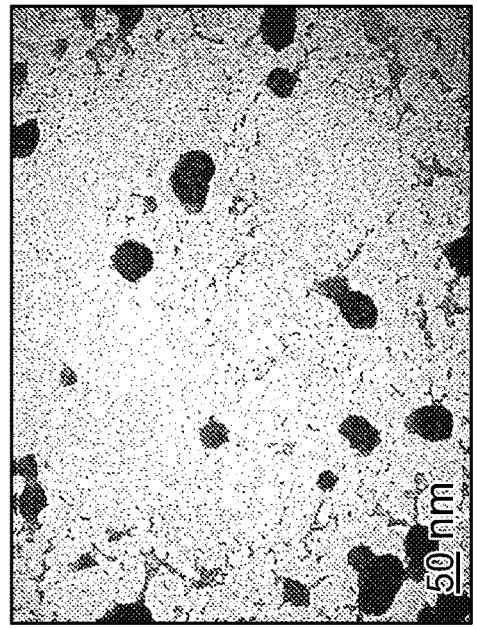
Figure 5A:
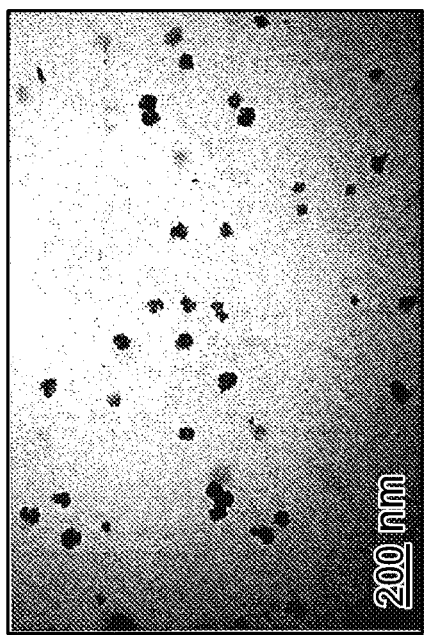
Figure 5C:
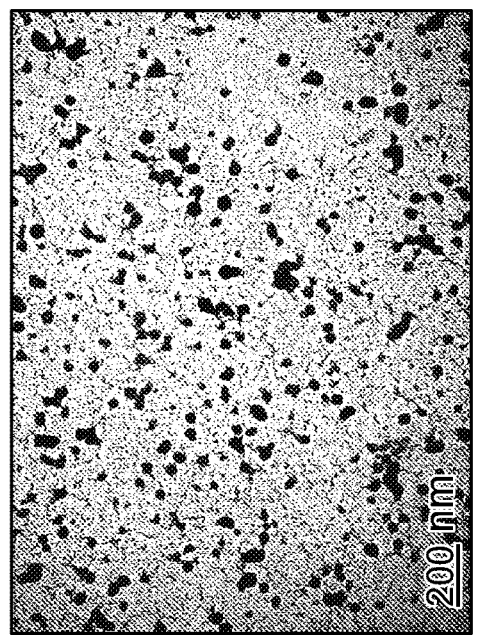
Figure 6B:
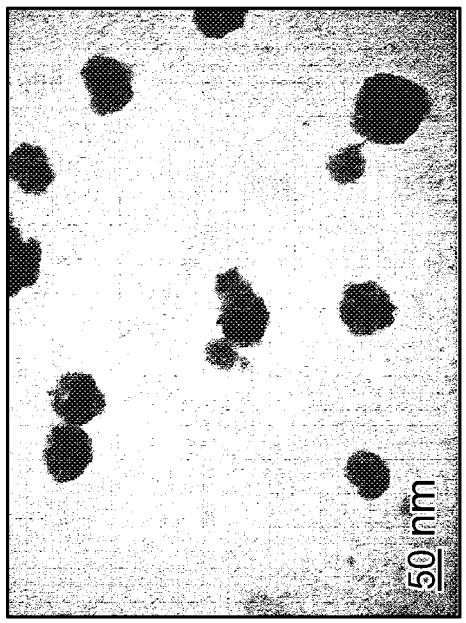
FIG. 6 shows electron micrographs of microvesicles derived from medium conditioned using porcine bone marrow-derived mesenchymal stem cells isolated by the ultracentrifuge method described in Example 1 (panels A & B) and isolated according to the methods of the present invention (panels C &D) at the magnifications shown in the panels.
Figure 6D:
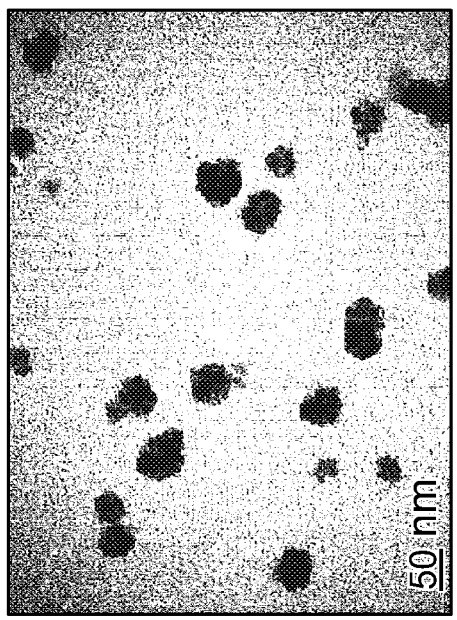
Figure 6A:
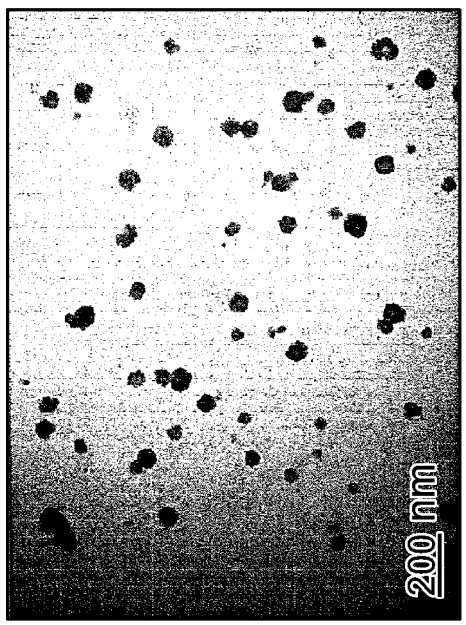
Figure 6C:
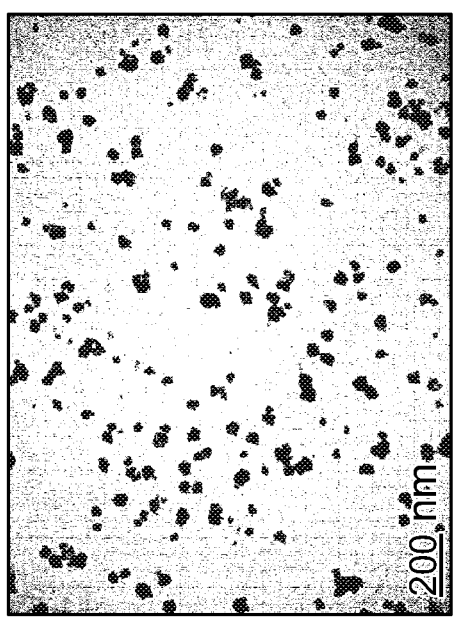
Figure 7A:
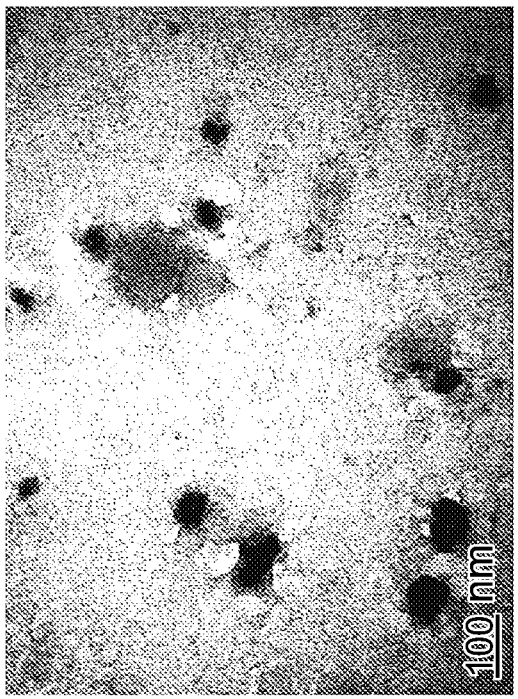
FIG. 7 shows electron micrographs of microvesicles derived from medium conditioned using murine bone marrow-derived mesenchymal stem cells isolated by the ultracentrifuge method described in Example 1 (panels A & B) and isolated according to the methods of the present invention (panels C &D) at the magnifications shown in the panels.
Figure 7B:
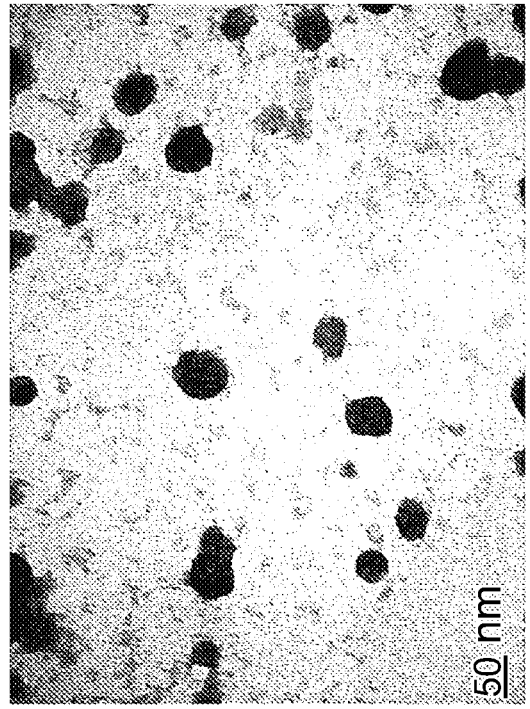
Figure 7C:
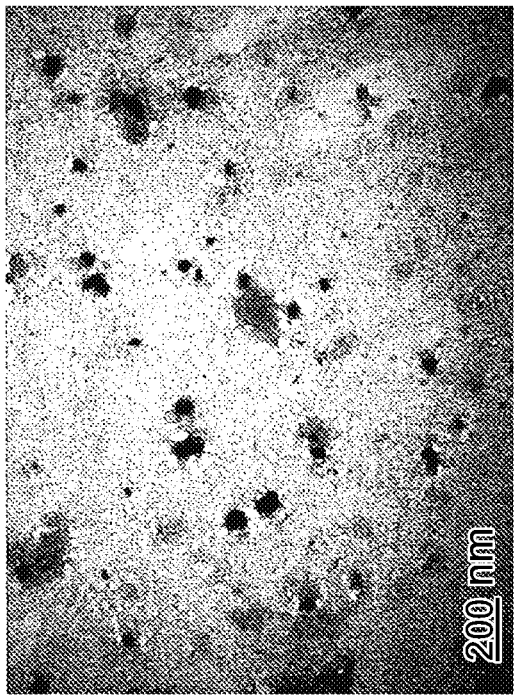
Figure 7D:
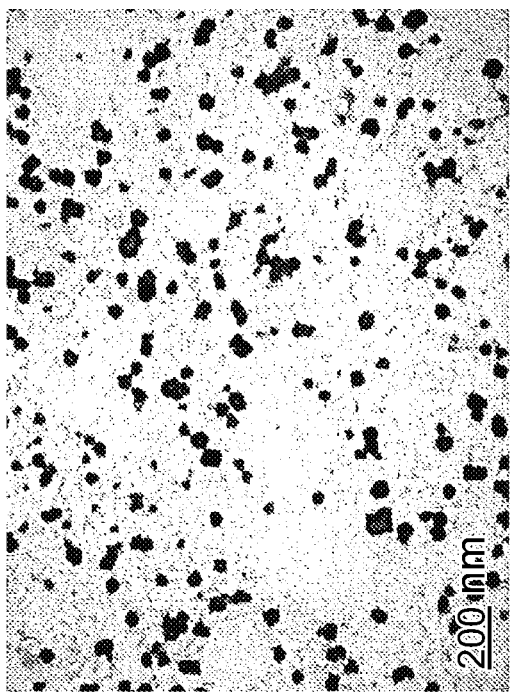

In one embodiment, the apparatus is the apparatus shown in FIG. 4. In this embodiment, the biological fluid is added to the inner chamber. The inner chamber has a first filter with a pore size that enables the microvesicles to pass, while retaining any particle with a size greater than a microvesicle in the inner chamber. In one embodiment, the pore size of the filter of the inner chamber is 1 µm. In this embodiment, when the biological fluid passed from the inner chamber through the filter, particles greater than 1 µm are retained in the inner chamber, and all other particles collect in the region between the bottom of the inner chamber and a second filter.

The second filter has a pore size that does not allow microvesicles to pass. In one embodiment, the pore size of the second filter of the inner chamber is 0.01 µm. In this embodiment, when the biological fluid passed through the second filter, the microvesicles are retained in the region between the bottom of the inner chamber and the second filter, and all remaining particles and fluid collect in the bottom of the apparatus.

One of ordinary skill in the art can readily appreciate that the apparatus can have more than two filters, of varying pore sizes to select for microvesicles of desired sizes, for example.

In one embodiment, a precipitating agent is added to the biological fluid in the inner chamber. In one embodiment, a precipitating agent is added to the filtrate after it has passed through the first filter.

The filter membranes utilized by the apparatus of the present invention may be made from any suitable material, provided the filter membrane does not react with the biological fluid, or bind with components within the biological fluid. For example, the filter membranes may be made from a low bind material, such as, for example, polyethersulfone, nylon6, polytetrafluoroethylene, polypropylene, zeta modified glass microfiber, cellulose nitrate, cellulose acetate, polyvinylidene fluoride, regenerated cellulose.

The Microvesicles of the Present Invention

In one embodiment, the microvesicles of the present invention have a size of about 2 nm to about 5000 nm as determined by electron microscopy. In an alternate embodiment, the microvesicles of the present invention have a size of about 2 nm to about 1000 nm as determined by electron microscopy. In an alternate embodiment, the microvesicles of the present invention have a size of about 2 nm to about 500 nm as determined by electron microscopy. In an alternate embodiment, the microvesicles of the present invention have a size of about 2 nm to about 400 nm as determined by electron microscopy. In an alternate embodiment, the microvesicles of the present invention have a size of about 2 nm to about 300 nm as determined by electron microscopy. In an alternate embodiment, the microvesicles of the present invention have a size of about 2 nm to about 200 nm as determined by electron microscopy. In an alternate embodiment, the microvesicles of the present invention have a size of about 2 nm to about 100 nm as determined by electron microscopy. In an alternate embodiment, the microvesicles of the present invention have a size of about 2 nm to about 50 nm as determined by electron microscopy. In an alternate embodiment, the microvesicles of the present invention have a size of about 2 nm to about 20 nm as determined by electron microscopy. In an alternate embodiment, the microvesicles of the present invention have a size of about 2 nm to about 10 nm as determined by electron microscopy.

In one embodiment, the microvesicles of the present invention have a molecular weight of at least 100 kDa.

Microvesicles isolated according to the methods of the present invention may be used for therapies. Alternatively, microvesicles isolated according to the methods of the present invention may be used for diagnostic tests. Alternatively, the microvesicles of the present invention may be used to alter or engineer cells or tissues. In the case where the microvesicles of the present invention are used to alter or engineer cells or tissues, the microvesicles may be loaded, labeled with RNA, DNA, lipids, carbohydrates, protein, drugs, small molecules, metabolites, or combinations thereof, that will alter or engineer a cell or tissue. Alternatively, the microvesicles may be isolated from cells or tissues that express and/or contain the RNA, DNA, lipids, carbohydrates, protein, drugs, small molecules, metabolites, or combinations thereof.

Use of the Microvesicles of the Present Invention in Diagnostic Tests

The microvesicles of the present invention can be used in a diagnostic test that detects biomarkers that identify particular phenotypes such as, for example, a condition or disease, or the stage or progression of a disease. Biomarkers or markers from cell-of-origin specific microvesicles can be used to determine treatment regimens for diseases, conditions, disease stages, and stages of a condition, and can also be used to determine treatment efficacy. Markers from cell-of-origin specific microvesicles can also be used to identify conditions of diseases of unknown origin.

As used herein, the term "biomarker" refers to an indicator of a biological state. It is a characteristic that is objectively measured and evaluated as an indicator of normal biological processes, pathogenic processes, or pharmacologic responses to a therapeutic intervention. One or more biomarkers of microvesicle can be assessed for characterizing a phenotype. The biomarker can be a metabolite, a nucleic acid, peptide, protein, lipid, antigen, carbohydrate or proteoglycan, such as DNA or RNA. The RNA can be mRNA, miRNA, snoRNA, snRNA, rRNAs, tRNAs, siRNA, hnRNA, or shRNA.

A phenotype in a subject can be characterized by obtaining a biological sample from the subject and analyzing one or more microvesicles from the sample. For example, characterizing a phenotype for a subject or individual may include detecting a disease or condition (including pre-symptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The products and processes described herein allow assessment of a subject on an individual basis, which can provide benefits of more efficient and economical decisions in treatment.

The phenotype can be any phenotype listed in U.S. Pat. No. 7,897,356. The phenotype can be a tumor, neoplasm, or cancer. A cancer detected or assessed by products or processes described herein includes, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma. The phenotype may also be a premalignant condition, such as Barrett's Esophagus.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, graft versus host disease, Primary Sclerosing Cholangitis, or sepsis.

The phenotype can also be a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neuropsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also be an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. Viral proteins, such as HIV or HCV-like particles can be assessed in an exosome, to characterize a viral condition.

The phenotype can also be a perinatal or pregnancy related condition (e.g. preeclampsia or preterm birth), metabolic disease or condition, such as a metabolic disease or condition associated with iron metabolism. The metabolic disease or condition can also be diabetes, inflammation, or a perinatal condition.

The phenotype may be detected via any suitable assay method, such as, for example, western blots, ELISA, PCR, and the like. The assay methods may be combined to perform multiplexed analysis of more than one phenotype. Examples of assay methods that may be applied to the microvesicles of the present invention are disclosed in PCT Applications WO2009092386A3 and WO2012108842A1.

In the case where the biomarker is RNA, the RNA may be isolated from the microvesicles of the present invention by the methods disclosed in U.S. Pat. No. 8,021,847.

In one embodiment, the microvesicles of the present invention are utilized in a diagnostic test for the diseases disclosed in U.S. Pat. No. 7,897,356.

In one embodiment, the microvesicles of the present invention are utilized in a diagnostic test for cancer according to the methods disclosed in U.S. Pat. No. 8,211,653.

In one embodiment, the microvesicles of the present invention are utilized in a diagnostic test for cancer according to the methods disclosed in U.S. Pat. No. 8,216,784.

In one embodiment, the microvesicles of the present invention are utilized in a diagnostic test for prostate cancer according to the methods disclosed in U.S. Pat. No. 8,278,059.

In one embodiment, the microvesicles of the present invention are utilized in a diagnostic test for the prognosis for cancer survival according to the methods disclosed in U.S. Pat. No. 8,343,725.

In one embodiment, the microvesicles of the present invention are utilized in a diagnostic test for the prognosis for cancer survival according to the methods disclosed in U.S. Pat. No. 8,349,568.

In one embodiment, the microvesicles of the present invention are utilized in a diagnostic test for acute lymphomic leukemia according to the methods disclosed in U.S. Pat. No. 8,349,560.

In one embodiment, the microvesicles of the present invention are utilized in a diagnostic test for acute lymphomic leukemia according to the methods disclosed in U.S. Pat. No. 8,349,561.

In one embodiment, the microvesicles of the present invention are utilized in a diagnostic test for hepatitis C virus. In one embodiment, hepatitis C viral RNA is extracted from the microvesicles of the present invention according to the methods described in U.S. Pat. No. 7,807,438 to test for the presence of hepatitis C virus in a patient.

In one embodiment, the microvesicles of the present invention are utilized in a diagnostic test for determining the response of a patient to cancer therapy according to the methods disclosed in U.S. Pat. No. 8,349,574.

In one embodiment, the microvesicles of the present invention are utilized in a diagnostic test for diagnosing malignant tumors according to the methods disclosed in U.S. Patent Application US20120058492A1.

In one embodiment, the microvesicles of the present invention are utilized in a diagnostic test for diagnosing cancer or adverse pregnancy outcome according to the methods disclosed in U.S. Patent Application US20120238467A1.

In one embodiment, the microvesicles of the present invention are utilized in a diagnostic test for HIV in urine according to the methods disclosed in U.S. Patent Application US20120214151A1.

In one embodiment, the microvesicles of the present invention are utilized in a diagnostic test for cardiovascular events according to the methods disclosed in U.S. Patent Application US20120309041A1.

In one embodiment, the microvesicles of the present invention are utilized in a diagnostic test for cardiovascular events according to the methods disclosed in PCT Application WO2012110099A1.

In one embodiment, the microvesicles of the present invention are utilized in a diagnostic test for cardiovascular events according to the methods disclosed in PCT Application WO2012126531A1.

In one embodiment, the microvesicles of the present invention are utilized in a diagnostic test for cardiovascular events according to the methods disclosed in PCT Application WO2013110253A3.

In one embodiment, the microvesicles of the present invention are utilized in a diagnostic test for melanoma according to the methods disclosed in PCT Application WO2012135844A2.

In one embodiment, the microvesicles of the present invention are utilized in a diagnostic test for metastatic melanoma by testing microvesicles isolated according to the methods of the present invention for the presence of the biomarker BRAF. The presence of BRAF may be determined via western blot, or, alternatively, by PCR. In one embodiment, the metastatic melanoma test is capable of detecting wild type and malignant BRAF. In one embodiment, the metastatic melanoma test is capable of detecting splice variants of the malignant BRAF.

Figure 3:
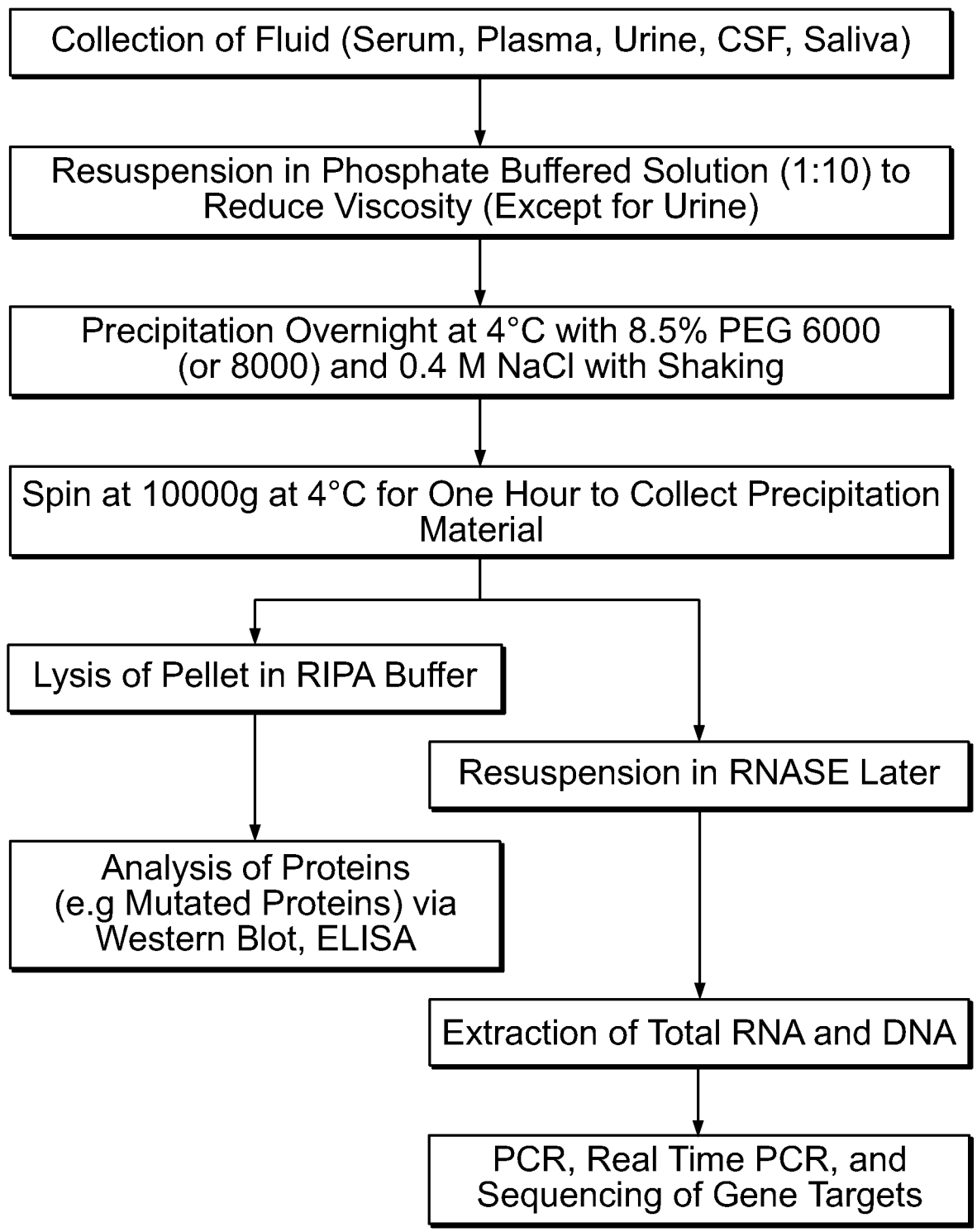
FIG. 3 shows an alternate embodiment of a microvesicle isolation method of the present invention.

In one embodiment, the microvesicles that are utilized in the diagnostic test for metastatic melanoma are isolated using a method comprising the steps outlined in FIG. 3.

In one embodiment, microvesicles are obtained from a patient wishing to be diagnosed for the presence of metastatic melanoma. In one embodiment, the microvesicles are obtained from the patient's plasma.

In one embodiment, the presence of metastatic melanoma is determined via PCR, using one of the two primer sets below:

```
Sequence 1:
Forward:
AGACCTCACAGTAAAAATAGGTGA

Reverse:
CTGATGGGACCCACTCCATC

Amplicon length: 70

Sequence 2:
Forward:
GAAGACCTCACAGTAAAAATAGGTG

Reverse:
CTGATGGGACCCACTCCATC

Amplicon length: 82
```

In another embodiment, the presence of metastatic melanoma is determined via western blot, using the mouse anti-BRAF V600E antibody (NewEast Biosciences, Malvern, Pa.).

Use of the Microvesicles of the Present Invention in Therapies

The microvesicles of the present invention can be used as a therapy to treat a disease.

In one embodiment, the microvesicles of the present invention are used as vaccines according to the methods described in U.S. Patent Application US20030198642A1.

In one embodiment, the microvesicles of the present invention are used to modulate or suppress a patient's immune response according to the methods described in U.S. Patent Application US20060116321A1.

In one embodiment, the microvesicles of the present invention are used to modulate or suppress a patient's immune response according to the methods described in PCT Patent Application WO06007529A3.

In one embodiment, the microvesicles of the present invention are used to modulate or suppress a patient's immune response according to the methods described in PCT Patent Application WO2007103572A3.

In one embodiment, the microvesicles of the present invention are used to modulate or suppress a patient's immune response according to the methods described in U.S. Pat. No. 8,288,172.

In one embodiment, the microvesicles of the present invention are used as a therapy for cancer according to the methods described in PCT Patent Application WO2011000551A1.

In one embodiment, the microvesicles of the present invention are used as a therapy for cancer or an inflammatory disease according to the methods described in U.S. Patent Application US20120315324A1.

In one embodiment, the microvesicles of the present invention are used as a therapy for vascular injury according to the methods described in U.S. Pat. No. 8,343,485.

In one embodiment, the microvesicles of the present invention are used to deliver molecules to cells. The delivery of molecules may be useful in treating or preventing a disease. In one embodiment, the delivery is according to the methods described in PCT Application WO04014954A1. In an alternate embodiment, the delivery is according to the methods described in PCT Application WO2007126386A1. In an alternate embodiment, the delivery is according to the methods described in PCT Application WO2009115561A1. In an alternate embodiment, the delivery is according to the methods described in PCT Application WO2010119256A1.

In one embodiment, the microvesicles of the present invention are used to promote or enhance wound healing. In one embodiment, the wound is a full-thickness burn. In one embodiment, the wound is a second-degree burn.

In one embodiment, the microvesicles of the present invention are used to promote or enhance angiogenesis in a patient.

In one embodiment, the microvesicles of the present invention are used to promote or enhance neuronal regeneration in a patient.

In one embodiment, the microvesicles of the present invention are used to reduce scar formation in a patient.

In one embodiment, the microvesicles of the present invention are used to reduce wrinkle formation in the skin of a patient.

In one embodiment, the microvesicles of the present invention are used to orchestrate complex tissue regeneration in a patient.

In one embodiment, the present invention provides an isolated preparation of microvesicles that can promote functional regeneration and organization of complex tissue structures. In one embodiment the present invention provides an isolated preparation of microvesicles that can regenerate hematopoietic tissue in a patient with aplastic anemia. In one embodiment the present invention provides an isolated preparation of microvesicles that can regenerate at least one tissue in a patient with diseased, damages or missing skin selected from the group consisting of: epithelial tissue, stromal tissue, nerve tissue, vascular tissue and adnexal structures. In one embodiment, the present invention provides an isolated preparation of microvesicles that can regenerate tissue and/or cells from all three germ layers.

In one embodiment, the present invention provides an isolated preparation of microvesicles that is used to modulate the immune system of a patient.

In one embodiment, the present invention provides an isolated preparation of microvesicles that enhances the survival of tissue or cells that is transplanted into a patient. In one embodiment, the patient is treated with the isolated preparation of microvesicles prior to receiving the transplanted tissue or cells. In an alternate embodiment, the patient is treated with the isolated preparation of microvesicles after receiving the transplanted tissue or cells. In an alternate embodiment, the tissue or cells is treated with the isolated preparation of microvesicles. In one embodiment, the tissue or cells is treated with the isolated preparation of microvesicles prior to transplantation.

In one embodiment, the present invention provides an isolated preparation of microvesicles containing at least one molecule selected from the group consisting of RNA, DNA, lipid, carbohydrate, metabolite, protein, and combination thereof from a host cell. In one embodiment, the host cell is engineered to express at least one molecule selected from the group consisting of RNA, DNA, lipid, carbohydrate, metabolite, protein, and combination thereof. In one embodiment, the isolated preparation of microvesicles containing at least one molecule selected from the group consisting of RNA, DNA, lipid, carbohydrate, metabolite, protein, and combination thereof from a host cell is used as a therapeutic agent.

The present invention is further illustrated, but not limited by, the following examples.

EXAMPLES

Example 1: Isolation of Microvesicles from Cell Culture Medium by Ultracentrifugation This example illustrates the typical method by which microvesicles are isolated from cell culture medium, or any biological fluid. An outline of the method to isolate microvesicles from cell culture medium is shown in FIG. 1. In summary, the cells are cultured in medium supplemented with microvesicle-free serum (the serum may be depleted of microvesicles by ultracentrifugation, filtration, precipitation, etc.). After culturing the cells for a period of time, the medium is removed and transferred to conical tubes and centrifuged at 400×g for 10 minutes at 4° C. to pellet the cells. Next, the supernatant is transferred to new conical tubes and centrifuged at 2000×g for 30 minutes at 4° C. to further remove cells and cell debris. This may be followed by another centrifugation step (e.g. 10000×g for 30 minutes to further deplete cellular debris and/or remove larger microvesicles). The resultant supernatant is transferred to ultracentrifuge tubes, weighed to ensure equal weight and ultracentrifuged at 70000+×g for 70 minutes at 4° C. to pellet the microvesicles.

This supernatant is subsequently discarded and the pellet is resuspended in ice cold PBS. The solution is ultracentrifuged at 70000+×g for 70 minutes at 4° C. to pellet the microvesicles. The microvesicle enriched pellet is resuspended in a small volume (approximately 50-100 μl) of an appropriate buffer (e.g. PBS).

Figure 2:
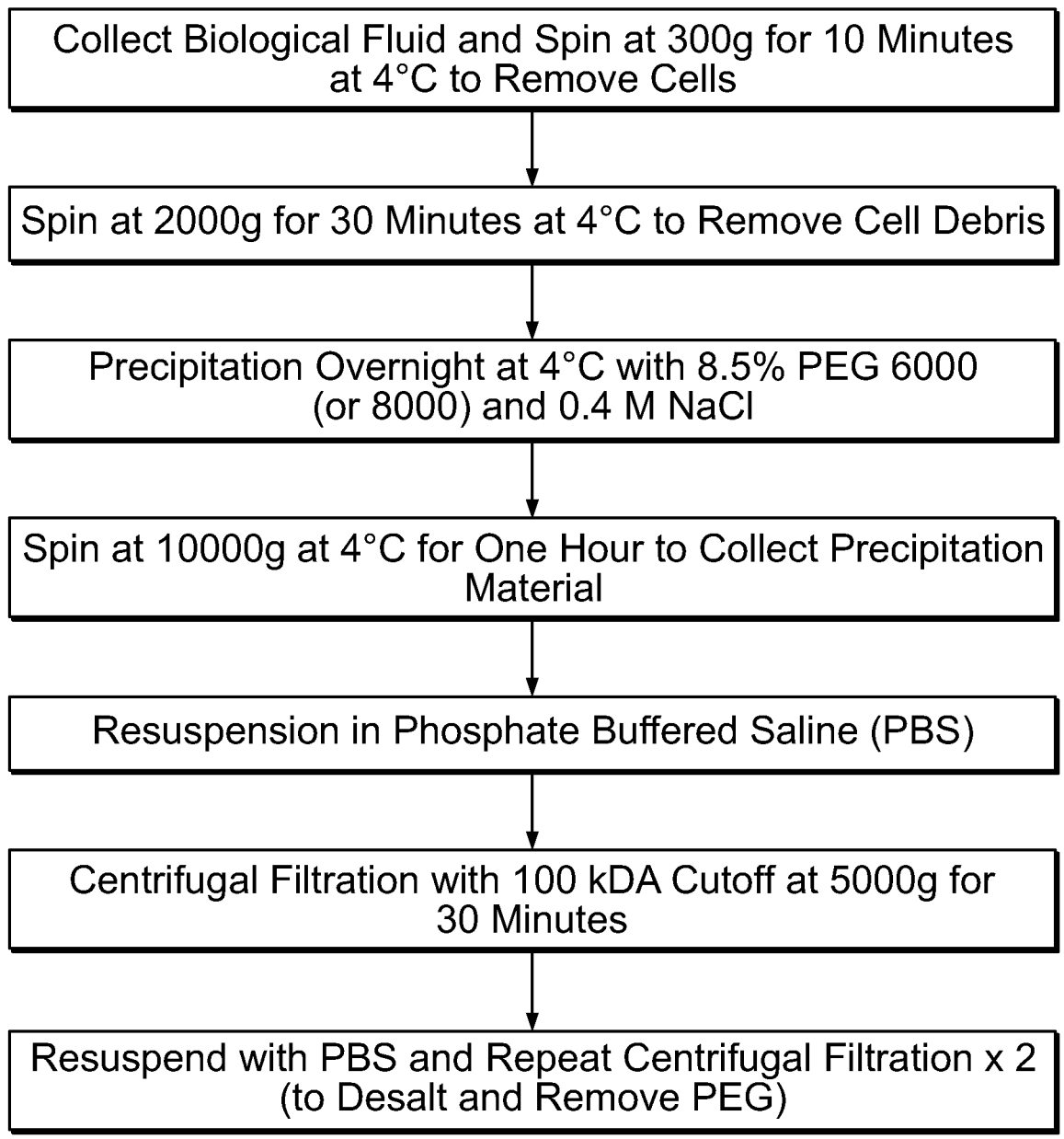
FIG. 2 shows one embodiment of a microvesicle isolation method of the present invention.

Example 2: Isolation of Microvesicles from Cell Culture Medium by the Methods of the Present Invention This example illustrates how microvesicles are isolated from cell culture medium by the methods of the present invention. An outline of the method to isolate microvesicles from medium that has cultured cells is shown in FIGS. 2 and 3. In summary, the cells are cultured in medium supplemented with microvesicle-free serum (the serum may be depleted of microvesicles by ultracentrifugation, filtration, precipitation, etc.). After culturing the cells for a period of time, the medium is removed and transferred to conical tubes and centrifuged at 400×g for 10 minutes at 4° C. to pellet the cells. Next, the supernatant is transferred to new conical tubes and centrifuged at 2000×g for 30 minutes at 4° C. to further remove cells and cell debris. This may be followed by another centrifugation step (e.g. 10000×g for 30 minutes to further deplete cellular debris and remove larger particles).

Microvesicles are then precipitated at 4° C. using 8.5% w/v PEG 6000 and 0.4 M NaCl. This mixture is spun at 10000×g at 4° C. for 30 minutes. The supernatant is removed and the pellet is resuspended in an appropriate buffer (e.g. PBS). It may be used for immediate downstream reactions or further purified. Further purification procedures can include the use of centrifugal filters (e.g. MWCO of 100 kDa), immunoaffinity, HPLC, tangential flow filtration, phase separation/partitioning, microfluidics, etc.

Example 3: Isolation of Microvesicles from Culture Medium Conditioned Using Bone Marrow Derived Stem Cells by the Methods of the Present Invention Normal donor human bone marrow was acquired from AllCells LLC (Emeryville, Calif., http://www.allcells.com). MSCs were isolated by a standard plastic adherence method. Bone marrow mononuclear cells were isolated by low-density centrifugation using Ficoll-Paque Premium (density: 1.077 g/ml) according to the manufacturer's protocol (GE Healthcare Life Sciences, Pittsburgh, Pa.). The mononuclear cells were collected at the interface, washed three times in phosphate-buffered saline (PBS) supplemented with 2%

FBS (Atlanta Biologics, Atlanta, Ga.), and resuspended in MSC medium consisting of alpha-minimum essential medium (α-MEM) (Mediatech Inc., Manassas, Va.) and 20% FBS, 1% Penicillin/Streptomycin (Lonza, Allendale, N.J.) and 1% glutamine (Lonza).

Initial cultures of either MSC's or mononuclear cells were seeded between $2\text{-}3 \times 10^5$ cells/cm$^2$ in tissue culture-treated dishes (BD Biosciences, San Jose, Calif.) and placed in a cell incubator at 37° C. in 95% humidified air and 5% $CO_2$. After 48-72 hours, the non-adherent cells were removed, the culture flasks were rinsed once with PBS, and fresh medium was added to the flask. The cells were grown until 80% confluence was reached and then passaged by Trypsin-EDTA (Life technologies, Carlsbad, Calif.). Cells were split at a 1:4 ratio into 5-layer multiflasks (BD Biosciences). Alternatively, cryopreserved MSC were thawed at 37° C. and immediately cultured in α-MEM supplemented with 20% microvesicle-free fetal bovine serum and 1% penicillin/streptomycin/glutamine at 37° C. in 95% humidified air and 5% $CO_2$. They were expanded similar to above.

The cells were grown in the multiflasks until 80-90% confluence was reached. The flasks were rinsed twice with PBS and α-MEM supplemented with 1% Penicillin/Streptomycin/Glutamine was added. After 24 hours, the conditioned medium transferred to 50 mL conical centrifuge tubes (Thermo Fisher Scientific Inc, Weston, Fla.) and immediately centrifuged at 400×g for 10 minutes at 4° C. to pellet any non-adherent cells. The supernatant was transferred to new 50 mL conical centrifuge tubes and centrifuged at 2000×g for 30 minutes at 4° C. to further remove cells and cell debris.

The supernatants were collected and placed into 250 ml sterile, polypropylene disposable containers (Corning, Corning, N.Y.). To the supernatant, rnase and protease free polyethylene glycol average molecular weight 6000 (Sigma Aldrich, Saint Louis, Mo.) at 8.5 w/v % and sodium chloride (final concentration 0.4 M) were added. The solution was placed in a cold room at 4° C. overnight with rocking. The solution was transferred to 50 mL conical centrifuge tubes and centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200 µl) from the bottom of the filter device. Protein concentration was determined by the micro BSA Protein assay kit (Pierce, Rockford, Ill.) and the enriched microvesicle solution was stored at −70 degrees or processed for downstream use (e.g. protein, RNA, and DNA extraction).

Example 4: Isolation of Microvesicles from Plasma by the Methods of the Present Invention Approximately 6-8 ml of blood (human and pig) was collected via venipuncture and placed into BD Vacutainer plastic EDTA lavender tubes (BD Biosciences, San Jose, Calif.). The venipuncture tubes were centrifuged at 400×g for 30 minutes at room temperature. Plasma was removed (approximately 3-4 ml) and placed into new 50 ml conical centrifuge tubes (Thermo Fisher Scientific Inc, Weston, Fla.). Sterile alpha-minimum essential medium (α-MEM) (Mediatech Inc., Manassas, Va.) was added in a 1:10 (Plasma to medium) ratio.

To the solution, rnase and protease free polyethylene glycol average molecular weight 6000 (Sigma Aldrich, Saint Louis, Mo.) at 8.5 w/v % and sodium chloride (final concentration 0.4 M) were added. The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, Ill.) and the enriched microvesicle solution was stored at −70 degrees or processed for downstream use (e.g. protein, RNA, and DNA extraction).

Example 5: Isolation of Microvesicles from Bone Marrow Aspirate by the Methods of the Present Invention Pig bone marrow was isolated from the iliac crest. The skin area was carefully cleaned with povidine iodine 7.5% and isopropanol 70%. An 11-gauge 3 mm trocar (Ranafac, Avon, Mass.) was inserted into the iliac crest. An aspiration syringe with loaded with 5000-1000 units of heparin to prevent clotting of the marrow sample. Approximately 20-25 ml of marrow was aspirated and the solution transferred to 50 ml conical centrifuge tubes. Alternatively, normal donor human bone marrow (approximately 50 ml) was acquired from AllCells LLC (Emeryville, Calif., http://www.allcells.com).

The 50 ml conical tubes were centrifuged at 400×g for 30 minutes at room temperature. The supernatant (the acellular portion) was collected (approximately 10-12 ml per 50 ml) and placed into new 50 ml conical centrifuge tubes (Thermo Fisher Scientific Inc, Weston, Fla.). Sterile alpha-minimum essential medium (α-MEM) (Mediatech Inc., Manassas, Va.) was added in a 1:10 (bone marrow supernatant to medium) ratio. The solution was transferred to new 50 ml conical tubes and centrifuged at 2000×g for 30 minutes at 4° C. The supernatant was transferred to new 50 ml conical tubes and to this solution, rnase and protease free polyethylene glycol average molecular weight 6000 (Sigma Aldrich, Saint Louis, Mo.) at 8.5 w/v % and sodium chloride (final concentration 0.4 M) were added.

The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, Ill.) and the enriched microvesicle solution was stored at −70 degrees or processed for downstream use (e.g. protein, RNA, and DNA extraction).

The cellular portion was collected and processed for mesenchymal stem isolation or for bone marrow complete isolation.

Example 6: Isolation of Microvesicles from Urine by the Methods of the Present Invention Approximately 500 ml of clean catch human urine was isolated and placed into 50 ml conical tubes (Thermo Fisher Scientific Inc, Weston, Fla.).

The 50 ml conical tubes were centrifuged at 400×g for 30 minutes at 4° C. The supernatant was removed and placed into new 50 ml conical centrifuge tubes (Thermo Fisher Scientific Inc, Weston, Fla.). The solution was transferred to new 50 ml conical tubes and centrifuged at 2000×g for 30 minutes at 4° C. The supernatant was transferred to new 50 ml conical tubes and to this solution, rnase and protease free polyethylene glycol average molecular weight 6000 (Sigma Aldrich, Saint Louis, Mo.) at 8.5 w/v % and sodium chloride (final concentration 0.4 M) were added.

The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, Ill.) and the enriched microvesicle solution was stored at −70 degrees or processed for downstream use (e.g. protein, RNA, and DNA extraction).

Example 7: Isolation of Microvesicles from Medium from a Long-Term Culture of Bone Marrow Cells by the Methods of the Present Invention Bone marrow was obtained from an aspirate (see example 1) and red blood cells were lysed using 0.8% ammonium chloride solution containing 0.1 mM EDTA (Stem Cell Technologies, Vancouver, BC). The nucleated cells were pelleted under a fetal bovine serum (Atlanta Biologics, Atlanta, Ga.) cushion at 400×g for 5 minutes. Nucleated cells were washed in McCoys 5a media (Mediatech Inc., Manassas, Va.) by pelleting at 400×g for 5 min. The cells were resuspended in culture media at a density of 1×10$^6$ cells/ml and plated in 25, 75 or 225 cm$^2$ flasks (Corning, Corning, N.Y.).

Culture media consisted of McCoy's 5a media, 1% sodium bicarbonate (Life technologies, Carlsbad, Calif.), 0.4% MEM non-essential amino acids (Life technologies), 0.8% MEM essential amino acids (Life technologies), 1% L-glutamine (Lonza, Allendale, N.J.), 0.1 µM Hydrocortisone (Life technologies), 1% penicillin/streptomycin (Lonza), 12.5% fetal calf serum (Atlanta Biologics) and 12.5% horse serum (Stem Cell Technology). The cultures were incubated at 33° C. and 5% $CO_2$. Feeding was performed weekly by adding half of the original volume of media without removing any media during the first nine weeks of culture. If the cultures were grown beyond nine weeks, the volume of culture media was reduced to the original volume and half the original volume of fresh media was added each week.

After approximately nine weeks of culture, the original medium was removed and stored. The cells were washed twice with phosphate buffered saline (PBS) and incubated for 24 hours in media consisting of McCoy's 5a media, 1% sodium bicarbonate, 0.4% MEM non-essential amino acids, 0.8% MEM essential amino acids (Life technologies), 1% L-glutamine (Lonza, Allendale, N.J.), and 1% penicillin/streptomycin (Lonza).

After 24 hours, the supernatant was transferred to 50 mL conical centrifuge tubes (Thermo Fisher Scientific Inc, Weston, Fla.) and immediately centrifuged at 400×g for 10 minutes at 4° C. to pellet any non-adherent cells. The original medium that was stored was added back to the cells. The supernatant were transferred to new 50 mL conical centrifuge tubes and centrifuged at 2000×g for 30 minutes at 4° C. to further remove cells and cell debris.

The supernatant was collected and placed into 250 ml sterile, polypropylene disposable containers (Corning, Corning, N.Y.). To the supernatant, rnase and protease free polyethylene glycol average molecular weight 6000 (Sigma Aldrich, Saint Louis, Mo.) at 8.5 w/v % and sodium chloride (final concentration 0.4 M) was added. The solution was placed in a cold room at 4° C. overnight with rocking. The solution was transferred to 50 mL conical centrifuge tubes and centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200 µl) from the bottom of the filter device. Protein concentration was determined by the micro BSA Protein assay kit (Pierce, Rockford, Ill.) and the enriched microvesicle solution stored at −70 degrees or processed for downstream use (e.g. protein, RNA, and DNA extraction).

Example 8: Analysis of the Microvesicles of the Present Invention

Samples of microvesicles were analyzed by electron microscopy. For transmission electron microscopy (TEM), each specimen of microvesicles was loaded on formvar-coated, 150 mesh copper grids (Electron Microscopy Sciences, Fort Washington, Pa.) for 20 minutes. The grids were drained and floated on drops of 2% glutaraldehyde for 5 minutes, then washed in double distilled water (DDOH), followed by staining on drops of 4% aqueous uranyl acetate and multiple washes in DDOH. The grids were examined at 80 kV in a Philips CM10 electron microscope.

FIG. 5 shows electron micrographs of microvesicles derived from human bone marrow-derived mesenchymal stem cells isolated by the ultracentrifuge method described in Example 1 (panels A&B) and according to the methods of the present invention as described in Example 3 (panels C&D). FIG. 6 shows electron micrographs of microvesicles derived from porcine bone marrow-derived mesenchymal stem cells isolated by the ultracentrifuge method described in Examples 1 (panels A&B) and according to the methods of the present invention as described in Example 3 (panels C&D). FIG. 7 shows electron micrographs of microvesicles derived from murine bone marrow-derived mesenchymal stem cells isolated by the ultracentrifuge method described in Examples 1 (panels A&B) and according to the methods of the present invention as described in Example 3 (panels C&D).

FIGS. 5 to 7 illustrate the differences between microvesicles isolated by the methods of the present invention compared to ultracentrifuge isolation. The microvesicles isolated according to the methods of the present invention have borders that are smoother, uncorrugated and appear more "intact."

Figure 8B:
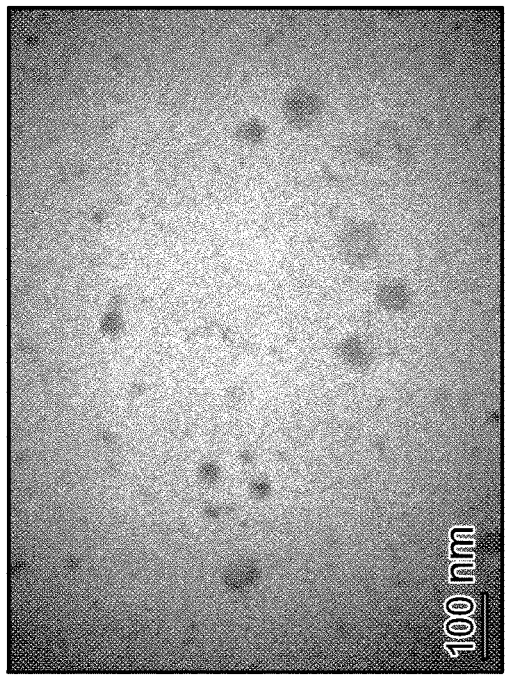
FIG. 8 shows electron micrographs of microvesicles isolated from human plasma according to the methods of the present invention. Panels A through C show the microvesicles under increasing magnification, as shown by the scale bars in the panels.
Figure 8C:
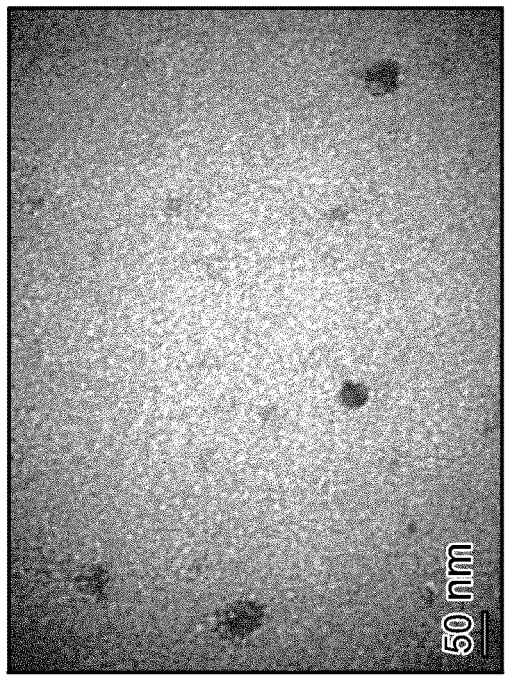
Figure 8A:
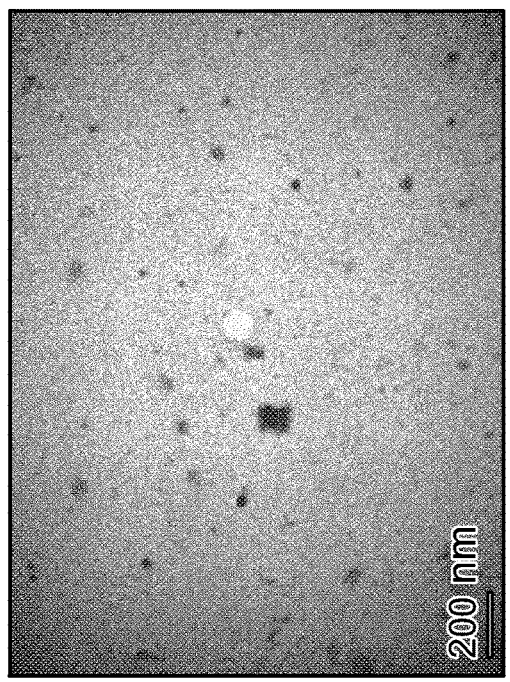
Figure 9A:
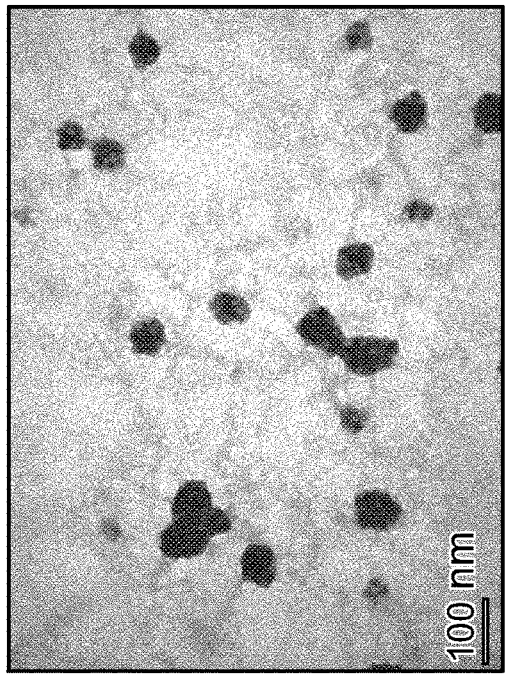
FIG. 9 shows electron micrographs of microvesicles isolated from porcine plasma according to the methods of the present invention. Panels A through C show the microvesicles under increasing magnification, as shown by the scale bars in the panels.
Figure 9B:
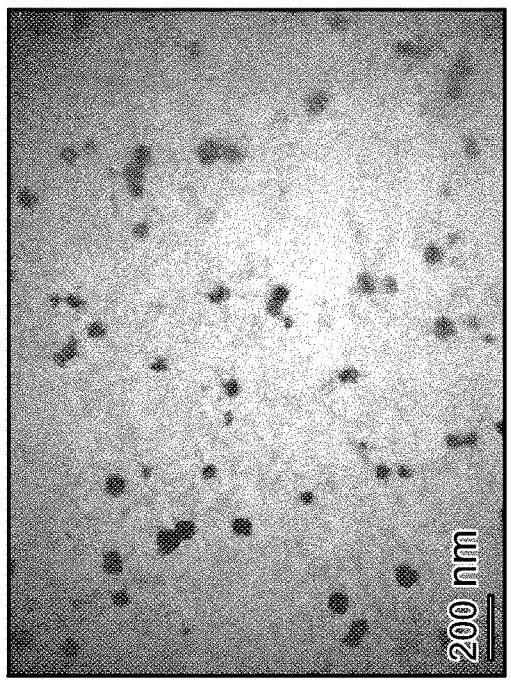
Figure 9C:
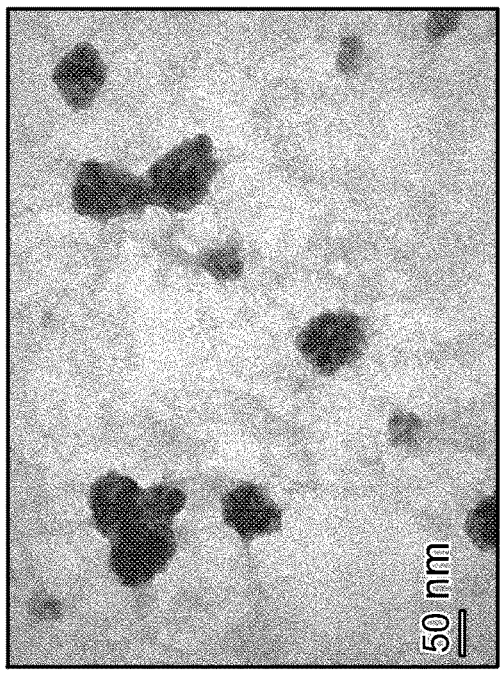
Figure 10A:
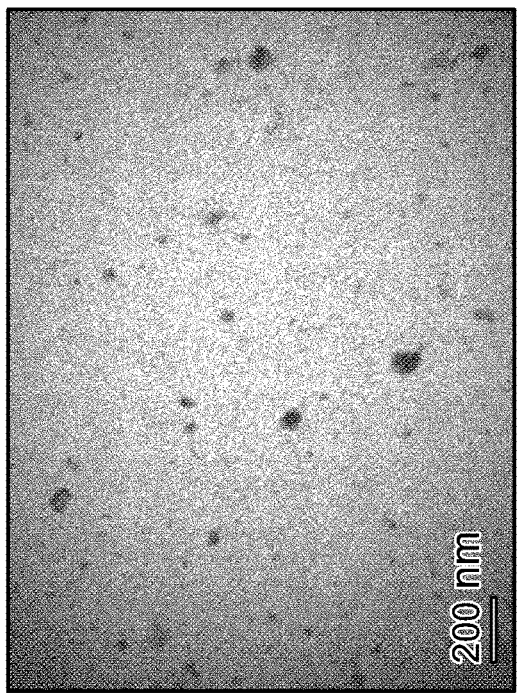
FIG. 10 shows electron micrographs of microvesicles isolated from human urine according to the methods of the present invention. Panels A through C show the microvesicles under increasing magnification, as shown by the scale bars in the panels.
Figure 10B:
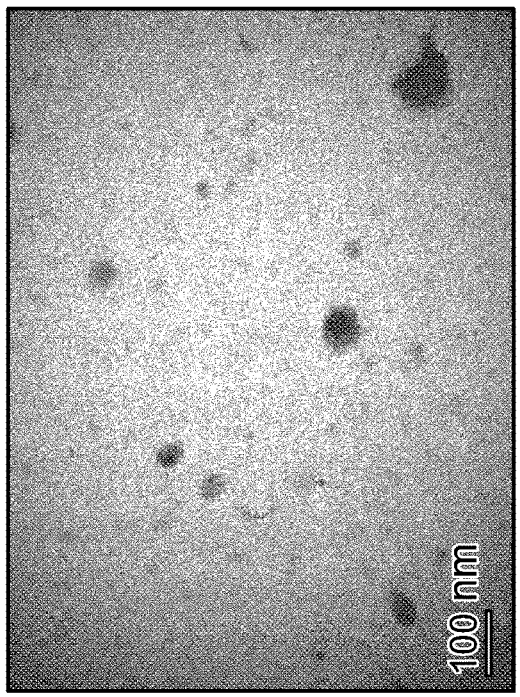
Figure 10C:
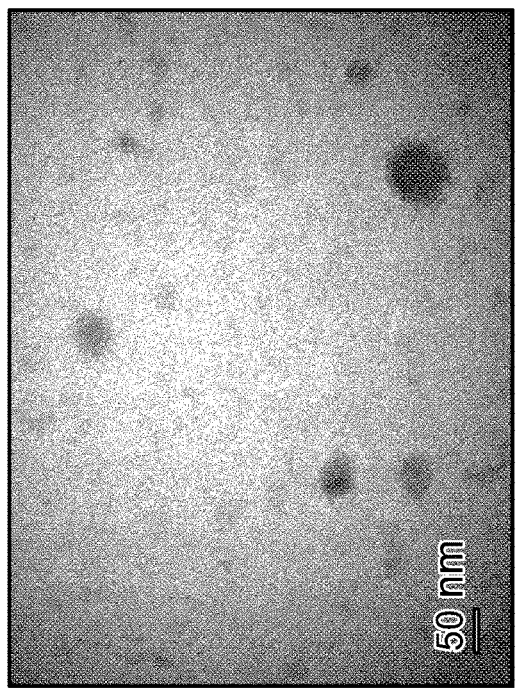

FIG. 8 shows electron micrographs of microvesicles isolated from human plasma according to the methods of the present invention. The heterogeneity of the shapes and sizes achieved with PEG isolation suggests that all types of microvesicles were isolated. Similar heterogeneity was observed in microvesicles from porcine plasma (FIG. 9) and human urine (FIG. 10) that were isolated according to the methods of the present invention.

To analyze protein expression in samples of microvesicles, cells and microvesicles were lysed in RIPA buffer (Cell signaling technology, Danvers, Mass.) and protein concentration estimated by the microBSA assay kit (Pierce, Rockford, Ill.). Approximately 20 micrograms of lysate were loaded in each lane and the membranes were probed overnight (1:1000) by either Rabbit anti-63 antibody (SBI Biosciences, Mountain View, Calif.), Rabbit anti-hsp70 (SBI Biosciences), rabbit STAT3 (Cell signaling technology), and/or rabbit phospho-STAT3 (Cell signaling technology).

Figure 11:
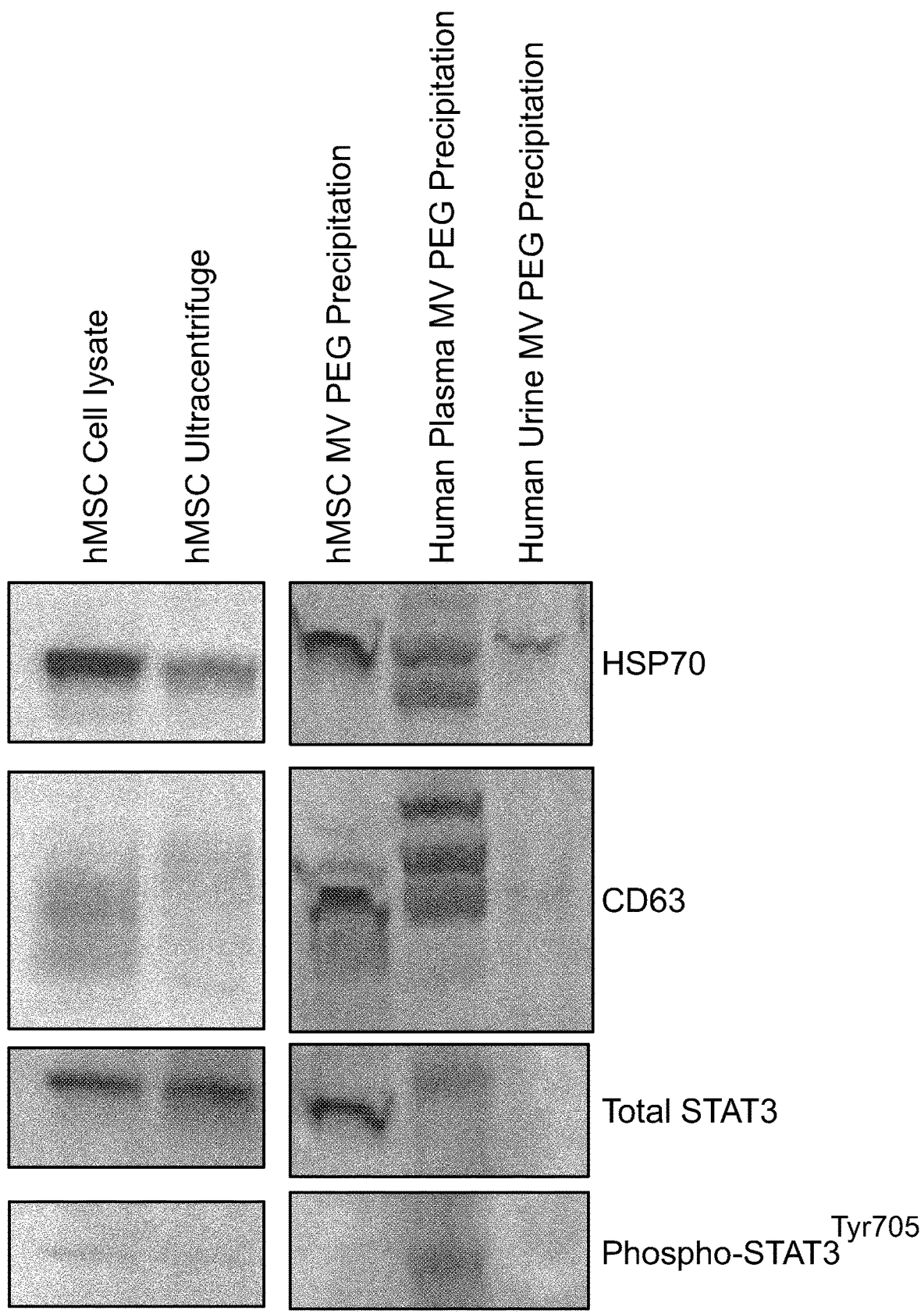
FIG. 11 shows a western blot, reporting the expression of HSP70, CD63, STAT 3 and phosphorylated STAT3 in lysates of human bone marrow-derived mesenchymal stem cells, microvesicles isolated from medium conditioned using human bone marrow-derived stem cells, prepared by ultracentrifugation (hMSC MV Ultracentrifuge), or the methods of the present invention, as described in Example 3 (hMSC PEG Precipitation). Microvesicles derived from human plasma and human urine, prepared by the methods of the present invention, as described in Example 3 were also analyzed. (Human plasma PEG Precipitation) and (human urine PEG Precipitation) respectively.

The presence of the exosomal markers (HSP 70 and CD63) confirmed that the methods of the present invention were capable of isolating exosomes. Further, the exosomes also contained the transcription factor STAT3 and the activated phosphorylated form phospho-STAT3. See FIG. 11.

Example 9: The Effect of the Microvesicles of the Present Invention on Fibroblast Proliferation and Migration To study the ability the microvesicles of the present invention to promote or enhance wound healing, the ability of the microvesicles to stimulate the proliferation of dermal fibroblasts was tested. Normal human adult dermal fibroblasts were obtained from Life Technology (Carlsbad, Calif.). Chronic wound patient fibroblasts (pressure foot ulcer and diabetic foot ulcer) were collected under an IRB approved protocol (IND# BB IND 13201) from wounds of 2 years duration without evidence of healing despite standard of care and advanced wound care treatments. Normal and Chronic wound fibroblasts were plated at $5\times10^3$ cells per well on 24 well tissue culture plates (BD Biosciences, San Jose, Calif.). MTT cell proliferation assays were performed at day 0 and day 3. Microvescicles were added on day 0. Both PEG isolated and ultracentrifuge isolated microvesicles were approximately equivalent in increasing growth of both normal and chronic wound fibroblasts after 3 days. Phosphate buffered saline (PBS) and conditioned MSC medium depleted of microvesicles showed little growth. See FIG. 12.

Figure 13:
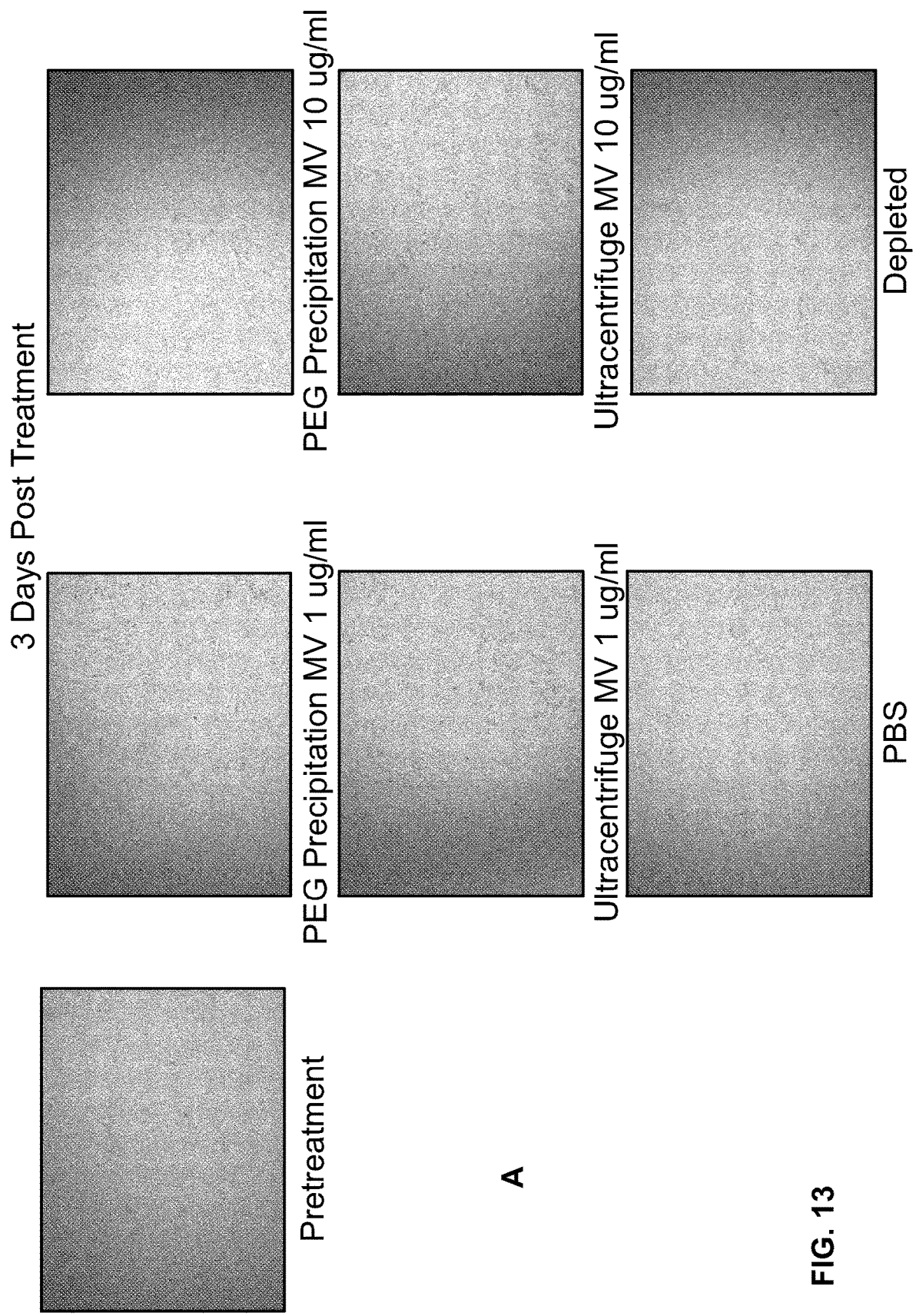
FIG. 13 shows the effect of microvesicles isolated from medium conditioned using human bone marrow-derived mesenchymal stem cells on the migration of human dermal fibroblasts, as determined by the ability of the fibroblasts to migrate into a region that had been scratched off. The panel labeled "pretreatment" shows a representative area of a cell culture plate where the cells were removed, prior to the addition of the test treatments. The effect of fibroblast migration was tested using microvesicles isolated according to the methods of the present invention (PEG precipitation) and microvesicles isolated by ultracentrifugation (Ultracentrifuge) at the concentrations shown. Fibroblasts treated with PBS or microvesicle depleted culture medium were included as a control.

In coculture experiments, normal adult fibroblasts and fibroblast from a diabetic foot ulcer were seeded in twenty four well plates. Each well was seeded to achieve 100% confluency (approximately $1\times10^5$ cells per well). To prevent the influence of cell proliferation, 2 hours prior to scratch, the medium was substituted with a fresh serum-free culture medium containing mitomycin at 10 μg/ml. The confluent monolayer was then scored with a 1 ml sterile pipette tip to leave a scratch of 0.4-0.5 mm in width. Culture medium was then immediately removed (along with any dislodged cells). The removed medium was replaced with fresh culture medium (10% FBS) containing either microvesicles (PEG or ultracentrifuge derived), PBS, or MSC conditioned medium depleted of microvesicles. The scratched area was monitored by collecting digitized images immediately after the scratch and 3 days after treatment. Digitized images were captured with an inverted IX81 Olympus microscope (Olympus America, Center Valley, Pa., http://www.olympusamerica.com) and ORCA-AG Hamamatsu digital camera (Hamamatsu Photonics K.K., Hamamatsu City, Shizuoka Pref., Japan, http://www.hamamatsu.com). Three days after treatment, microvesicles isolated according to the methods of the present invention showed the greatest in migration (essentially closing the wound), followed by microvesicles derived from ultracentrifuge. The controls (PBS) and MSC conditioned medium depleted of microvesicles (Depleted) showed little migration. See FIG. 13.

Figure 14:
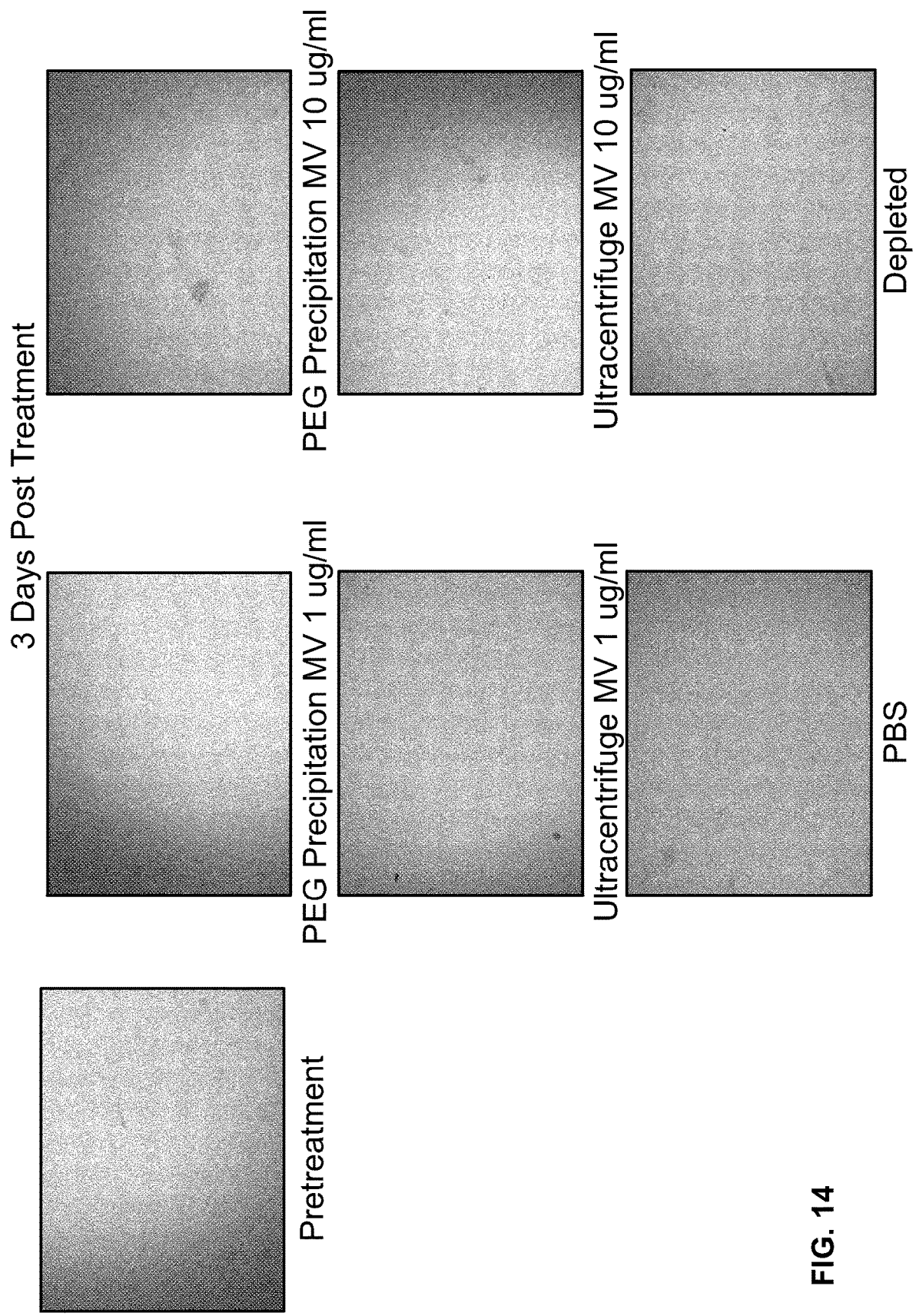
FIG. 14 shows the effect of microvesicles isolated from medium conditioned using human bone marrow-derived mesenchymal stem cells on the migration of human dermal fibroblasts obtained from a diabetic foot ulcer, as determined by the ability of the fibroblasts to migrate into a region that had been scratched off. The panel labeled "pretreatment" shows a representative area of a cell culture plate where the cells were removed, prior to the addition of the test treatments. The effect of fibroblast migration was tested using microvesicles isolated according to the methods of the present invention (PEG precipitation) and microvesicles isolated by ultracentrifugation (Ultracentrifuge) at the concentrations shown. Fibroblasts treated with PBS or microvesicle depleted culture medium were included as a control.

FIG. 14 shows the effects of microvesicles on cell migration fibroblasts derived from a diabetic foot ulcer. Similar to the results in FIG. 13, microvesicles isolated according to the methods of the present invention evoked the greatest migration, followed by microvesicles isolated using the ultracentrifuge method described in Example 1. The controls (PBS) and MSC conditioned medium depleted of microvesicles (Depleted) showed little migration.

Example 10: Uptake of the Microvesicles of the Present Invention into Cells

Human MSC microvesicles isolated from conditioned medium according to the methods of the present invention were labeled with the phospholipid cell linker dye PKH-26 (red) per manufacturer's instruction (Sigma-Aldrich, St. Louis, Mo.). Normal skin fibroblasts were labeled with Vybrant-Dio (Life technology) per manufacturer instructions. Normal skin fibroblasts were plated on fibronectin (Sigma-Aldrich) coated 4-well Nunc* Lab-Tek* II Chamber Slides (Thermo Fisher Scientific Inc, Weston, Fla.) ($5\times10^3$ cells per well). Cells were stained with the nuclear dye Hoechst 33342 (Life technology) per manufacturer's instructions. Dio labeled fibroblasts were treated with PKH-26 labeled microvesicles for 24 hours. Images were captured with an inverted IX81 Olympus microscope and ORCA-AG Hamamatsu digital camera. Normal dermal fibroblasts (stained with the green lipid membrane dye Dio) demonstrated uptake of PKH-26 labeled human MSC MV isolated by PEG precipitation in a peri-nuclear location. See FIGS. 15 and 16. In FIG. 16, the microvesicles are seen in a peri-nuclear location.

Figure 17:
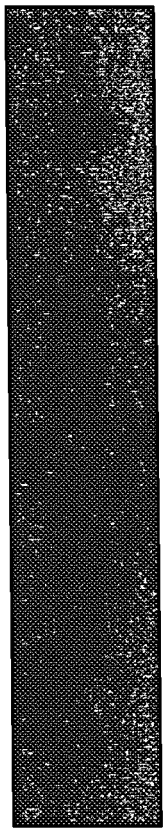
FIG. 17 shows a western blot of lysates of human dermal fibroblasts treated with: microvesicles isolated according to the methods of the present invention from plasma obtained from a patient suffering from rheumatoid arthritis (Human Plasma MV PEG Precipitation); microvesicles isolated according to the methods of the present invention from medium conditioned with bone marrow-derived mesenchymal stem cells (Human hMSC MV PEG Precipitation); microvesicles isolated via ultracentrifugation from medium conditioned with bone marrow-derived mesenchymal stem cells (Human hMSC MV ultracentrifugation); PBS control; and a depleted medium control (hMSC conditioned medium depleted of MV).

Example 11: Use of the Microvesicles of the Present Invention as a Diagnostic for Rheumatoid Arthritis Normal dermal fibroblasts were plated at a density of $1\times10^5$ cells/well in a 6 well tissue culture plate (BD Biosciences). Fibroblasts were serum starved overnight and treated with PBS (control), 10 micrograms of either microvesicles isolated according to the methods of the present invention from plasma obtained from a patient suffering from rheumatoid arthritis (Human Plasma MV PEG Precipitation); microvesicles isolated according to the methods of the present invention from medium conditioned with bone marrow-derived mesenchymal stem cells (Human hMSC MV PEG Precipitation); microvesicles isolated according via ultracentrifugation from medium conditioned with bone marrow-derived mesenchymal stem cells (Human hMSC MV ultracentrifugation); PBS control; and a depleted medium control (hMSC conditioned medium depleted of MV). The amount of STAT3 phosphorylation observed in the fibroblasts was greater in the microvesicles isolated according to the methods of the present invention. See FIG. 17.

Example 12: Use of the Microvesicles of the Present Invention as a Diagnostic for Metastatic Melanoma BRAF is a human gene that makes a protein called B-Raf. More than 30 mutations of the BRAF gene associated with human cancers have been identified. We have designed per primers to amplify the mutated form of BRAF that is linked to metastatic melanoma. The mutation is a T1799A mutation in exon 15 in BRAF. This leads to valine (V) being substituted for by glutamate (E) at codon 600 (now referred to as V600E). The presence of this mutation is required for treatment by the BRAF inhibitor Vemurafenib.

The SK-Me128 cell line, obtained from ATCC (Washington D.C., Md.) is known to have the T1799A mutation in exon 15 in BRAF. Microvesicles, isolated according to the methods of the present invention were obtained from medium conditioned by a 3 day incubation in EMEM (ATCC)+10% serum (Atlanta biologics, Atlanta, Ga.).

Figure 18:
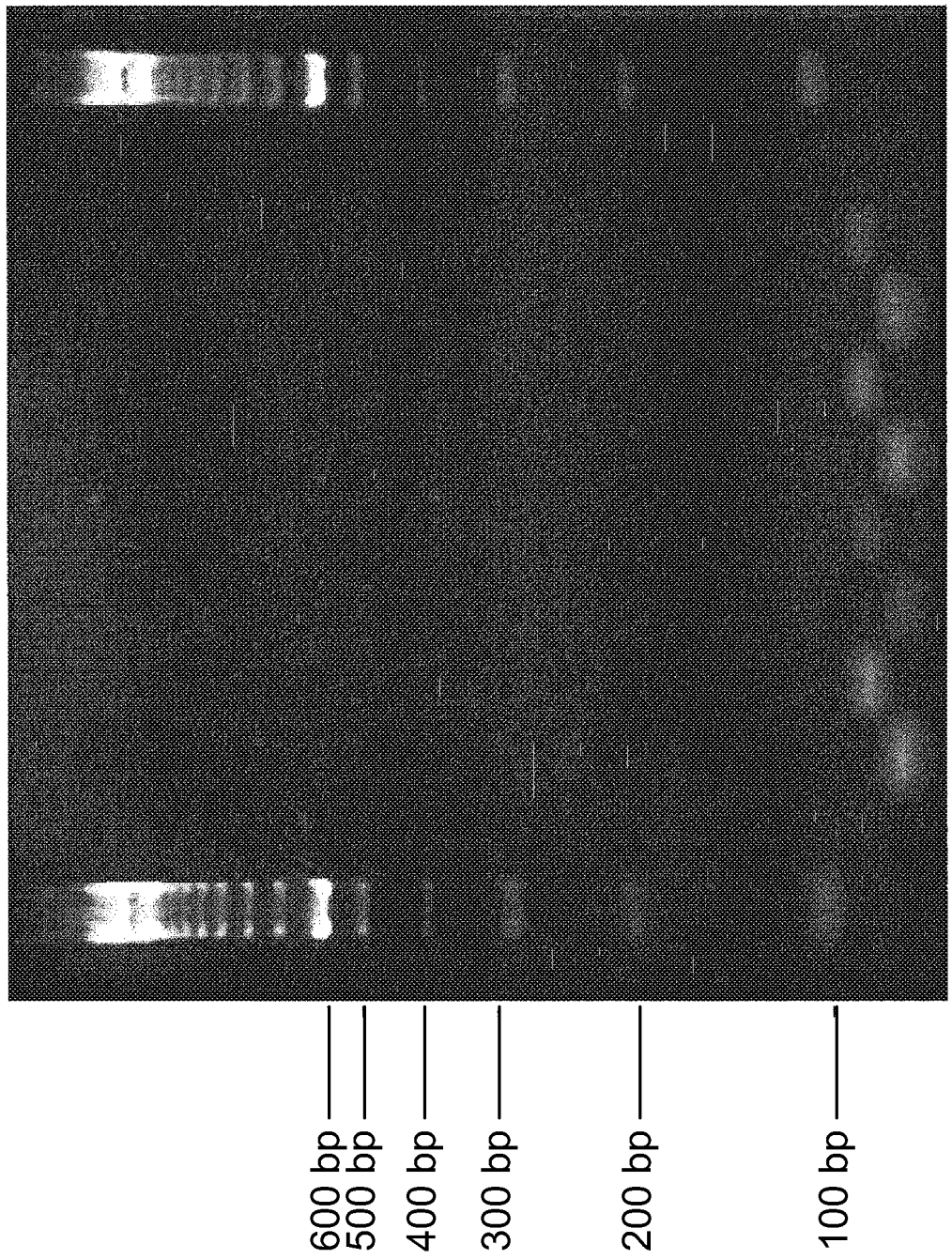
FIG. 18 shows the presence of the region containing exon 15 of BRAF containing the T1799A mutation, in: SK-MEL28 cells, from RNA amplified using primer 1 (lane 3); SK-MEL28 cells, from RNA amplified using primer 2 (lane 4); microvesicles isolated according to the methods of the present invention from medium conditioned with SK-MEL28 cells, from RNA amplified using primer 1 (lane 5); microvesicles isolated according to the methods of the present invention from medium conditioned with SK-MEL28 cells, from RNA amplified using primer 2 (lane 6); SK-MEL28 cells, from DNA amplified using primer 1 (lane 7); SK-MEL28 cells, from DNA amplified using primer 2 (lane 8); microvesicles isolated according to the methods of the present invention from medium conditioned with SK-MEL28 cells, from DNA amplified using primer 1 (lane 9); and microvesicles isolated according to the methods of the present invention from medium conditioned with SK-MEL28 cells, from DNA amplified using primer 2 (lane 10).
Figure 19:
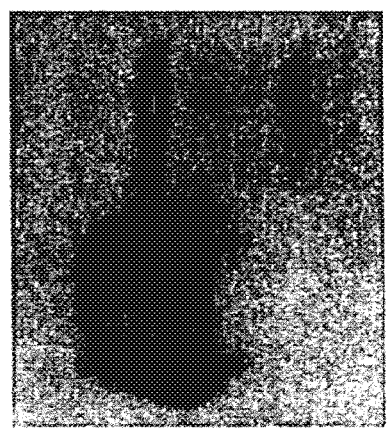
FIG. 19 shows the presence of V600E BRAF in a lysate of SK-MEL28 cells and a lysate of microvesicles isolated according to the methods of the present invention from medium conditioned with SK-MEL28 cells.

The isolated microvesicles were processed for DNA and RNA isolation using Qiagen's (Hilden, Germany) AllPrep DNA/RNA kit. Approximately 50 ng of RNA from SK-MEL28 cells and microvesicles were reverse transcribed using iScript™ Reverse Transcription Supermix (Biorad, Hercules, Calif.). A 2 µl aliquot was used for PCR utilizing Platinum® PCR SuperMix (Life technology) per manufacturer's instructions. In addition, 80 ng of DNA from SK-MEL28 cells and microvesicles was used for PCR utilizing Platinum® PCR SuperMix per manufacturer's instructions. PCR products were run on a 3% agarose gel and visualized by Biorad's gel-doc system. The results are shown in FIG. 18.

The primers used were:

```
Sequence 1:
Forward:
AGACCTCACAGTAAAAATAGGTGA

Reverse:
CTGATGGGACCCACTCCATC

Amplicon length: 70

Sequence 2:
Forward:
GAAGACCTCACAGTAAAAATAGGTG

Reverse:
CTGATGGGACCCACTCCATC

Amplicon length: 82
```

In addition, samples of the microvesicles were lysed in RIPA buffer and protein concentration estimated by the microBSA assay kit. Approximately 50 microgram were loaded in each lane and the membranes were probed overnight (1:1000) by mouse anti-BRAF V600E antibody (NewEast Biosciences, Malvern, Pa.). Secondary antibody, goat anti-mouse (Pierce) was applied at 1:10000 dilution for 1 hour. The Western blot shows BRAF V600E detection in SKMEL28 cell and MV lysate.

Example 13: Isolation of Microvesicles from Medium Conditioned Using a Culture of GFP-Labeled Bone Marrow-Derived Mesenchymal Stem Cells by the Methods of the Present Invention Homozygous transgenic mice expressing the enhanced Green Fluorescent Protein (GFP) under the direction of the human ubiqutin C promoter (C57BL/6-Tg(UBC-GFP) 30Scha/J) were obtained from Jackson Laboratories (Bar Harbor, Me.). These mice are known to express GFP in all tissues.

GFP-Mice (approximately 3-4 weeks of age) were euthanized by $CO_2$ asphyxiation. The limbs were cut above the hip and below the ankle joint. The hind limbs were harvested and skin, muscle, and all connective tissue was removed. The bones were then placed in a dish of ice cold sterile 1×PBS and washed several times in PBS. The ends of each bone were snipped off with scissors. A 10 cc syringe with warmed medium (α-MEM supplemented with 20% fetal bovine serum and 1% penicillin/streptomycin/glutamine) was forced through the bone shaft to extract all bone marrow into a 150 mm plate. This was repeated several times to ensure all the marrow was removed. The cell mixture was pipetted several times to dissociate cells and the cell suspension was passed through a cell strainer (70 µm size) (BD Biosciences, San Jose, Calif.) to remove large cell clumps or bone particles.

Initial cultures were seeded between $2-3×10^5$ cells/cm² in tissue culture-treated dishes (BD Biosciences, San Jose, Calif.) and placed in a cell incubator at 37° C. in 95% humidified air and 5% $CO_2$. After 72-96 hours the non-adherent cells were removed, the culture flasks were rinsed once with PBS, and fresh medium was added to the flask. The cells were grown until 80% confluence was reached and then passaged by Trypsin-EDTA (Life technologies, Carlsbad, Calif.). Cells were split at a 1:4 ratio.

Alternatively, cryopreserved GFP Mouse-MSC's were thawed at 37° C. and immediately cultured in α-MEM supplemented with 20% fetal bovine serum and 1% penicillin/streptomycin/glutamine at 37° C. in 95% humidified air and 5% $CO_2$. They were expanded similar to above.

The cells were grown in the flasks until 100% confluence was reached (approximately 1 week). The supernatant were transferred to 50 mL conical centrifuge tubes (Thermo Fisher Scientific Inc, Weston, Fla.) and immediately centrifuged at 400×g for 10 minutes at 4° C. to pellet any non-adherent cells. The supernatant was transferred to new 50 mL conical centrifuge tubes and centrifuged at 2000×g for 30 minutes at 4° C. to further remove cells and cell debris.

The supernatants were collected and placed into 250 ml sterile, polypropylene disposable containers (Corning, Corning, N.Y.). To the supernatant, rnase and protease free polyethylene glycol average molecular weight 6000 (Sigma Aldrich, Saint Louis, Mo.) at 8.5 w/v % and sodium chloride (final concentration 0.4 M) were added. The solution was placed in a cold room at 4° C. overnight with rocking. The solution was transferred to 50 mL conical centrifuge tubes and centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, Ill.) and the enriched microvesicle solution was stored at −70 degrees or processed for downstream use (e.g. protein, RNA, and DNA extraction).

Figure 20:
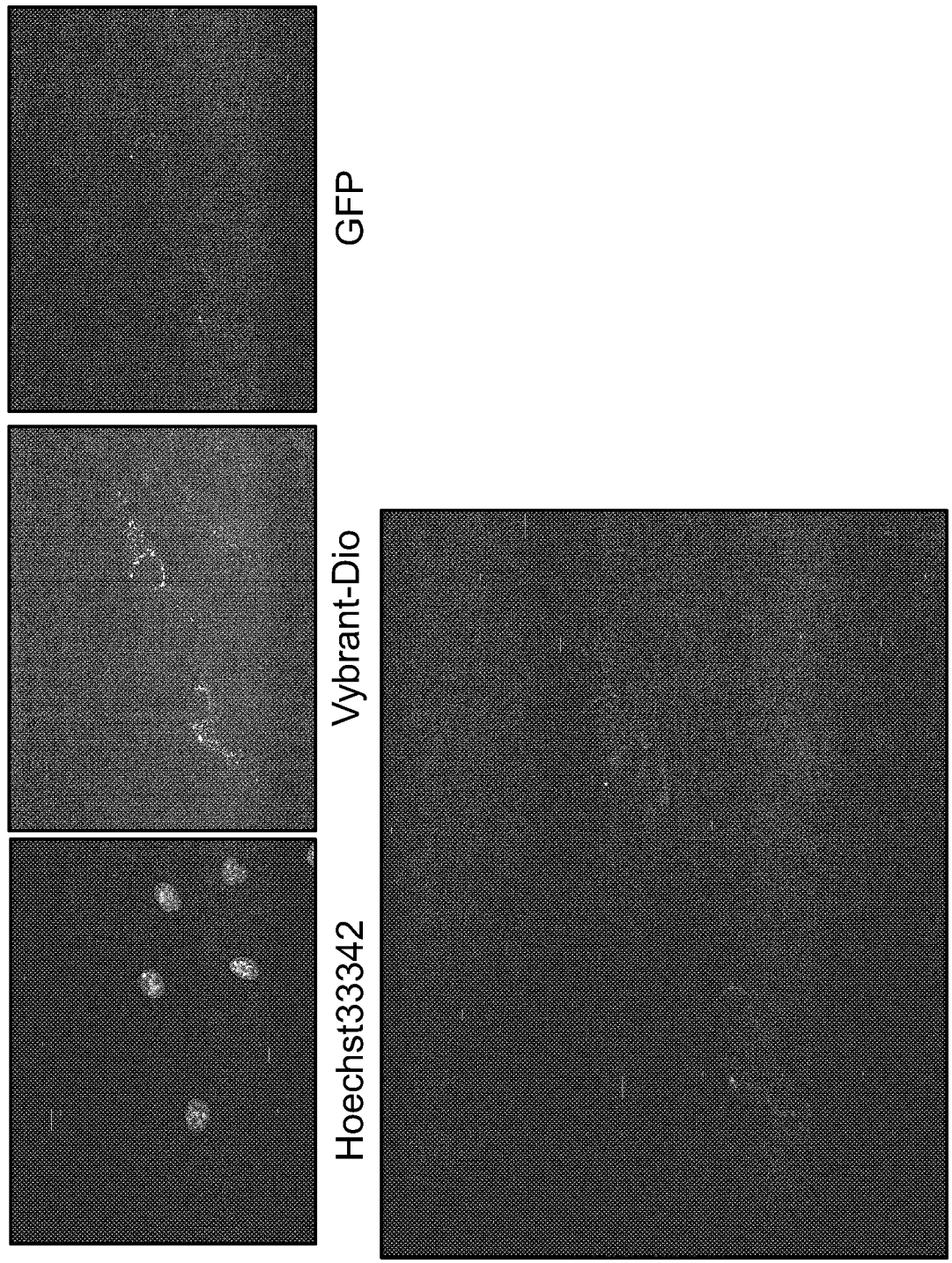
FIG. 20 shows the uptake of the microvesicles isolated according to the methods of the present invention from culture medium conditioned using bone marrow-derived stem cells obtained from a green fluorescent protein (GFP) expressing mouse into human dermal fibroblasts. Cell nuclei, resolved using Hoechst 33342 dye are shown in the panels labeled "Hoechst33342". Cells, resolved using vybrant dye are shown in the panel labeled "Vybrant-Dio". GFP-labeled microvesicles are shown in the panel labeled "GFP". A panel where images obtained from all three dyes are overlaid is seen in the panel labeled "Composite".
Figure 22A:
FIG. 22 shows histological sections of full-thickness wounds from: (A) untreated animals; (B) microvesicles isolated from medium conditioned using autologous bone marrow-derived mesenchymal stem cells according to the methods of the present invention; (C) saline; and (D) microvesicles isolated from autologous bone marrow-derived mesenchymal stem cells by ultracentrifugation, 5 days post wound.
Figure 22B:
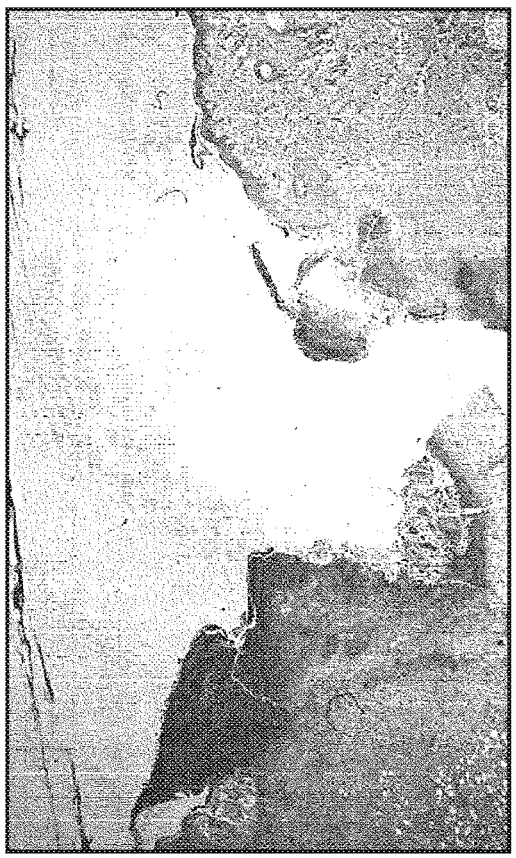
Figure 22C:
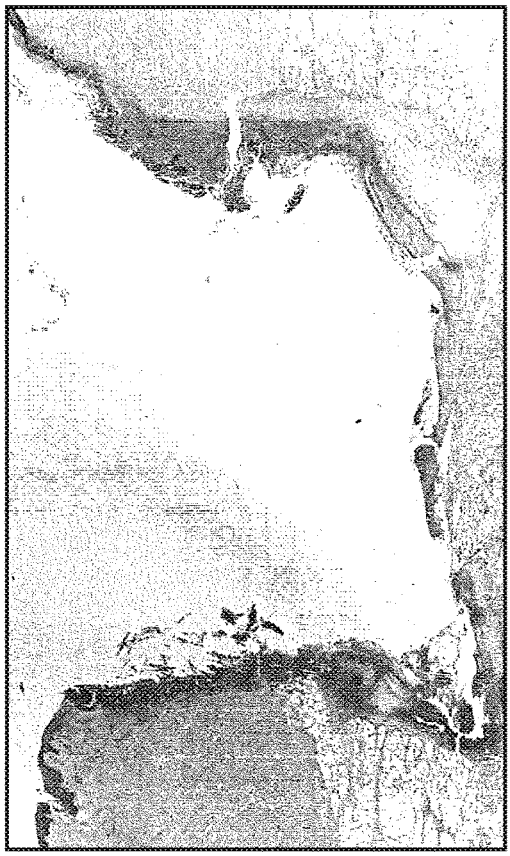
Figure 22D:
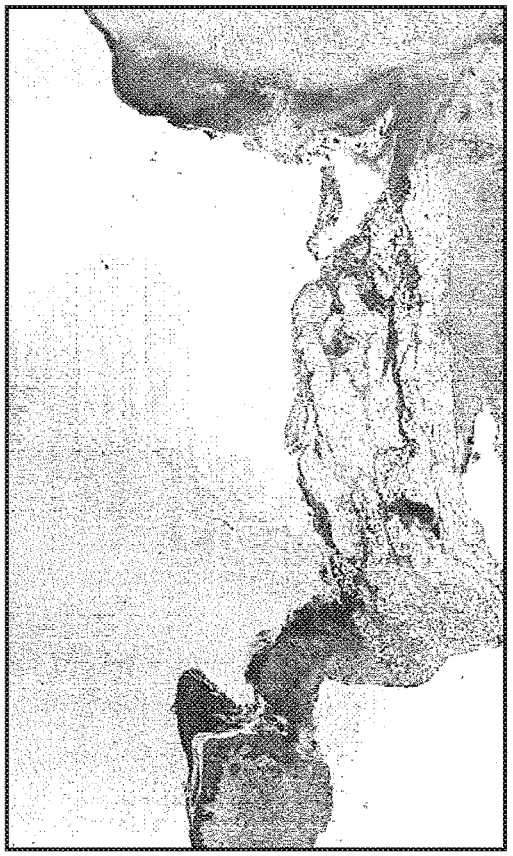
Figure 23A:
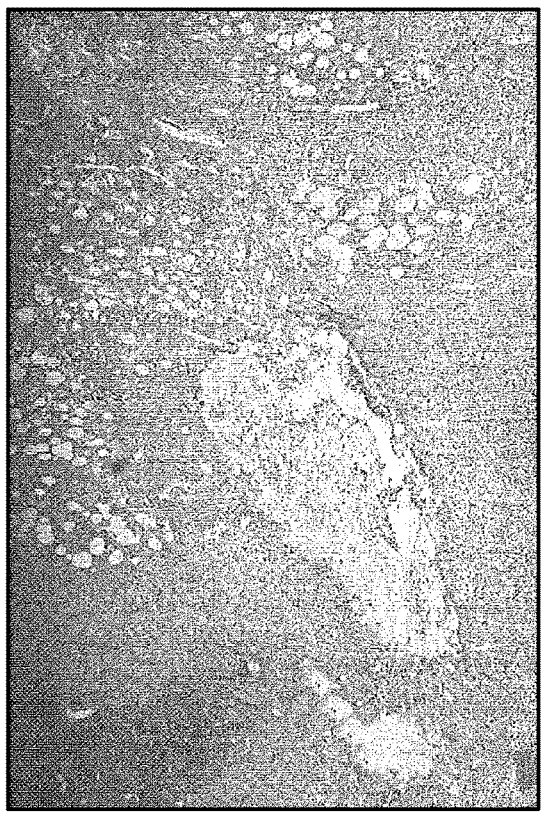
FIG. 23 shows pictures of second degree burns on animals treated with: (A) microvesicles isolated from medium conditioned using autologous bone marrow-derived mesenchymal stem cells by ultracentrifugation; (B) microvesicles isolated from medium conditioned using autologous bone marrow-derived mesenchymal stem cells according to the methods of the present invention; and (C) untreated animals, 7 days post wound. (D) shows a full thickness wound in an animal treated with microvesicles isolated from medium conditioned using autologous bone marrow-derived mesenchymal stem cells by ultracentrifugation 7 days post wound. Arrows indicate abscess formation in a full thickness wound treated with microvesicles isolated by ultracentrifugation at Day 7 (40x). This was not observed in full thickness wounds treated with microvesicles prepared according to the methods of the present invention.
Figure 23B:
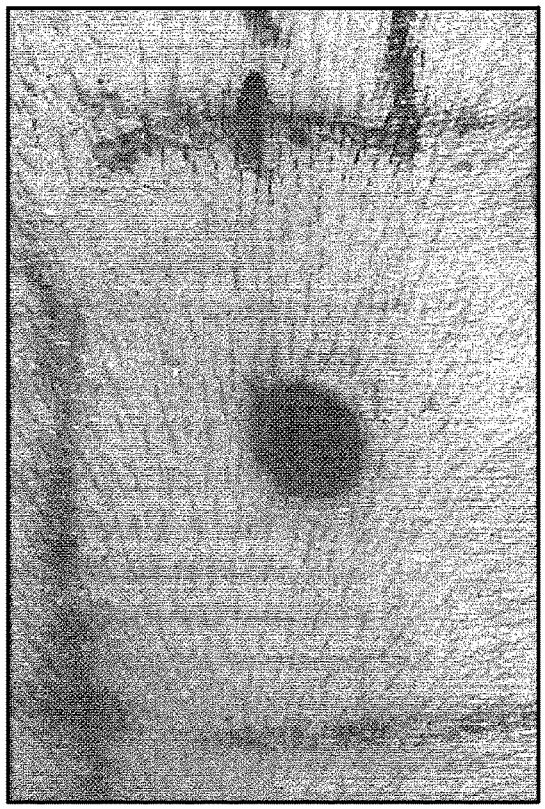
Figure 23C:
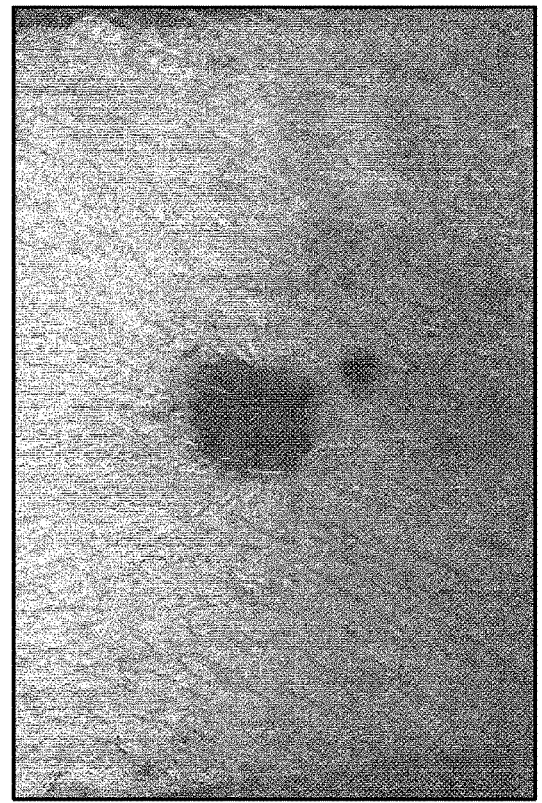
Figure 23D:

To determine cellular uptake of the microvesicles, normal human skin fibroblasts were labeled with Vybrant-Dio (Life technology) per manufacturer instructions. Normal skin fibroblasts were plated on fibronectin (Sigma-Aldrich) coated 4-well Nunc* Lab-Tek* II Chamber Slide (Thermo Fisher Scientific Inc) ($5 \times 10^3$ cells per well). Cells were stained with the nuclear dye Hoechst 33342 (Life technology) per manufacturer's instructions. DiI labeled fibroblasts were treated with microvesicles isolated from GFP expressing mouse MSC for 24 hours. Images were captured with an inverted IX81 Olympus microscope and ORCA-AG Hamamatsu digital camera. See FIGS. 20 and 21. Importantly, these images show that the microvesicles containing GFP were taken up by the cells.

Example 14: Use of the Microvesicles of the Present Invention as a Therapy to Promote or Enhance Wound Healing Full thickness wounds were created on the backs of pigs using a 10 mm punch biopsy instrument. Microvesicles were isolated from culture medium conditioned using autologous bone marrow-derived mesenchymal stem cells, either according to the methods described in Example 1 (the "conventional" ultracentrifugation method"), or by the methods described in Example 3. 30 micrograms of microvesicles were administered to the wounds by local injection at the time of wounding and at Days 1 and 2. Controls were treated with saline or allowed to heal air exposed. After 5 days, the animals were euthanized, and the wounds examined.

FIG. 22 shows the histology of the wounds 5 days post wounding. At 5 days, wounds treated with microvesicles isolated according to the methods of the present invention (i.e., according to the methods described in Example 3) appeared smaller than saline controls, air exposed controls and wounds treated with microvesicles prepared by ultracentrifugation. The wounds treated with microvesicles prepared by ultracentrifugation showed an enhanced inflammatory response, compared to those treated with microvesicles prepared according to the methods of the present invention and both controls.

In another study, second degree burn wounds were created on the backs of pigs using a brass rod heated to 100° C. Microvesicles were isolated from culture medium conditioned using autologous bone marrow-derived mesenchymal stem cells, either according to the methods described in Example 1 (the "conventional" ultracentrifugation method"), or by the methods described in Example 3. 30 micrograms of microvesicles were administered to the wounds by local injection at the time of wounding and at days 1 and 2. Controls were treated with saline or allowed to heal air exposed.

Over the course of the experiment (up to 28 Days post burn injury) wounds treated with microvesicles prepared by ultracentrifugation were significantly more inflamed than those treated with microvesicles prepared according to the methods of the present invention (i.e., according to the methods described in Example 3). See FIG. 23. Similarly, wounds treated with microvesicles prepared by ultracentrifugation were significantly more inflamed than saline controls and air exposed controls. Burn wounds treated with microvesicles prepared according to the methods of the present invention did not appear significantly more inflamed than controls.

FIG. 23 illustrates the difference in inflammation at Day 7 post wounding between wounds treated with microvesicles prepared by ultracentrifugation, microvesicles prepared according to the methods of the present invention and an air exposed control. Microscopically, abscess formation was seen in both full thickness and burn wounds treated with microvesicles prepared by ultracentrifugation. The inflammation noted with microvesicles prepared by ultracentrifugation is thought to be due to damaged microvesicles, which can easily stimulate an inflammatory cascade. The microvesicles of the present invention may also confer additional benefits by including additional particles.

Figure 24:
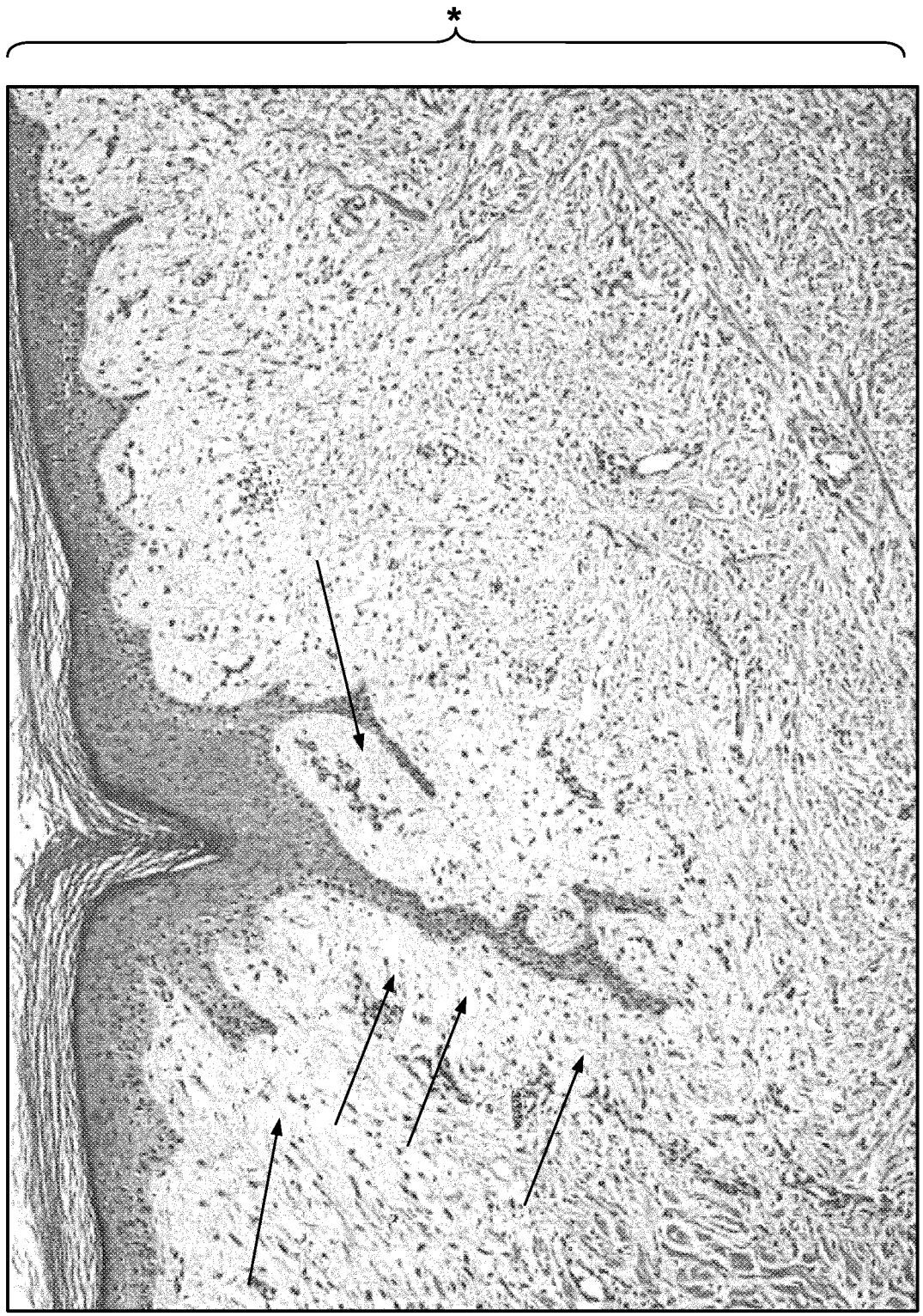
FIG. 24 shows a histological slide of a second degree wound, 28 days post wound, from an animal treated with microvesicles isolated from medium conditioned using autologous bone marrow-derived mesenchymal stem cells according to the methods of the present invention.

FIG. 24 shows a second degree porcine burn wound treated with microvesicles isolated by the methods of the present invention 28 days after burn injury. There is a significant remodeling of collagen, with the appearance of ground substance. These findings are indicative of dermal remodeling with collagen type III formation. There is also dermal epidermal induction resulting in a thickened epidermis that appears well anchored to the dermis. These findings are not observed in scar formation and are more consistent with dermal regeneration. An epidermis forming over a scar is easily subject to reinjury due to the inability to anchor well to a scarred dermis.

Figure 25:
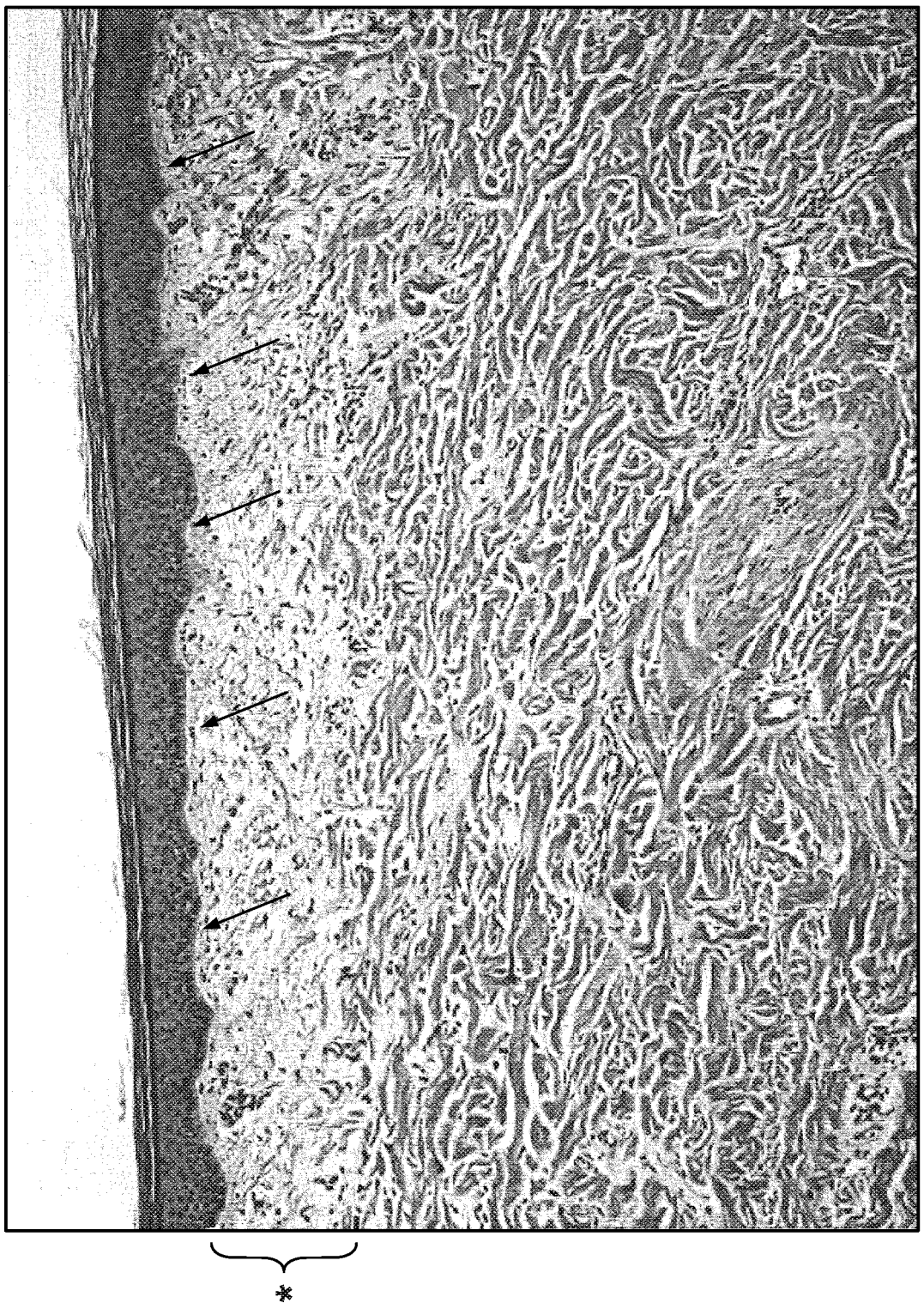
FIG. 25 shows a histological slide of a second-degree wound, 28 days post wound, from an animal treated with saline.

FIG. 25 shows a second degree porcine burn wound treated with saline 28 days after burn injury. There is minimal dermal regeneration with a flattened epidermis. The lack of significant rete ridge formation is highly suggestive of an inadequately anchored epidermis. These findings are much more indicative of scar formation with the risk of continued injury.

FIG. 26 shows a full thickness porcine wound treated with microvesicles isolated according to the methods of the present invention 28 days after injury. There is ingrowth of a nerve (illustrated by the arrows) into the remodeling dermis, likely stimulated by the application of the microvesicles. The nerve grown is accompanied by an angiogenic response (circled areas). The nerve appears to be a developed structure and is not due to simple axon sprouting. This is a unique finding and has never been reported and was also not observed in control wounds or wounds treated with microvesicles prepared by ultracentrifugation. These observations are highly indicative of complex tissue regeneration with the ability to generate mature elements from all germ layers including epidermis, stroma, vasculature and nervous tissue. These methods then appear to be widely applicable to the treatment of numerous conditions including traumatic, inflammatory, neoplastic and degenerative disorders of ectodermal, endodermal and mesodermal derived tissues.

Figure 27B:
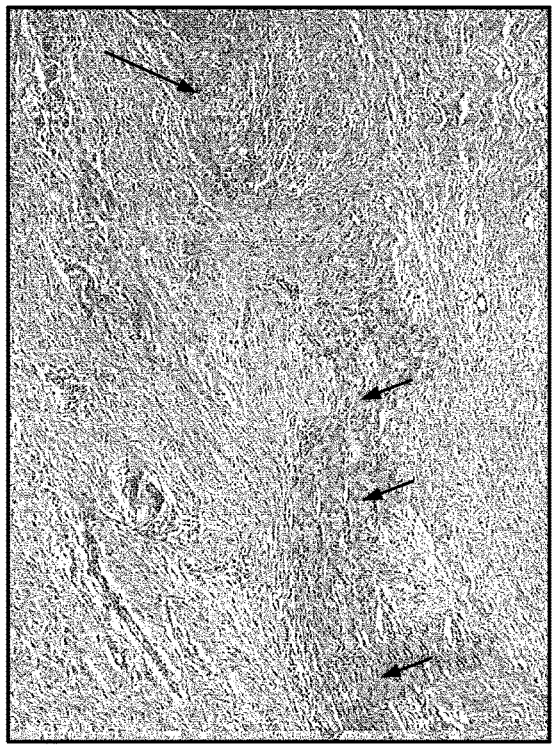
FIG. 27 shows a histological slide of a full-thickness wound, 28 days post wound, from an animal treated with microvesicles isolated from medium conditioned using autologous bone marrow-derived mesenchymal stem cells according to the methods of the present invention. A shows new nerve growth (arrows) and angiogenesis (circles). B shows new nerve growth (arrows). C shows new blood vessel growth (arrows).
Figure 27A:
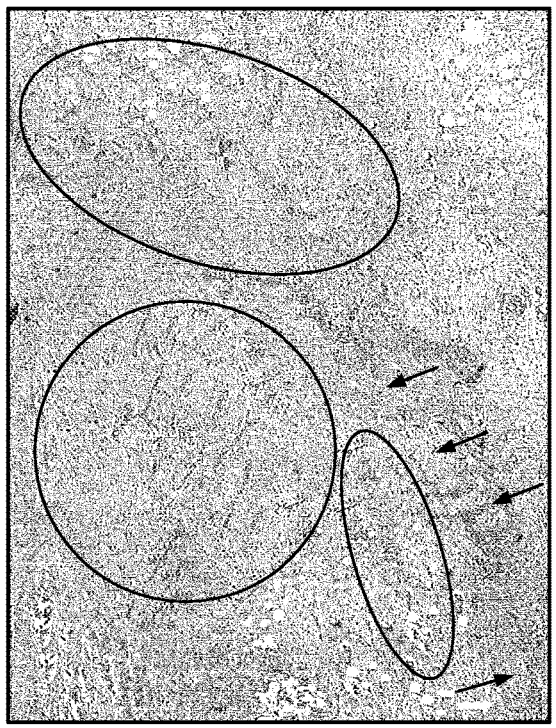
Figure 27C:
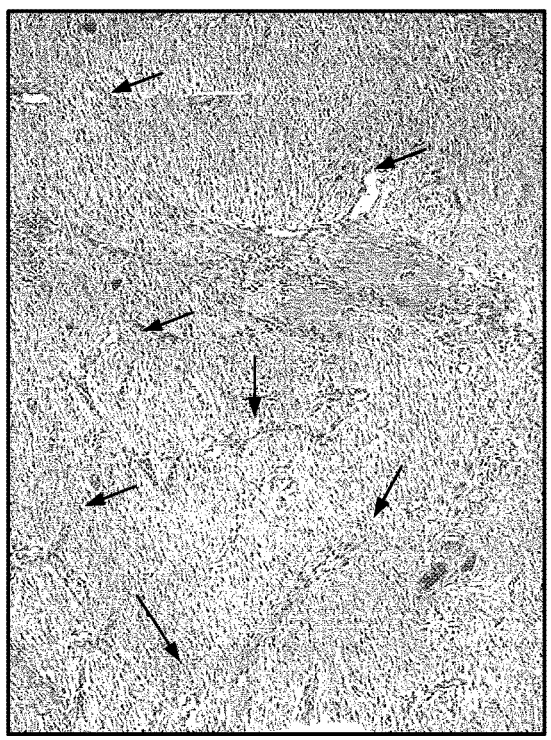

FIG. 27 shows a full thickness porcine wound treated with microvesicles isolated by the methods of the present invention 28 days after injury. This Figure illustrates the observations described in FIG. 26 at greater magnification. In A) the nerve growth appears to be following a path related to the angiogenic response. This finding is interesting as nerve growth is well known to follow angiogenesis in embryologic development. Again, these findings are indicative of tissue regeneration. B) shows the nerve at higher power. C) better illustrates the angiogenesis adjacent to the nerve growth.

Figure 28:
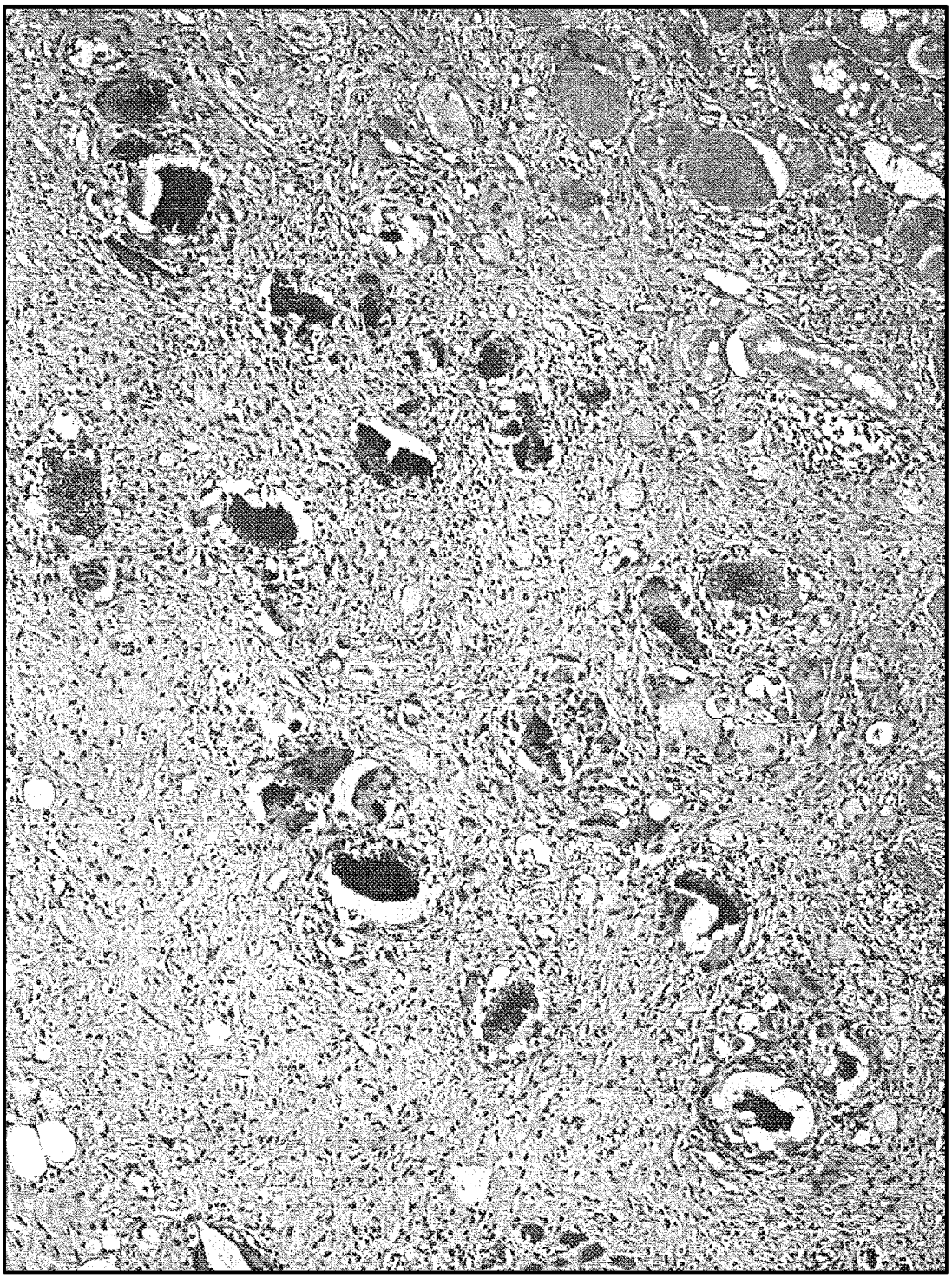
FIG. 28 shows a histological slide of a full-thickness wound, 7 days post wound in an animal treated with microvesicles derived from medium conditioned using autologous bone marrow-derived mesenchymal stem cells.

Bone formation was seen in all treatment groups (control and microvesicle treated) in the porcine full thickness wound model. See FIG. 28. Animals received a total of 1.44 mg microvesicles (half prepared according to the methods of the present invention and half by ultracentrifugation). There then appeared to be a systemic effect stimulating the formation of bone in all wounds. Bone formation tended to occur more in more inflammatory wounds suggesting a synergistic effect of local inflammatory mediators and the systemic effect of microvesicles.

Figure 29A:
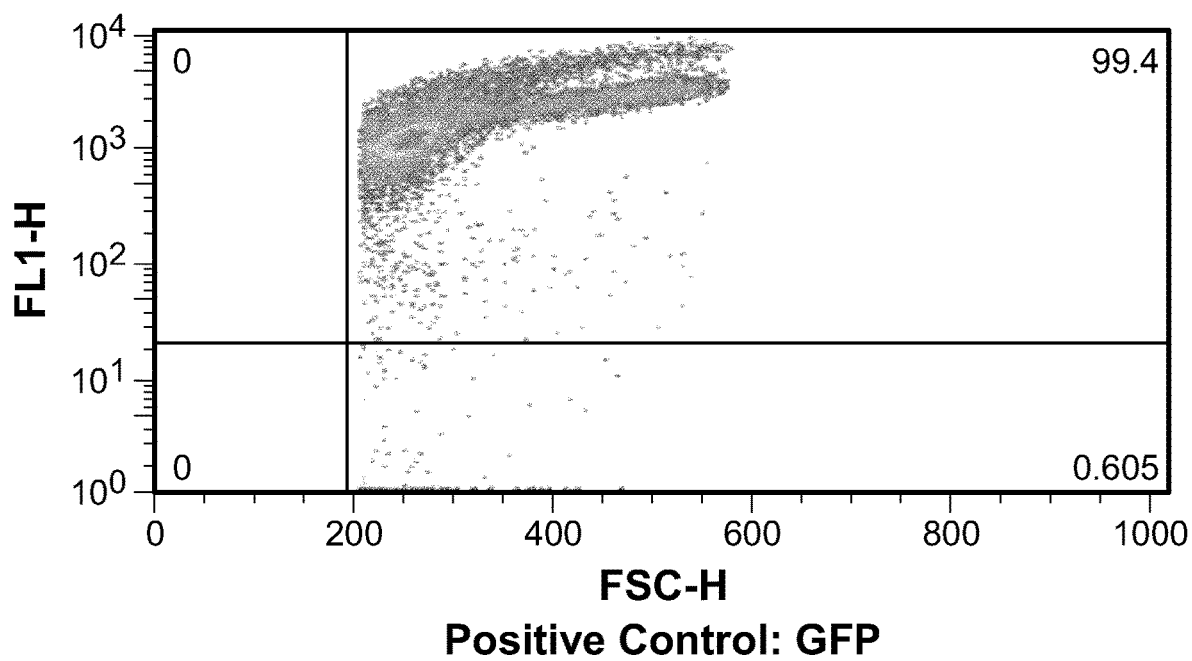
FIG. 29 shows the presence or absence of chimerism in irradiated animals following administration of GFP-labeled bone marrow.
Figure 29B:
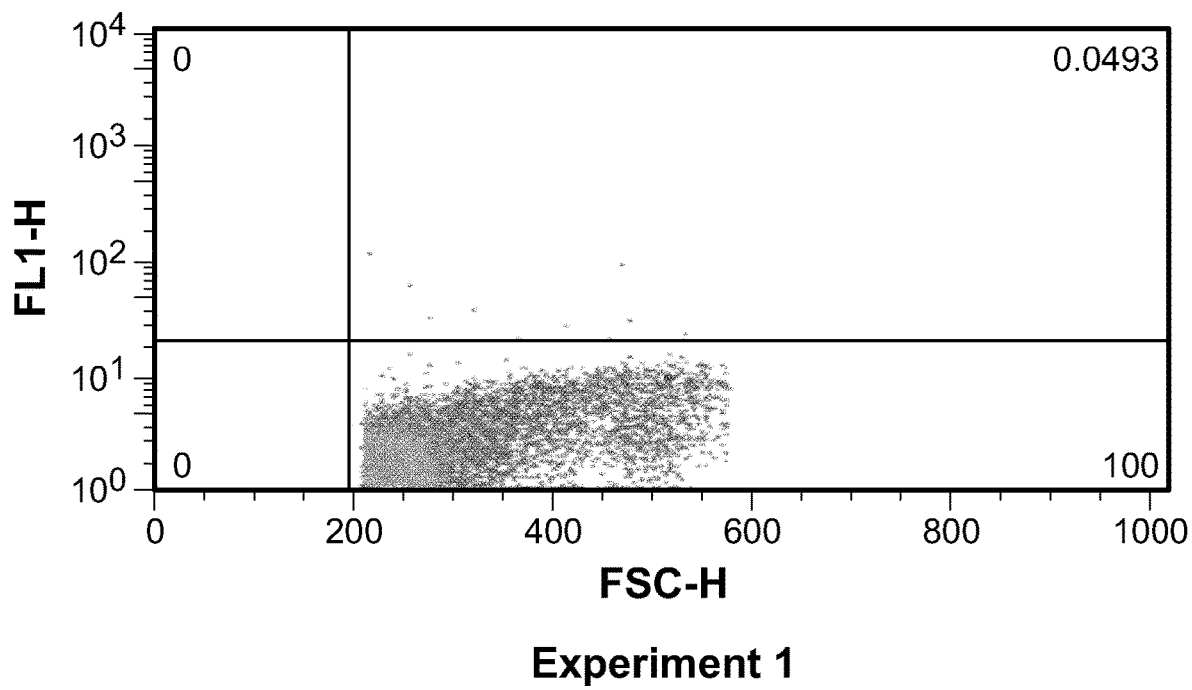

Example 15: Use of the Microvesicles of the Present Invention as a Therapy to Repopulate Bone Marrow and Regenerate Complex Structures C57/CJ6 (GFP$^-$) mice were lethally irradiated with two cycles of 400 cGy gamma irradiation to ablate their host bone marrow progenitors. After irradiation, mice were treated in an approximately 2 cm$^2$ area with an ablative fractional Erbium:YAG laser. After laser treatment, a plastic chamber was adhered to the skin, and bone marrow derived cells obtained from a syngeneic GFP$^+$ transgenic mouse were added to the chamber. The GFP$^+$ bone marrow cells included, freshly harvested total bone marrow cells, lineage negative selected bone marrow cells, mesenchymal stem cells and bone marrow complete cultured cells (as described in this application). In only a few animals was chimerism able to be achieved; detected by circulating GFP$^+$ cells 4 to 6 weeks after administration of cells. See FIG. 29. Surprisingly, many animals survived without evidence of donor bone marrow engraftment. Overall (in all groups of cells given) 30% of animals receiving cells survived. Among the different groups, survival rates were highest for animals receiving lineage negative selected cells (45%) and fresh bone marrow cells (30%). Control irradiated animals receiving no cells had a 100% mortality rate. Cytokines have failed to similarly rescue similarly lethally irradiated animals and no functional donor bone marrow engraftment could be demonstrated in these surviving animals. Microvesicles secreted by the delivered cells are likely responsible for the recovery of the host bone marrow leading to survival of these animals. We have demonstrated that fresh bone marrow (which includes lineage negative cells) and mesenchymal stem cells produce ample amounts of microvesicles that could accomplish this effect.

Figure 30A:
FIG. 30 panels A and B show the effects of MSC treatment on hair growth following gamma irradiation. Panel C shows the absence of chimerism in irradiated animals following administration of GFP-labeled bone marrow.
Figure 30B:
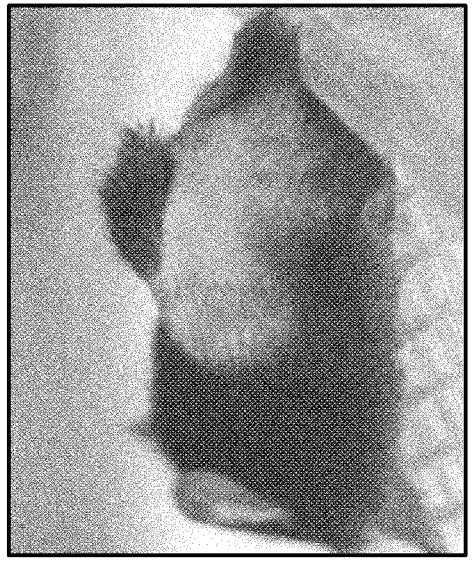
Figure 30C:
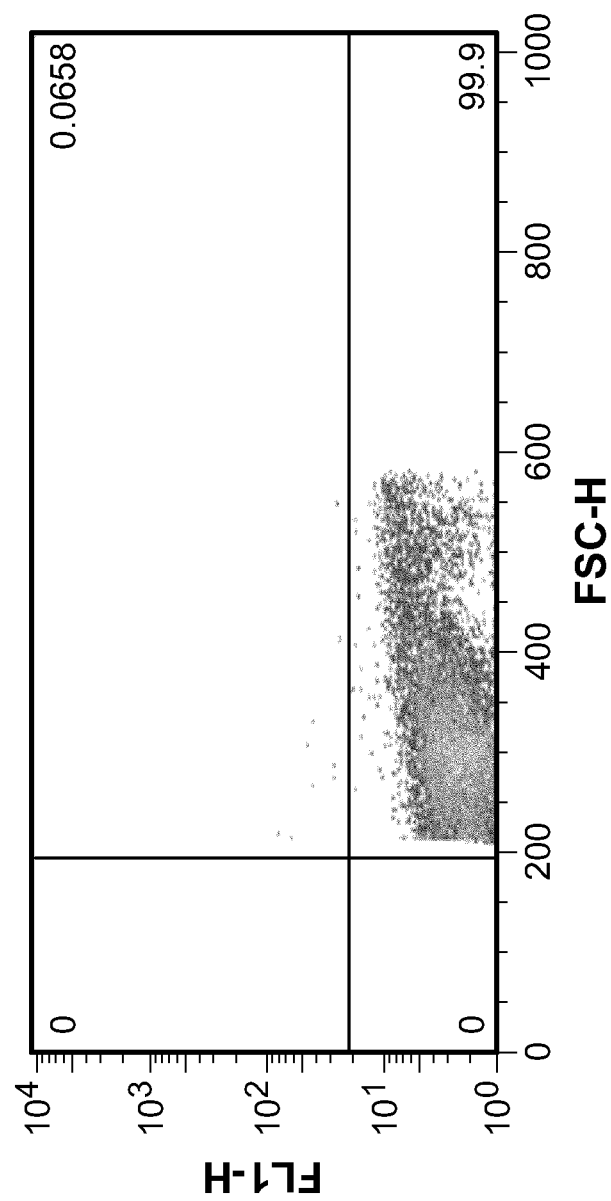

In another study, C57/CJ6 (GFP$^-$) mice were lethally irradiated with two cycles of 400 cGy gamma irradiation to inhibit their hair growth and partially ablate their bone marrow. After irradiation, the backs of the mice were shaved and the mice were then in an approximately 2 cm$^2$ area with an ablative fractional Erbium:YAG laser. After laser treatment, a plastic chamber was adhered to the skin and bone marrow derived cells obtained from a syngeneic GFP$^+$ transgenic mouse were added to the chamber. The GFP$^+$ bone marrow cells included, freshly harvested bone marrow cells, lineage negative selected bone marrow cells, mesenchymal stem cells and bone marrow complete cultured cells (as described in this application). In no animals was chimerism able to be achieved; detected by circulating GFP$^+$ cells 4 to 6 weeks after administration of cells. See FIG. 30. Animals receiving laser treatment alone had no to very minimal short stubby hair growth. FIG. 30 (A). In animals given bone marrow cells, there was significant, long lasting hair growth. FIGS. 30 (A & B). These findings were most dramatic in mice treated with GFP$^+$ lineage negative selected cells and total fresh GFP$^+$ bone marrow cells. Hair growth could be detected in 2 weeks and continued to grow for several months. Skin biopsies were taken in the area of new hair growth but no GFP$^+$ cells were detected. Functional engraftment of bone marrow cells could also not be detected in any animal by FACS analysis. FIG. 30 (C). As with the example in FIG. 29, cytokines have not been demonstrated to have this effect in restoring hair growth. Microvesicles secreted by the delivered cells are likely responsible for the stimulation of hair growth.

Example 16: Use of the Microvesicles of the Present Invention to Promote or Stimulate Angiogenesis and to Promote or Stimulate Fibroblast Proliferation Isolation of Bone Marrow Aspirate Microvesicles: Approximately 25 ml of fresh whole bone marrow was obtained from Allcells, Inc. (Alameda, Calif.). The bone marrow was carefully placed into new 50 ml conical centrifuge tubes and centrifuged at 400×g for 30 minutes at room temperature. The supernatant was carefully removed (approximately 15 ml) and placed into new 50 ml conical centrifuge tubes (Thermo Fisher Scientific Inc, Weston, Fla.) and centrifuged at 2000×g for 30 minutes at 4° C. The supernatant was again carefully removed and placed into new 50 ml conical centrifuge tubes to which sterile alpha-minimum essential medium (α-MEM) (Mediatech Inc., Manassas, Va.) was added in a 1:10 (Bone marrow supernatant to medium) ratio. To the solution, rnase and protease free polyethylene glycol average molecular weight 6000 (Sigma Aldrich, Saint Louis, Mo.) at 8.5 w/v % and sodium chloride (final concentration 0.4 M) were added. The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to amicon ultra-15 centrifugal filter units (nominal molecular weight limit 100 kDa) (Millipore, Billerica, Mass.) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device.

Figure 31:
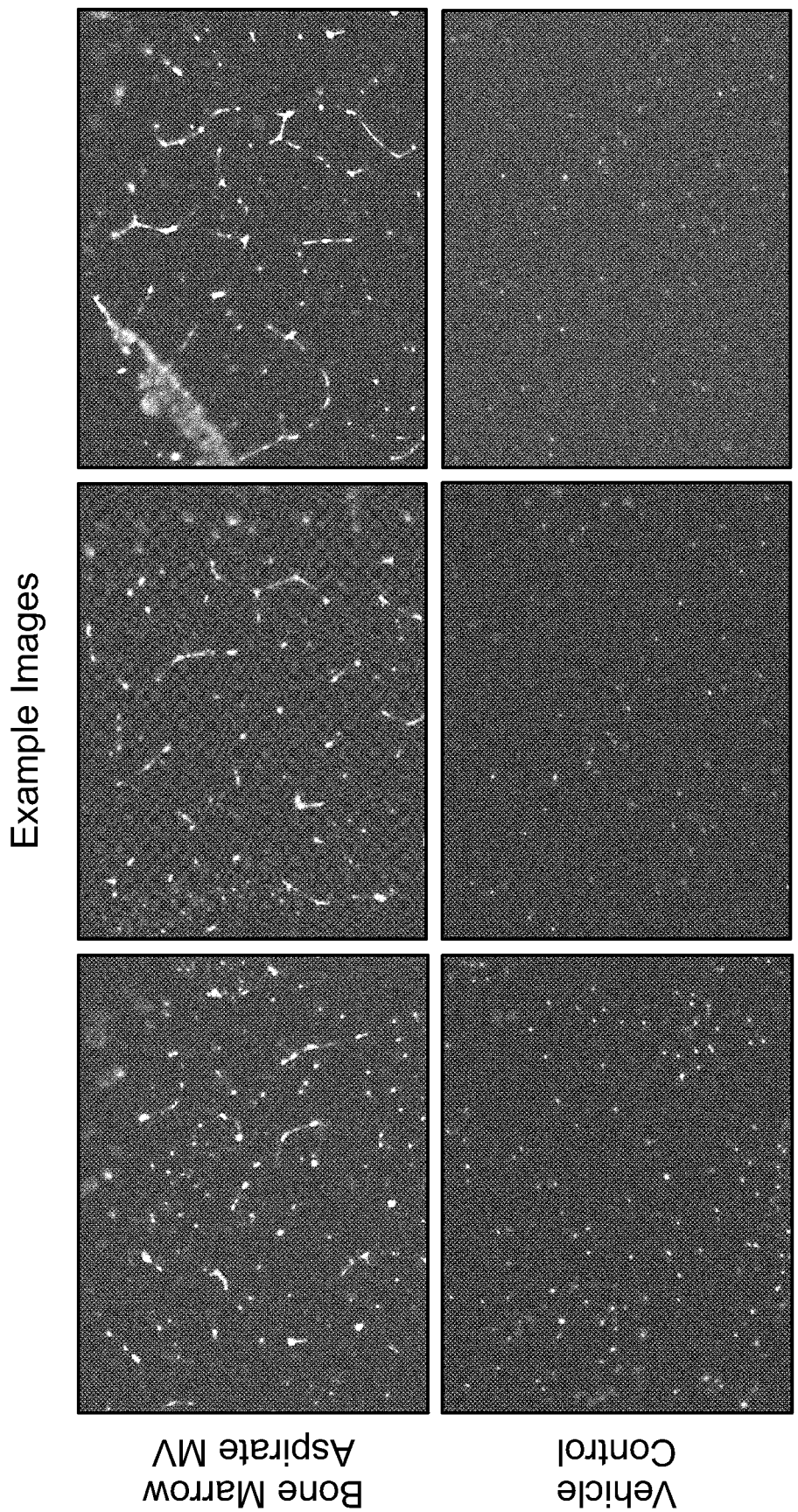
FIG. 31 shows the effect of bone marrow-derived microvesicles obtained using the method of the present invention on blood vessel formation, using an in vitro assay of angiogenesis. The upper three panels are representative images taken using an epifluorescent microscope of cultures of HUVEC cells treated with bone marrow-derived microvesicles obtained using the method of the present invention ("Bone Marrow Aspriate MV"). The lower three panels are representative images taken using an epifluorescent microscopem of cultures of HUVEC cells treated with vehicle control ("Vehicle Control").

Angiogenesis Assay:

Angiogenesis was measured using an endothelial tube formation assay (Invitrogen Life Technologies, Grand Island, N.Y.). Cryopreserved primary Human Umbilical Vein Endothelial cells (HUVEC) (Invitrogen Life Technologies) were grown in a 75-cm$^2$ tissue-culture flask for 6 days in Medium 200PRF supplemented with 2% low serum growth supplement (Invitrogen Life Technologies). Cells were then plated at a density of 3×10$^4$ in a 24 well tissue culture plate containing medium without supplement. HUVEC Cells were subsequently treated with bone marrow microvescles (approximately 100 µg). PBS was used as the vehicle control. Treated cells were incubated for 6 hours at 37° C. and 5% CO$^2$. Calcein AM fluorescent dye at a concentration of 2 µg/ml was used for visualization of tube formation. Fluorescent images were captured with an inverted IX81 Olympus microscope (Olympus America, Center Valley, Pa.). Bone marrow MV showed significant tube formation capacity as compared to the vehicle (PBS) control (see FIG. 31).

Figure 32A:
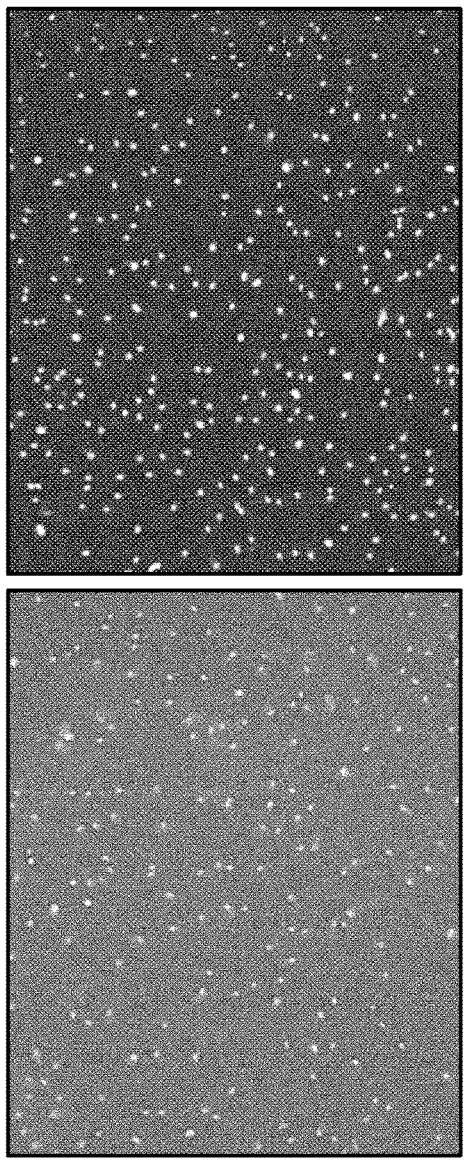
FIG. 32 shows the effect of bone marrow-derived microvesicles obtained using the method of the present invention on cell growth or proliferation, using an in vitro assay of cell growth. Panel A shows representative images taken using an epifluorescent microscope of cultures of normal adult fibroblasts treated with bone marrow-derived microvesicles obtained using the method of the present invention ("Bone Marrow MV") or PBS ("PBS"), three days post treatment. Panel B shows the average cell number in cultures of normal adult fibroblasts treated with bone marrow-derived microvesicles obtained using the method of the present invention ("Bone Marrow MV") or PBS ("PBS"), three days post treatment.
Figure 32B:
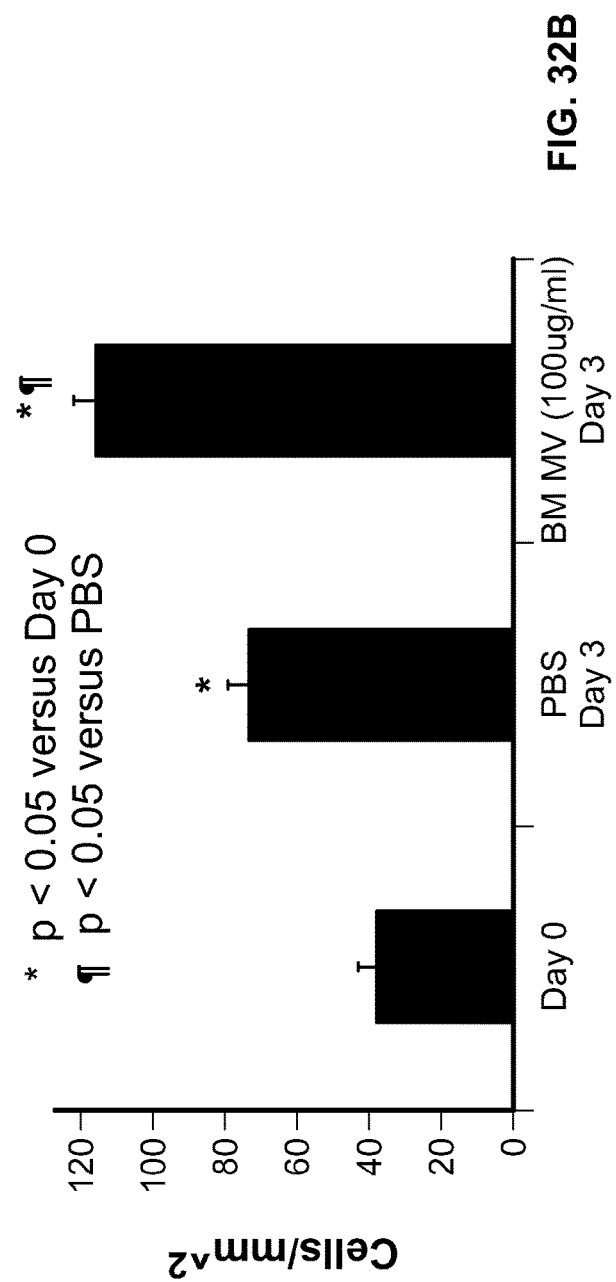

Growth Assay:

Normal adult fibroblasts were plated onto 24-well plates (10000 cells/well) in growth media (5% FBS, 1% glutamine, 1% Penicillin/Streptomycin) for the assays. After overnight incubation, three wells were randomly selected and the cells were stained with NucBlue Live ReadyProbes Reagent (Invitrogen Life technologies) (Day 0). Fluorescent images were captured using the EVOS FL Auto Cell Imaging System (Invitrogen Life technologies). Fibroblasts were re-fed with fresh medium containing bone marrow-derived microvesicles (approximately 100 μg) or PBS (vehicle control) and after three days (Day 3), cells were stained and imaged. Bone marrow-derived microvesicle treated fibroblasts increased approximately three fold in number (compared to Day 0) and at a significant greater rate than the vehicle control (FIG. 32, panel A and FIG. 32, panel B).

Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method of treating a skin wound in a patient in need thereof, the method comprising:
    administering a pharmaceutical composition of isolated microvesicles to the skin wound of the patient,
    wherein the pharmaceutical composition of isolated microvesicles is prepared comprising the steps of:
    (a) obtaining a biological fluid containing mammalian microvesicles from a mesenchymal stem cell;
    (b) precipitating the microvesicles by adding polyethylene glycol (PEG) to the biological fluid;
    (c) washing the precipitated microvesicles to remove the PEG;
    (d) isolating the microvesicles to obtain isolated microvesicles; and
    (e) providing a therapeutically effective amount of the precipitated isolated macrovesicles as a pharmaceutical composition,
    wherein the precipitated microvesicles range in size from 2 nm to 5000 nm,
    wherein the isolated microvesicles result in increased migration of non-proliferating cultured fibroblasts in a

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
agacctcaca gtaaaaatag gtga                                          24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctgatgggac ccactccatc                                               20

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gaagacctca cagtaaaaat aggtg                                         25

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctgatgggac ccactccatc                                               20
``` cell migration assay when administered to the non-proliferating cultured fibroblasts, and wherein administering the pharmaceutical composition of isolated microvesicles to the skin wound of the patient results in regeneration of at least one skin tissue in the skin wound.

2. The method of claim 1, wherein the skin wound is a full-thickness wound.

3. The method of claim 1, wherein the skin wound is a burn.

4. The method of claim 1, wherein the at least one skin tissue regenerated in the skin wound is selected from the group consisting of epithelial tissue, stromal tissue, nerve tissue, vascular tissue, and adnexal tissue.

5. The method of claim 1, wherein wrinkle formation or scar formation is reduced in the treated skin wound of the patient.

6. The method of claim 1, wherein the pharmaceutical composition of isolated microvesicles does not provoke a significant inflammatory response in the skin wound of the patient.

7. The method of claim 1, wherein the step of washing the precipitated microvesicles comprises centrifugal filtration.

8. The method of claim 1, wherein the isolated microvesicles have a molecular weight of at least 100 kDa.

9. The method of claim 1, wherein the PEG has an average molecular weight of 20,000 Da.

10. The method of claim 1, wherein the PEG is used at a percentage of between 5% and 25%.

11. The method of claim 1, wherein the mesenchymal stem cell is from bone marrow.

12. The method of claim 1, wherein the mesenchymal stem cell is allogeneic in origin.

13. The method of claim 1, wherein the isolated microvesicles have uncorrugated borders when examined by electron microscopy.

14. The method of claim 1, wherein the microvesicles are further processed to isolate microvesicles having at least one characteristic selected from the group consisting of: a particular size, a particular size range, a particular molecular weight, a particular weight range, and containing a specific molecule.

15. The method of claim 2, wherein the microvesicles are further processed to isolate microvesicles having a size of 2 nm to 200 nm.

16. A method of treating a burn wound in a patient in need thereof, the method comprising administering a pharmaceutical composition of isolated microvesicles to the burn wound of the patient,
wherein the isolated microvesicles are prepared comprising the steps of:
(a) obtaining a biological fluid containing mammalian microvesicles from a mesenchymal stem cell;
(b) precipitating the microvesicles by adding polyethylene glycol (PEG) to the biological fluid;
(c) washing the precipitated microvesicles to remove the PEG,
(d) isolating the microvesicles to obtain isolated microvesicles; and
(e) providing a therapeutically effective amount of the precipitated isolated microvesicles as a pharmaceutical composition,
wherein the precipitated microvesicles range in size from 2 nm to 5000 nm,
wherein the isolated microvesicles result in increased migration of non-proliferating cultured fibroblasts in a cell migration assay when administered to the non-proliferating cultured fibroblasts, and wherein administering the pharmaceutical composition of isolated microvesicles to the burn wound of the patient results in in regeneration of at least one skin tissue in the burn wound.

17. The method of claim 16, wherein the burn wound is selected from a second-degree burn and a full-thickness burn.

18. The method of claim 16, wherein the skin tissue regenerated in the burn wound of the patient is selected from the group consisting of epithelial tissue, stromal tissue, nerve tissue, vascular tissue, and adnexal tissue.

19. The method of claim 16, wherein wrinkle formation or scar formation is reduced in the healed burn wound of the patient.

20. The method of claim 16, wherein the pharmaceutical composition of isolated microvesicles does not provoke a significant inflammatory response in the patient.

21. The method of claim 16, wherein the step of washing the precipitated microvesicles comprises centrifugal filtration.

22. The method of claim 16, wherein the isolated microvesicles have a molecular weight of at least 100 kDa.

23. The method of claim 16, wherein the PEG has an average molecular weight of 20,000 Da.

24. The method of claim 16, wherein the PEG is used at a percentage of between 5% and 25%.

25. The method of claim 16, wherein the mesenchymal stem cell is from bone marrow.

26. The method of claim 16, wherein the mesenchymal stem cell is allogeneic in origin.

27. The method of claim 16, wherein the isolated microvesicles have uncorrugated borders when examined by electron microscopy.

28. The method of claim 16, wherein the microvesicles are further processed to isolate microvesicles having at least one characteristic selected from the group consisting of: a particular size, a particular size range, a particular molecular weight, a particular weight range, and containing a specific molecule.

29. The method of claim 16, wherein the microvesicles are further processed to isolate microvesicles having a size of 2 nm to 200 nm.

30. A method of treating a burn wound in a patient in need thereof, the method comprising
administering a pharmaceutical composition of isolated microvesicles directly to the burn wound of the patient,
wherein the isolated microvesicles are prepared comprising the steps of:
(a) obtaining culture medium conditioned using human bone marrow-derived mesenchymal stem cells, the culture medium containing microvesicles;
(b) precipitating the microvesicles by adding polyethylene glycol (PEG) to the biological fluid;
(c) washing the precipitated microvesicles to remove the PEG;
(d) isolating the microvesicles to obtain isolated microvesicles; and
(e) providing a therapeutically effective amount of the isolated microvesicles as a pharmaceutical composition,
wherein the precipitated microvesicles range in size from 2 nm to 5000 nm,
wherein the isolated microvesicles result in increased migration of non-proliferating cultured fibroblasts in a cell migration assay when administered to the non-proliferating cultured fibroblasts, and wherein administering the pharmaceutical composition of isolated microvesicles to the burn wound of the patient results in in regeneration of at least one skin tissue in the burn wound of the patient.

31. The method of claim 30, wherein the burn wound is a full-thickness burn.

32. The method of claim 30, wherein the burn wound is a second degree burn.

33. The method of claim 30, wherein the isolated microvesicles have a molecular weight of at least 100 kDa.

34. The method of claim 30, wherein the mesenchymal stem cell is autologous in origin.

35. The method of claim 30, wherein the mesenchymal stem cell is allogeneic in origin.

36. The method of claim 30, wherein administering a pharmaceutical composition of isolated microvesicles directly to the burn wound of the patient is by local injection.

* * * * *